United States Patent
Boyle et al.

(10) Patent No.: US 9,630,931 B2
(45) Date of Patent: *Apr. 25, 2017

(54) PHARMACEUTICALLY ACTIVE PYRAZINE DERIVATIVES

(71) Applicant: Sentinel Oncology Limited, Cambridge (GB)

(72) Inventors: Robert George Boyle, Cambridge (GB); Richard Justin Boyce, Newmarket (GB)

(73) Assignee: SENTINEL ONCOLOGY LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,678

(22) PCT Filed: Nov. 16, 2012

(86) PCT No.: PCT/EP2012/072917
§ 371 (c)(1),
(2) Date: May 15, 2014

(87) PCT Pub. No.: WO2013/072502
PCT Pub. Date: May 23, 2013

(65) Prior Publication Data
US 2014/0323484 A1 Oct. 30, 2014

(30) Foreign Application Priority Data

Nov. 16, 2011 (GB) .................................. 1119799.3

(51) Int. Cl.
| | | |
|---|---|---|
| *C07D 241/26* | (2006.01) | |
| *A61K 31/497* | (2006.01) | |
| *C07D 403/12* | (2006.01) | |
| *A61K 31/5377* | (2006.01) | |
| *C07D 401/12* | (2006.01) | |
| *A61K 45/06* | (2006.01) | |
| *C07D 413/12* | (2006.01) | |

(52) U.S. Cl.
CPC .......... *C07D 241/26* (2013.01); *A61K 31/497* (2013.01); *A61K 31/5377* (2013.01); *A61K 45/06* (2013.01); *C07D 401/12* (2013.01); *C07D 403/12* (2013.01); *C07D 413/12* (2013.01)
(Continued)

(58) Field of Classification Search
None
See application file for complete search history.

(56) References Cited

U.S. PATENT DOCUMENTS 8,716,287 B2 * 5/2014 Boyle .................. C07D 241/20
514/235.8

FOREIGN PATENT DOCUMENTS

| WO | WO 02/070494 A1 | 9/2002 |
| WO | WO 2005/072733 A1 | 8/2005 |
| WO | WO 2006/014359 A2 | 2/2006 |
| WO | WO 2006/021002 A2 | 2/2006 |
| WO | WO 2011/141716 A2 | 11/2011 |

OTHER PUBLICATIONS

PCT International Search Report, PCT Application No. PCT/EP2012/072917, Apr. 3, 2013, 4 pages.
PCT International Written Opinion, PCT Application No. PCT/EP2012/072917, Apr. 3, 2013, 6 pages.
European Examination Report, European Application No. 12810111.0, Mar. 26, 2015, 5 pages.

* cited by examiner

*Primary Examiner* — San-Ming Hui
*Assistant Examiner* — Andrew Lee
(74) *Attorney, Agent, or Firm* — Kilpatrick Townsend & Stockton LLP

(57) ABSTRACT

The invention provides compounds which inhibit or modulate the activity of Chk-1 kinase and which are useful in the treatment of cancer. The compounds have the general formula (1):

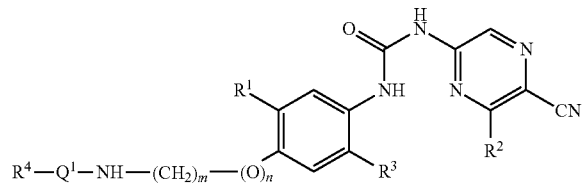

and salts, N-oxides and tautomers thereof, wherein m is 2, 3 or 4; n is 0 or 1; $Q^1$ is selected from a bond; C(=O); S(O); $SO_2$; and an alkylene chain of 1 to 4 carbon atoms in length between the moiety $R^4$ and the nitrogen atom. N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl or 1,1-cyclobutanediyl group; and/or (c) one carbon atom of the 1 to 4 carbon atoms of the alkylene chain may optionally be replaced by C(=O), S(O), or $SO_2$, provided that $Q^1$ contains no more than one C(=O), S(O), or $SO_2$ moiety; $R^1$ is selected from hydrogen, methyl, chlorine and bromine; $R^2$ is selected from hydrogen, methyl, methoxy and a group —$(O)_p$-$Q^2$-$R^5$; $R^3$ is selected from hydrogen, a group $Hyd^1$, a group —O-$Hyd^1$ and a group —$(O)_p$-$Q^2$-$R^5$; provided that when one of $R^2$ and $R^3$ is —$(O)_p$-$Q^2$-$R^5$, the other is selected from hydrogen, methoxy and methyl; and $R^4$ is selected from amino, NH-$Hyd^2$, N($Hyd^2$)$_2$; and a non-aromatic carbocyclic or heterocyclic ring of 4 to 7 ring members containing 0, 1, 2 or 3 heteroatom ring members selected from O, N and S and oxidized forms thereof; the carbocyclic or heterocyclic ring being optionally substituted with one or two substituents $R^9$. Also provided are pharmaceutical compositions containing the compounds and methods for making the compounds.

17 Claims, No Drawings

PHARMACEUTICALLY ACTIVE PYRAZINE DERIVATIVES

This invention relates to compounds that inhibit or modulate the activity of Chk-1 kinase. Also provided are pharmaceutical compositions containing the compounds and the therapeutic uses of the compounds.

BACKGROUND OF THE INVENTION

Chk-1 is a serine/threonine kinase involved in the induction of cell cycle checkpoints in response to DNA damage and replicative stress [*Clin. Can. Res.* 2007; 13(7)]. Cell cycle checkpoints are regulatory pathways that control the order and timing of cell cycle transitions. Most cancer cells have impaired G1 checkpoint activation due to a defective p53 tumor suppressor protein. Hahn et al., "Rules for making human tumor cells" *N. Engl. J. Med.* 2002; 347: 1593-603 and Hollstein et al., "p53 mutations in human cancers" *Science* 1991; 253: 49-53) have reported that tumours are associated with mutations in the p53 gene, a tumour suppressor gene found in about 50% of all human cancers.

Chk-1 inhibition abrogates the intra S and G2/M checkpoints and has been shown to selectively sensitise tumour cells to well known DNA damaging agents. Examples of DNA damaging agents where this sensitising effect has been demonstrated include Gemcitabine, Pemetrexed, Cytarabine, Irinotecan, Camptothecin, Cisplatin, Carboplatin [*Clin. Cancer Res.* 2010, 16, 376], Temozolomide [*Journal of Neurosurgery* 2004, 100, 1060], Doxorubicin [*Bioorg. Med. Chem. Lett.* 2006; 16:421-6], Paclitaxel [WO2010149394], Hydroxy urea [*Nat. Cell. Biol.* 2005 February; 7(2):195-20] and ionising radiation [*Clin. Cancer Res.* 2010, 16, 2076].

Recently published data have also shown that Chk-1 inhibitors may act synergistically with PARP inhibitors [*Cancer Res.;* 66: (16)], Mek inhibitors [*Blood.* 2008 Sep. 15; 112(6): 2439-2449], Farnesyltransferase inhibitors [*Blood.* 2005 Feb. 15; 105(4):1706-016], Rapamycin [*Mol. Cancer Ther.* 2005 March; 4(3):457-70] and Src inhibitors [*Blood.* 2011 Feb. 10; 117(6):1947-57].

Resistance to chemotherapy and radiotherapy, a clinical problem for conventional therapy, has been associated with activation of the DNA damage response in which Chk-1 has been implicated (Chk-1 activation is associated with radioresistence in glioblastoma [*Nature;* 2006; 444(7):756-760] and the inhibition of Chk-1 sensitises lung cancer brain metastases to radiotherapy [*Biochem. Biophys. Res. Commun.* 2011 Mar. 4; 406(1):53-8]).

It is also envisaged that Chk-1 inhibitors, either as single agents or in combination, may be useful in treating tumour cells in which constitutive activation of DNA damage and checkpoint pathways drive genomic instability. This phenotype is associated with complex karyotypes in samples from patients with acute myeloid leukemia (AML) [*Cancer Research* 2009, 89, 8652]. In vitro antagonisation of the Chk-1 kinase with a small molecule inhibitor or by RNA interference strongly reduces the clonogenic properties of high-DNA damage level AML samples. In contrast Chk-1 inhibition has no effect on normal hematopoietic progenitors. Furthermore, recent studies have shown that the tumour microenvironment drives genetic instability [*Nature;* 2008; (8):180-192] and loss of Chk-1 sensitises cells to hypoxia/reoxygenation [*Cell Cycle;* 2010; 9(13):2502]. In neuroblastoma, a kinome RNA interference screen demonstrated that loss of Chk-1 inhibited the growth of eight neuroblastoma cell lines. Tumour cells deficient in Fanconi anemia DNA repair have shown sensitivity to Chk-1 inhibition [*Molecular Cancer* 2009, 8:24]. It has been shown that the Chk-1 specific inhibitor PF-00477736 inhibits the growth of thirty ovarian cancer cell lines [Bukczynska et al, 23$^{rd}$ Lorne Cancer Conference] and triple negative negative breast cancer cells [*Cancer Science* 2011, 102, 882]. Also, PF-00477736 has displayed selective single agent activity in a MYC oncogene driven murine spontaneous cancer model [Ferrao et al, *Oncogene* (15 Aug. 2011)]. Chk-1 inhibition, by either RNA interference or selective small molecule inhibitors, results in apoptosis of MYC-overexpressing cells both in vitro and in an in vivo mouse model of B-cell lymphoma [Höglund et al., *Clinical Cancer Research,* Online First Sep. 20, 2011]. The latter data suggest that Chk-1 inhibitors would have utility for the treatment of MYC-driven malignancies such as B-cell lymphoma/leukemia, neuroblastoma and some breast and lung cancers.

Various attempts have been made to develop inhibitors of Chk-1 kinase. For example, WO 03/10444 and WO 2005/072733 (both in the name of Millennium) disclose aryl/heteroaryl urea compounds as Chk-1 kinase inhibitors. US2005/215556 (Abbott) discloses macrocyclic ureas as kinase inhibitors. WO 02/070494, WO2006014359 and WO2006021002 (all in the name of Icos) disclose aryl and heteroaryl ureas as Chk-1 inhibitors.

Our earlier application PCT/GB2011/000739 discloses a class of substituted pyrazinyl-phenyl ureas as Chk-1 kinase inhibitors.

SUMMARY OF THE INVENTION

The present invention provides compounds having activity as Chk-1 kinase inhibitors.

Accordingly, in a first embodiment (Embodiment 1.0), the invention provides a compound of the formula (1):

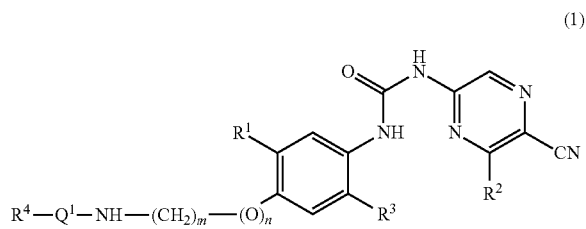

or a salt, N-oxide or tautomer thereof, wherein:

m is 2, 3 or 4;

n is 0 or 1;

$Q^1$ is selected from a bond; C(=O); S(O); SO$_2$; and an alkylene chain of 1 to 4 carbon atoms in length between the moiety $R^4$ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl group or cyclobutane-1,1-diyl group; and/or (c) one carbon atom of the 1 to 4 carbon atoms of the alkylene chain may optionally be replaced by C(=O), S(O), or SO$_2$, provided that $Q^1$ contains no more than one C(=O), S(O), or SO$_2$ moiety;

$R^1$ is selected from hydrogen, methyl, chlorine and bromine;

$R^2$ is selected from hydrogen, methyl, methoxy and a group —(O)$_p$-Q$^2$-R$^5$;

p is 0 or 1;

R³ is selected from hydrogen, a group Hyd¹, a group —O-Hyd¹ and a group —(O)$_p$-Q²-R⁵; provided that when one of R² and R³ is —(O)$_p$-Q²-R⁵, the other is selected from hydrogen, methoxy and methyl;

Hyd¹ is a non-aromatic $C_{1-6}$ hydrocarbon group;

R⁴ is selected from amino, NH-Hyd², N(Hyd²)₂; and a non-aromatic carbocyclic or heterocyclic ring of 4 to 7 ring members containing 0, 1, 2 or 3 heteroatom ring members selected from O, N and S and oxidised forms of N and S; the carbocyclic or heterocyclic ring being optionally substituted with one or two substituents R⁹;

Hyd² is an unsubstituted non-aromatic $C_{1-6}$ hydrocarbon group; or a substituted non-aromatic $C_{2-6}$ hydrocarbon group bearing one or two substituents selected from hydroxy and amino;

Q² is an alkylene chain of 1 to 4 carbon atoms in length wherein one or more of the 1 to 4 carbon atoms of the alkylene chain may optionally be substituted with one or two $C_{1-4}$ alkyl groups and wherein one carbon atom of the 1 to 4 carbon atoms of the alkylene chain may optionally be replaced by a cyclopropane-1,1-diyl or cyclobutane-1,1-diyl group;

R⁵ is selected from NR⁶R⁷, or N(O)R⁶R⁷ and a cyclic group R⁸;

R⁶ and R⁷ are each independently selected from hydrogen and $C_{1-4}$ alkyl; or NR⁶R⁷ or N(O)R⁶R⁷ form a saturated heterocyclic ring of 4 to 7 ring members optionally containing a second heteroatom ring member selected from O, N and S and oxidised forms of N and S and being optionally substituted with one, two or three substituents selected from oxo, fluorine and methyl;

R⁸ is, a 4- to 8-membered non-aromatic heterocyclic group containing 1 or 2 heteroatom ring members selected from O, N, S and oxidised forms of N and S, wherein the heterocyclic group is optionally substituted with one, two or three substituents selected from oxo, fluorine and methyl; and wherein R⁸ is attached to Q² through a carbon atom of the heterocyclic group;

R⁹ is selected from oxo, halogen, cyano and a group R$^a$-R$^b$;

R$^a$ is a bond, O, CO, X¹C(X²), C(X²)X¹, X¹C(X²)X¹, S, SO, SO₂, NR$^c$, SO₂NR$^c$ or NR$^c$SO₂;

R$^b$ is:
hydrogen;
a carbocyclic and heterocyclic group having from 3 to 7 ring members, of which 0, 1, 2 or 3 are heteroatom ring members selected from O, N and S and oxidised forms of N and S, the carbocyclic or heterocyclic group being optionally substituted with one or more substituents R¹⁰; and
an acyclic $C_{1-6}$ hydrocarbon group optionally substituted with one or more substituents selected from hydroxy; oxo; halogen; cyano; nitro; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of N and S, the carbocyclic or heterocyclic group being optionally substituted with one or more substituents R¹⁰; wherein one or two but not all of the carbon atoms of the acyclic $C_{1-6}$ hydrocarbon group may optionally be replaced by O, S, SO, SO₂, NR$^c$, X¹C(X²), C(X²)X¹ or X¹C(X²)X¹;

R¹⁰ is selected from R⁹ except that R¹⁰ does not consist of or contain a cyclic group;

X¹ is O, S or NR$^c$; and

X² is =O, =S or =NR$^c$; and

R$^c$ is hydrogen or $C_{1-4}$ alkyl.

In another embodiment (Embodiment 1.1), the invention provides a compound of the formula (1):

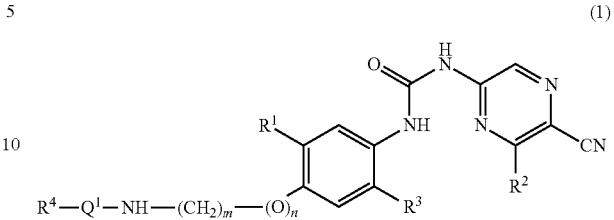

(1)

or a salt, N-oxide or tautomer thereof, wherein:

m is 2, 3 or 4;

n is 0 or 1;

Q¹ is selected from a bond; C(=O); S(O); SO₂; and an alkylene chain of 1 to 4 carbon atoms in length between the moiety R⁴ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl group; and/or (c) one carbon atom of the 1 to 4 carbon atoms of the alkylene chain may optionally be replaced by C(=O), S(O), or SO₂, provided that Q¹ contains no more than one C(=O), S(O), or SO₂ moiety;

R¹ is selected from hydrogen, chlorine and bromine;

R² is selected from hydrogen, methyl, methoxy and a group —(O)$_p$-Q²-R⁵;

p is 0 or 1;

R³ is selected from hydrogen, a group Hyd¹, a group —O-Hyd¹ and a group —(O)$_p$-Q²-R⁵; provided that when one of R² and R³ is —(O)$_p$-Q²-R⁵, the other is selected from hydrogen, methoxy and methyl;

Hyd¹ is a non-aromatic $C_{1-6}$ hydrocarbon group;

R⁴ is selected from amino, NH-Hyd², N(Hyd²)₂; and a non-aromatic carbocyclic or heterocyclic ring of 4 to 7 ring members containing 0, 1, 2 or 3 heteroatom ring members selected from O, N and S and oxidised forms of N and S; the carbocyclic or heterocyclic ring being optionally substituted with one or two substituents R⁹;

Hyd² is an unsubstituted non-aromatic $C_{1-6}$ hydrocarbon group; or a substituted non-aromatic $C_{2-6}$ hydrocarbon group bearing one or two substituents selected from hydroxy and amino;

Q² is an alkylene chain of 1 to 4 carbon atoms in length wherein one or more of the 1 to 4 carbon atoms of the alkylene chain may optionally be substituted with one or two $C_{1-4}$ alkyl groups and wherein one carbon atom of the 1 to 4 carbon atoms of the alkylene chain may optionally be replaced by a cyclopropane-1,1-diyl or cyclobutane-1,1-diyl group;

R⁵ is selected from NR⁶R⁷, or N(O)R⁶R⁷ and a cyclic group R⁸;

R⁶ and R⁷ are each independently selected from hydrogen and $C_{1-4}$ alkyl; or NR⁶R⁷ or N(O)R⁶R⁷ form a saturated heterocyclic ring of 4 to 7 ring members optionally containing a second heteroatom ring member selected from O, N and S and oxidised forms of N and S and being optionally substituted with one, two or three substituents selected from oxo, fluorine and methyl;

R⁸ is a 4- to 8-membered non-aromatic heterocyclic group containing 1 or 2 heteroatom ring members selected from O, N, S and oxidised forms of N and S, wherein the heterocyclic group is optionally substituted with one, two or three substituents selected from oxo, fluorine and methyl; and wherein $R^8$ is attached to $Q^2$ through a carbon atom of the heterocyclic group;

$R^9$ is selected from oxo, halogen, cyano and a group $R^a$-$R^b$;

$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;

$R^b$ is:
hydrogen;
a carbocyclic and heterocyclic group having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; and
an acyclic $C_{1-6}$ hydrocarbon group optionally substituted with one or more substituents selected from hydroxy; oxo; halogen; cyano; nitro; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; wherein one or two but not all of the carbon atoms of the acyclic $C_{1-6}$ hydrocarbon group may optionally be replaced by O, S, SO, $SO_2$, $NR^c$, $X^1C(X^2)$, $C(X^2)X^1$ or $X^1C(X^2)X^1$;

$R^{10}$ is selected from $R^9$ except that $R^{10}$ does not consist of or contain a cyclic group;

$X^1$ is O, S or $NR^c$; and
$X^2$ is =O, =S or =$NR^c$; and
$R^c$ is hydrogen or $C_{1-4}$ alkyl.

Particular and preferred compounds of the formula (1) are as defined in the following Embodiments 1.2 to 1.127:

1.2 A compound according to Embodiment 1.1 wherein $R^1$ is hydrogen.

1.2A A compound according to Embodiment 1.1 wherein $R^1$ is methyl.

1.3 A compound according to Embodiment 1.1 wherein $R^1$ is chlorine.

1.4 A compound according to Embodiment 1.1 wherein $R^1$ is bromine.

1.5 A compound according to any one of Embodiments 1.1 to 1.4 wherein n is 0.

1.6 A compound according to any one of Embodiments 1.1 to 1.4 wherein n is 1.

1.7 A compound according to any one of Embodiments 1.1 to 1.6 wherein m is 2.

1.8 A compound according to any one of Embodiments 1.1 to 1.6 wherein m is 3.

1.9 A compound according to any one of Embodiments 1.1 to 1.6 wherein m is 4.

1.10 A compound according to any one of Embodiments 1.1 to 1.6 wherein m is 2 or 3.

1.11 A compound according to any one of Embodiments 1.1 to 1.10 wherein $Q^1$ is selected from a bond; C(=O); S(O); $SO_2$; and an alkylene chain of 1 to 4 carbon atoms in length between the moiety $R^4$ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl group.

1.12 A compound according to Embodiment 1.11 wherein $Q^1$ is an alkylene chain of 1 to 4 carbon atoms in length between the moiety $R^4$ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl group.

1.13 A compound according to any one of Embodiments 1.1 to 1.12 wherein the alkylene chain $Q^1$ is 1 to 3 carbon atoms in length.

1.14 A compound according to Embodiment 1:13 wherein the alkylene chain $Q^1$ is 1 or 2 carbon atoms in length.

1.15 A compound according to Embodiment 1.14 wherein the alkylene chain $Q^1$ is 1 carbon atom in length.

1.16 A compound according to Embodiment 1.14 wherein the alkylene chain $Q^1$ is 2 carbon atoms in length.

1.17 A compound according to Embodiment 1.13 wherein the alkylene chain $Q^1$ is 3 carbon atoms in length.

1.18 A compound according to any one of Embodiments 1.1 to 1.12 wherein the alkylene chain $Q^1$ has the formula —$(CH_2)_j$— where j is 1 to 4.

1.19 A compound according to Embodiment 1.18 wherein j is 1 to 3.

1.20 A compound according to Embodiment 1.18 wherein j is 1 or 2.

1.21 A compound according to Embodiment 1.18 wherein j is 1.

1.22 A compound according to Embodiment 1.18 wherein j is 2.

1.23 A compound according to Embodiment 1.18 wherein j is 3.

1.24 A compound according to Embodiment 1.18 wherein j is 4.

1.25 A compound according to any one of Embodiments 1.1 to 1.17 wherein one or more, of the 1-4 carbon atoms in the alkylene chain $Q^1$ is substituted with one or two $C_{1-4}$ alkyl groups.

1.26 A compound according to Embodiment 1.25 wherein one or two carbon atoms of the alkylene chain $Q^1$ are substituted with one or two $C_{1-4}$ alkyl groups.

1.27 A compound according to Embodiment 1.25 or 1.26 wherein the $C_{1-4}$ alkyl groups are methyl groups.

1.28 A compound according to Embodiment 1.27 wherein one carbon atom of the alkylene chain $Q^1$ is substituted with a methyl group.

1.28A A compound according to Embodiment 1.27 wherein one carbon atom of the alkylene chain $Q^1$ is substituted with an isopropyl group.

1.29 A compound according to any one of Embodiments 1.1 to 1.12 wherein the alkylene chain $Q^1$ is represented by —$CH_2$—$CH_2$—, —$CH_2$— or —CHMe-.

1.30 A compound according to Embodiment 1.29 wherein the alkylene chain $Q^1$ is represented by —$CH_2$—$CH_2$—.

1.31 A compound according to Embodiment 1.29 wherein the alkylene chain $Q^1$ is represented by —$CH_2$—.

1.32 A compound according to Embodiment 1.29 wherein the alkylene chain $Q^1$ is represented by —CHMe-.

1.33 A compound according to Embodiment 1.32 wherein the compound has an S-stereochemical configuration with regard to the group —CHMe-.

1.33A A compound according to Embodiment 1.32 wherein the compound has an R-stereochemical configuration with regard to the group —CHMe-.

1.34 A compound according to any one of Embodiments 1.1 to 1.11 wherein $Q^1$ is selected from a bond; C(=O); S(O) and $SO_2$.

1.35 A compound according to Embodiment 1.34 wherein $Q^1$ is a bond.

1.36 A compound according to Embodiment 1.34 wherein $Q^1$ is C(=O).

1.37 A compound according to Embodiment 1.34 wherein $Q^1$ is S(O).

1.38 A compound according to Embodiment 1.34 wherein $Q^1$ is $SO_2$.

1.39 A compound according to any one of Embodiments 1.1 to 1.38 wherein $R^2$ is selected from hydrogen, methyl and methoxy.

1.40. A compound according to Embodiment 1.39 wherein $R^2$ is hydrogen.

1.41 A compound according to any one of Embodiments 1.1 to 1.38 wherein $R^2$ is a group $-(O)_p$-$Q^2$-$R^5$.

1.42 A compound according to any one of Embodiments 1.1 to 1.41 wherein $R^3$ is selected from hydrogen, a group $Hyd^1$ and a group $-O$-$Hyd^1$; provided that when $R^2$ is $-(O)_p$-$Q^2$-$R^5$, $R^3$ is selected from hydrogen, methoxy and methyl.

1.43 A compound according to Embodiment 1.42 wherein $R^3$ is selected from hydrogen, a group $Hyd^1$ and a group $-O$-$Hyd^1$ wherein $Hyd^1$ is a saturated $C_{1-3}$ hydrocarbon group, provided that when $R^2$ is $-(O)_p$-$Q^2$-$R^5$, $R^3$ is selected from hydrogen, methoxy and methyl.

1.44 A compound according to Embodiment 1.43 wherein $R^3$ is selected from hydrogen, $C_{1-3}$alkyl, $C_{1-3}$ alkoxy, cyclopropyl and cyclopropoxy.

1.45 A compound according to Embodiment 1.44 wherein $R^3$ is selected from hydrogen and $C_{1-3}$ alkoxy.

1.46 A compound according to Embodiment 1.45 wherein $R^3$ is selected from hydrogen, methoxy, ethoxy and isopropoxy.

1.47 A compound according to Embodiment 1.46 wherein $R^3$ is hydrogen.

1.48 A compound according to Embodiment 1.46 wherein $R^3$ is methoxy.

1.49 A compound according to Embodiment 1.46 wherein $R^3$ is isopropoxy.

1.50 A compound according to any one of Embodiments 1.1 to 1.49 wherein $R^4$ is an optionally substituted 4- to 7-membered carbocyclic or heterocyclic ring.

1.51 A compound according to Embodiment 1.50 wherein $R^4$ is an optionally substituted 5- or 6-membered ring.

1.52 A compound according to any one Embodiments 1.1 to 1.51 wherein the carbocyclic or heterocyclic ring $R^4$ is a saturated ring.

1.53 A compound according to any one of Embodiments 1.1 to 1.52 wherein the carbocyclic or heterocyclic ring contains 0, 1 or 2 heteroatom ring members.

1.54 A compound according to Embodiment 1.53 wherein the heteroatom ring members when present are selected from O and N.

1.55 A compound according to any one of Embodiments 1.1 to 1.54 wherein $R^4$ is an optionally substituted heterocyclic ring and contains at least one nitrogen ring member.

1.56 A compound according to Embodiment 1.55 wherein the heterocyclic ring contains one nitrogen atom ring member and optionally a second heteroatom ring member selected from O and N.

1.56A A compound according to Embodiment 1.55 wherein the heterocyclic ring contains one nitrogen atom ring member and optionally a second heteroatom ring member selected from O, N and S and oxidized forms thereof.

1.57 A compound according to any one of Embodiments 1.1 to 1.53 wherein $R^4$ is an optionally substituted $C_{3-7}$ cycloalkyl group.

1.58 A compound according to Embodiment 1.57 which is an optionally substituted $C_{4-6}$ cycloalkyl group.

1.59 A compound according to any one of Embodiments 1.1 to 1.58 wherein $R^4$ is selected from optionally substituted cyclohexyl, piperidinyl, piperazinyl and morpholinyl groups.

1.59A A compound according to any one of Embodiments 1.1 to 1.58 wherein $R^4$ is selected from optionally substituted cyclohexyl, pyrrolidinyl, piperidinyl, piperazinyl and morpholinyl groups.

1.60 A compound according to Embodiment 1.59 wherein $R^4$ is an optionally substituted cyclohexyl group.

1.61 A compound according to Embodiment 1.59 wherein $R^4$ is an optionally substituted piperidinyl group.

1.62 A compound according to Embodiment 1.59 wherein $R^4$ is an optionally substituted piperazinyl group.

1.63 A compound according to Embodiment 1.59 wherein $R^4$ is an optionally substituted morpholinyl group.

1.63A A compound according to Embodiment 1.59 wherein $R^4$ is an optionally substituted pyrrolidinyl group.

1.64 A compound according to any one of Embodiments 1.1 to 1.63 wherein the carbocyclic or heterocyclic group $R^4$ is linked to $Q^1$ through a carbon atom of $R^4$.

1.65 A compound according to any one of Embodiments 1.1 to 1.56 and 1.59 to 1.63 wherein the heterocyclic group $R^4$ is linked to $Q^1$ through a nitrogen ring member of $R^4$.

1.66 A compound according to any one of Embodiments 1.1 to 1.65 wherein the carbocyclic or heterocyclic group $R^4$ is unsubstituted or is substituted with one substituent $R^9$.

1.67 A compound according to any one of Embodiments 1.1 to 1.65 wherein the carbocyclic or heterocyclic group $R^4$ is unsubstituted or is substituted with two substituents $R^9$.

1.68 A compound according to any one of Embodiments 1.1 to 1.67 wherein the carbocyclic or heterocyclic group $R^4$ is unsubstituted or is substituted with one or two substituents $R^9$ selected from oxo, halogen, cyano and a group $R^a$-$R^b$; wherein $R^8$ is a bond, O, CO, $NR^cC(O)$, $C(O)NR^c$, $NR^cC(O)NR^c$, $O(CO)NR^c$, $NR^cC(O)O$, S, SO, $SO_2$, $NR^c$, $SO_2NR^c$ or $NR'SO_2$; and $R^b$ is:

hydrogen;

a carbocyclic and heterocyclic group having from 3 to 6 ring members, of which 0, 1 or 2 are heteroatom ring members selected from O, N and S and oxidised forms thereof, the carbocyclic or heterocyclic group being optionally substituted with one or more substituents $R^{10}$; and an acyclic $C_{1-6}$ hydrocarbon group optionally substituted with one or more substituents selected from hydroxy; oxo; fluorine; cyano; carboxy; amino; mono- or di-$C_{1-4}$ alkylamino; and carbocyclic and heterocyclic groups having from 3 to 7 ring members, of which 0, 1 or 2 are heteroatom ring members selected from O, N and S and oxidised of N and S, the carbocyclic or heterocyclic group being optionally substituted with one or more substituents $R^{10}$; wherein one or two but not all of the carbon atoms of the acyclic $C_{1-6}$ hydrocarbon group may optionally be replaced by O, S, SO, $SO_2$, $X^1C(X^2)$, $C(X^2)X^1$ or $X^1C(X^2)X^1$.

1.69 A compound according to Embodiment 1.68 wherein the carbocyclic or heterocylic group $R^4$ is unsubstituted or is substituted with one or two substituents $R^9$ selected from oxo, fluorine, cyano and a group $R^a$-$R^b$; wherein $R^a$ is a bond, O, CO, $SO_2$, $NR^c$ or $SO_2NR^c$; and $R^b$ is:

hydrogen;

a saturated carbocyclic and heterocyclic group having from 3 to 6 ring members, of which 0, 1 or 2 are heteroatom ring members selected from O, N and S and oxidised forms thereof, the saturated carbocyclic or heterocyclic group being optionally substituted with one or more substituents $R^{10}$; and an acyclic $C_{1-6}$ hydrocarbon group optionally substituted with one or more substituents selected from hydroxy; oxo; fluorine; cyano; amino; mono- or di-$C_{1-4}$ alkylamino; and saturated carbocyclic and heterocyclic groups having from 3 to 6 ring members, of which 0, 1 or 2 are heteroatom ring members selected from O and N, the carbocyclic or heterocyclic group being optionally substituted with one or more substituents $R^{10}$; wherein one or two but not all of the carbon atoms of the acyclic $C_{1-6}$ hydrocarbon group may optionally be replaced by O or $NR^c$.

1.70 A compound according to Embodiment 1.69 wherein the carbocyclic or heterocyclic group $R^4$ is unsubstituted or is substituted with one, or two substituents $R^9$ selected from oxo, cyano and a group $R^a$-$R^b$; wherein $R^a$ is a bond, O, CO, $SO_2$ or $NR^c$; and $R^b$ is:

hydrogen;

a $C_{3-6}$ cycloalkyl group optionally substituted with one or more substituents $R^{10}$;

a saturated heterocyclic group having from 4 to 6 ring members, of which 0, 1 or 2 are heteroatom ring members selected from O and N and oxidised forms thereof, the saturated heterocyclic group being optionally substituted with one or more substituents $R^{10}$; and a $C_{1-6}$ alkyl group optionally substituted with one or more substituents selected from hydroxy; oxo; fluorine; cyano; amino; mono- or di-$C_{1-2}$ alkylamino; and $C_{3-6}$ cycloalkyl or saturated heterocyclic groups having from 4 to 6 ring members, of which 0, 1 or 2 are heteroatom ring members selected from O and N, the cycloalkyl or heterocyclic group being optionally substituted with one or more substituents $R^{10}$; wherein one or two but not all of the carbon atoms of the acyclic $C_{1-6}$ hydrocarbon group may optionally be replaced by O or $NR^c$.

1.71 A compound according to any one Embodiments 1.1 to 1.70 wherein $R^{10}$ is absent or is selected from $C_{1-4}$ alkyl; cyclopropyl; hydroxy; fluorine; cyano; oxo; carbamoyl; amino; mono- or di-$C_{1-4}$alkylamino.

1.72 A compound according to Embodiment 1.71 wherein $R^{10}$ is absent or is selected from $C_{1-3}$ alkyl; cyclopropyl; hydroxy; fluorine; cyano; oxo; amino; mono- or di-$C_{1-2}$ alkylamino.

1.73 A compound according to Embodiment 1.72 wherein $R^{10}$ is absent or is selected from methyl; ethyl; isopropyl; cyclopropyl; hydroxy; fluorine; cyano; oxo; amino; methylamino and dimethylamino.

1.74 A compound according to Embodiment 1.73 wherein $R^{10}$ is absent.

1.75 A compound according to any one of Embodiments 1.1 to 1.70 wherein $R^9$ is absent or is selected from $R^{11}$; C(=O)$R^{11}$; and $SO_2R^{11}$; where $R^{11}$ is a $C_{1-6}$ hydrocarbon group which is optionally substituted with one or more substituents selected from hydroxy, fluorine, amino, methylamino, dimethylamino, cyano, methoxy, ethoxy, carboxy, carbamoyl, methylcarbamoyl and dimethylcarbamoyl.

1.76 A compound according to Embodiment 1.75 wherein $R^9$ is absent or is selected from $R^{11}$, C(=O)$R^{11}$ and $SO_2R^{11}$, where $R^{11}$ is a $C_{1-4}$ hydrocarbon group.

1.77 A compound according to Embodiment 1.76 wherein $R^9$ is absent or is selected from $C_{1-4}$ alkyl, $C_{1-4}$ alkylsulphonyl and $C_{1-4}$ acyl.

1.78 A compound according to Embodiment 1.77 wherein $R^9$ is absent or is selected from methyl, methylsulphonyl and cyclopropylcarbonyl.

1.79 A compound according to any one of Embodiments 1.1 to 1.78 wherein $R^4$ is selected from groups A to L below, wherein the asterisk indicates the point of attachment to $Q^1$:

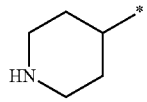

A

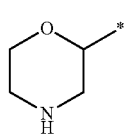

B

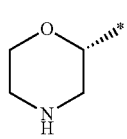

C

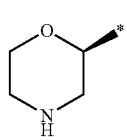

D

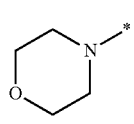

E

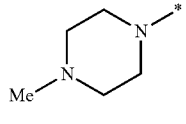

F

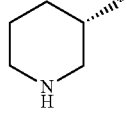

G

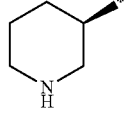

H

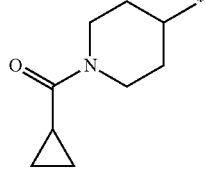

J

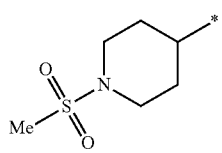

K

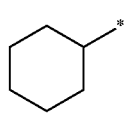

L

-continued

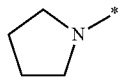
M 1.79A A compound according to Embodiment 1.79 wherein $R^4$ is selected from groups A to L.

1.80 A compound according to any one of Embodiments 1.1 to 1.49 wherein $R^4$ is selected from amino, NH-Hyd$^2$ and N(Hyd$^2$)$_2$.

1.81 A compound according to any one of Embodiments 1.1 to 1.49 and 1.80 wherein Hyd$^2$ is an unsubstituted $C_{1-4}$ hydrocarbon group; or a substituted $C_{2-4}$ hydrocarbon group bearing one or two substituents selected from hydroxy and amino.

1.82 A compound according to Embodiment 1.80 or Embodiment 1.81 wherein Hyd$^2$ is an unsubstituted $C_{1-3}$ hydrocarbon group; or a substituted $C_{2-3}$ hydrocarbon group bearing one or two substituents selected from hydroxy and amino.

1.83 A compound according to Embodiment 1.82 wherein $R^4$ is selected from amino, methylamino, ethylamino, isopropylamino, dimethylamino, diethylamino, ethyl(methyl)amino, isopropyl(methyl)amino, cyclopropylamino, 2-hydroxyethylamino, 2-hydroxypropylamino, 3-hydroxypropylamino, 2-aminoethylamino, 2-aminopropylamino and 3-amino-propylamino.

1.84 A compound according to any one of Embodiments 1.1 to 1.41 to 1.83 wherein one of $R^2$ and $R^3$ is —(O)$_p$-Q$^2$-R$^5$.

1.85 A compound according to Embodiment 1.84 wherein $R^3$ is —(O)$_p$-Q$^2$-R$^5$.

1.86 A compound according to Embodiment 1.84 or Embodiment 0.1.85 wherein Q$^2$ is an alkylene chain of 2 to 4 carbon atoms in length wherein one or more of the 2 to 4 carbon atoms of the alkylene chain may optionally be substituted with one or two $C_{1-4}$ alkyl groups and wherein one carbon atom of the 2 to 4 carbon atoms of the alkylene chain may optionally be replaced by a cyclopropane-1,1-diyl or cyclobutane-1,1-diyl group; and $R^5$ is NR$^6$R$^7$ or N(O)R$^6$R$^7$.

1.87 A compound according to Embodiment 1.86 wherein Q$^2$ is an alkylene chain of 2 to 4 carbon atoms in length wherein one or more of the 2 to 4 carbon atoms of the alkylene chain may optionally be substituted with one or two methyl groups and wherein one carbon atom of the 2 to 4 carbon atoms of the alkylene chain may optionally be replaced by a cyclopropane-1,1-diyl or cyclobutane-1,1-diyl group.

1.88 A compound according to Embodiment 1.87 wherein Q$^2$ is an alkylene chain of 2 to 4 carbon atoms in length wherein one of the 2 to 4 carbon atoms of the alkylene chain may optionally be substituted with one or two methyl groups and wherein one carbon atom of the 2 to 4 carbon atoms of the alkylene chain may optionally be replaced by a cyclopropane-1,1-diyl or cyclobutane-1,1-diyl group.

1.89 A compound according to Embodiment 1.88 wherein Q$^2$ is an alkylene chain of 2 to 3 carbon atoms in length wherein (i) one of the 2 to 4 carbon atoms of the alkylene chain may optionally be substituted with one or two methyl groups; or (ii) wherein one carbon atom of the 2 to 4 carbon atoms of the alkylene chain may optionally be replaced by a cyclopropane-1,1-diyl or cyclobutane-1,1-diyl group.

1.90. A compound according to Embodiment 1.89 wherein Q$^2$ is selected from —CH$_2$CH$_2$— and —CH$_2$CH$_2$CH$_2$—.

1.91 A compound according to Embodiment 1.90 wherein Q$^2$ is a group —CH$_2$CH$_2$—.

1.92 A compound according to any one of Embodiments 1.86 to 1.91 wherein $R^6$ is selected from hydrogen and $C_{1-3}$ alkyl.

1.93 A compound according to Embodiment 1.92 wherein $R^6$ is selected from hydrogen and $C_{1-2}$ alkyl.

1.94 A compound according to Embodiment 1.93 wherein $R^6$ is selected from hydrogen and methyl.

1.95 A compound according to Embodiment 1.94 wherein $R^6$ is methyl.

1.96 A compound according to any one of Embodiments 1.86 to 1.95 wherein $R^7$ is selected from hydrogen and $C_{1-3}$ alkyl.

1.97 A compound according to Embodiment 1.96 wherein $R^7$ is selected from hydrogen and $C_{1-2}$ alkyl.

1.98 A compound according to Embodiment 1.97 wherein $R^7$ is selected from hydrogen and methyl.

1.99 A compound according to Embodiment 1.98 wherein $R^7$ is methyl.

1.100 A compound according to any one of Embodiments 1.1 to 1.99 wherein $R^5$ is NR$^6$R$^7$.

1.101 A compound according to any one of Embodiments 1.1 to 1.99 wherein $R^5$ is N(O)R$^6$R$^7$ and $R^6$ and $R^7$ are each other than hydrogen.

1.1.02 A compound according to any one of Embodiments 1.1 to 1.91 wherein $R^5$, is NR$^6$R$^7$ or N(O)R$^6$R$^7$ wherein $R^6$ and $R^7$ together with the nitrogen atom to which they are attached form a 4 to 7-membered non-aromatic heterocyclic ring optionally containing a second heteroatom ring member selected from O, N and S and being optionally substituted with one, two or three substituents selected from oxo, fluorine and methyl.

1.103 A compound according to Embodiment 1.102 wherein the non-aromatic heterocyclic ring is a saturated heterocyclic ring.

1.104 A compound according to Embodiment 1.103 wherein the saturated heterocyclic ring is selected from optionally substituted piperidine, piperazine, morpholine, pyrrolidine and azetidine rings.

1.105. A compound according to Embodiment 1.104 wherein the saturated heterocyclic ring is selected from piperidine, piperazine, morpholine and pyrrolidine rings, each optionally substituted with one or two substituents, selected from oxo and methyl.

1.106 A compound according to any one of Embodiments 1.1 to 1.85 wherein $R^5$ is a cyclic group $R^8$ and Q$^2$ is an alkylene chain of 1 to 3 carbon atoms in length, wherein one or more of the 1 to 3 carbon atoms of the alkylene chain may optionally be substituted with one or two methyl groups or one of the 1 to 3 carbon atoms of the alkylene chain may optionally be replaced by a cyclopropane-1,1-diyl group.

1.107 A compound according to Embodiment 1.106 wherein Q$^2$ is an alkylene chain of 1 to 3 carbon atoms in length.

1.108 A compound according to Embodiment 1.107 wherein Q$^2$ is an alkylene chain of 1 to 2 carbon atoms in length.

1.109 A compound according to Embodiment 1.108 wherein Q$^2$ is —CH$_2$—.

1.110 A compound according to any one of Embodiments 1.1 to 1.85 and 1.106 to 1.109 wherein $R^8$ is a 4- to 7-membered non-aromatic monocyclic heterocyclic group or an 8- or 9-membered bridged bicyclic heterocyclic group, each containing 1 or 2 heteroatom ring members selected from O and N, provided that at least one heteroatom ring member is nitrogen, wherein the heterocyclic group is optionally substituted with 1 or 2 substituents selected from oxo, fluorine and methyl.

1.111 A compound according to Embodiment 1.110 wherein $R^8$ is a saturated 4- to 7-membered monocyclic heterocyclic group containing 1 or 2 heteroatom ring members selected from O and N, wherein the heterocyclic group is optionally substituted with 1 or 2 substituents selected from oxo, fluorine and methyl.

1.112 A compound according to Embodiment 1.111 wherein $R^8$ is selected from oxetan, azetidine, pyrrolidine, tetrahydrofuran, piperidine, piperazine, morpholine, tetrahydropyridone, and 8-aza-bicyclo[3.2.1]bicyclooctane groups, each optionally substituted with one or two methyl groups.

1.113 A compound according to Embodiment 1.112 wherein $R^8$ is selected from piperidine, piperazine and morpholine groups each optionally substituted with one or two methyl substituents.

1.114 A compound according to Embodiment 1.113 wherein $R^8$ is a morpholine group.

1.115 A compound according to Embodiment 1.114 wherein the morpholine group is a morpholin-2-yl group.

1.116 A compound according to Embodiment 1.115 wherein the morpholine group has the structure:

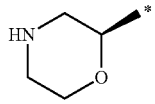

where the asterisk denotes the point of attachment to $Q^2$.

1.117 A compound according to any one of Embodiments 1.1 to 1.116 wherein, when one of $R^2$ and $R^3$ is $—(O)_p-Q^2-R^5$, p is 0.

1.118 A compound according to any one of Embodiments 1.1 to 1.116 wherein, when one of $R^2$ and $R^3$ is $—(O)_p-Q^2-R^5$, p is 1.

1.119 A compound according to any one of Embodiments 1.1 to 1.116 wherein one of $R^2$ and $R^3$ is $—(O)_p—Q^2-R^5$ and $R^4$ is a non-basic group.

1.120. A compound according to Embodiment 1.119 wherein $R^4$ contains no basic amino group.

1.121 A compound according to any one of Embodiments 1.1 to 1.40 and 1.42 to 1.83 wherein neither $R^2$ nor $R^3$ are $—(O)_p-Q^2-R^5$.

1.122 A compound according to Embodiment 1.1 having the formula (2):

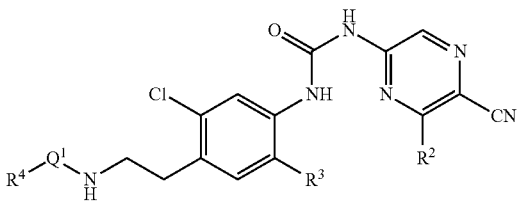

(2)

or a salt or tautomer thereof, wherein $R^2$, $R^3$, $R^4$ and $Q^1$ are as defined in any one of Embodiments 1.1 to 1.121.

1.122A A compound of the formula (3):

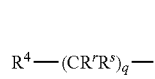

(3)

or a salt, N-oxide or tautomer thereof, wherein:

m is 2, 3 or 4;

n is 0 or 1;

q is 0, 1 or 2 and r is 0, 1 or 2 provided that the sum of q and r is 1, 2 or 3;

$R^p$, $R^q$, $R^r$ and $R^s$ are each independently selected from hydrogen and $C_{1-4}$ alkyl; and/or $CR^pR^q$ and $CR^rR^s$ may each form a cyclopropane-1,1-diyl or 1,1-cyclobutanediyl group;

$R^1$ is selected from hydrogen, methyl, chlorine and bromine;

$R^2$ is selected from hydrogen, methyl, methoxy and a group $—(O)_p-Q^2-R^5$;

p is 0 or 1;

$R^3$ is selected from hydrogen, a group $Hyd^1$, a group $—O-Hyd^1$ and a group $—(O)_p-Q^2-R^5$; provided that when one of $R^2$ and $R^3$ is $—(O)_p-Q^2-R^5$, the other is selected from hydrogen, methoxy and methyl;

$Hyd^1$ is a non-aromatic $C_{1-6}$ hydrocarbon group;

$R^4$ is selected from amino, $NH-Hyd^2$, $N(Hyd^2)_2$; and a non-aromatic carbocyclic or heterocyclic ring of 4 to 7 ring members containing 0, 1, 2 or 3 heteroatom ring members selected from O, N and S and oxidised forms of N and S; the carbocyclic or heterocyclic ring being optionally substituted with one or two substituents $R^9$;

$Hyd^2$ is an unsubstituted non-aromatic $C_{1-6}$ hydrocarbon group; or a substituted non-aromatic $C_{2-6}$ hydrocarbon group bearing one or two substituents selected from hydroxy and amino;

$Q^2$ is an alkylene chain of 1 to 4 carbon atoms in length wherein one or more of the 1 to 4 carbon atoms of the alkylene chain may optionally be substituted with one or two $C_{1-4}$ alkyl groups and wherein one carbon atom of the 1 to 4 carbon atoms of the alkylene chain may optionally be replaced by a cyclopropane-1,1-diyl or cyclobutane-1,1-diyl group;

$R^5$ is selected from $NR^6R^7$, or $N(O)R^6R^7$ and a cyclic group $R^8$;

$R^6$ and $R^7$ are each independently selected from hydrogen and $C_{1-4}$ alkyl; or $NR^6R^7$ or $N(O)R^6R^7$ form a saturated heterocyclic ring of 4 to 7 ring members optionally containing a second heteroatom ring member selected from O, N and S and oxidised forms of N and S and being optionally substituted with one, two or three substituents selected from oxo, fluorine and methyl;

$R^8$ is a 4- to 8-membered non-aromatic heterocyclic group containing 1 or 2 heteroatom ring members selected from O, N, S and oxidised forms of N and S, wherein the heterocyclic group is optionally substituted with one, two or three substituents selected from oxo, fluorine and methyl; and wherein $R^8$ is attached to $Q^2$ through a carbon atom of the heterocyclic group;

$R^9$ is selected from oxo, halogen, cyano and a group $R^a$-$R^b$;

$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;

$R^b$ is:
hydrogen;
a carbocyclic and heterocyclic group having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; and
an acyclic $C_{1-6}$ hydrocarbon group optionally substituted with one or more substituents selected from hydroxy; oxo; halogen; cyano; nitro; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; wherein one or two but not all of the carbon atoms of the acyclic $C_{1-6}$ hydrocarbon group may optionally be replaced by O, S, SO, $SO_2$, $NR^c$, $X^1C(X^2)$, $C(X^2)X^1$ or $X^1C(X^2)X^1$;

$R^{10}$ is selected from $R^9$ except that $R^{10}$ does not consist of or contain a cyclic group;

$X^1$ is O, S or $NR^c$; and
$X^2$ is =O, =S or =$NR^c$; and
$R^c$ is hydrogen or $C_{1-4}$ alkyl.

1.122B A compound according to Embodiment 1.22A wherein $R^1$, $R^2$, $R^3$, $R^4$, m and n are as defined in any one of Embodiments 1.2 to 1.121.

1.122C A compound according to Embodiment 1.122A or 1.122B wherein the sum of q and r is 1 or 2.

1.122D A compound according to Embodiment 1.122C wherein the sum of q and r is 1.

1.122E A compound according to Embodiment 1.122C wherein the sum of q and r is 2.

1.122F A compound according to any one of Embodiments 1.122A to 1.122E wherein $R^p$, $R^q$, $R^r$ and $R^s$ are each independently selected from hydrogen and methyl.

1.122G A compound according to any one of Embodiments 1.122A to 1.122F wherein no more than two $R^p$, $R^q$, $R^r$ and $R^s$ moieties in the groups $(CR^pR^q)_q$ and $CR^rR^s)_r$ are other than hydrogen.

1.122H A compound according to Embodiment 1.122G wherein no more than one $R^p$, $R^q$, $R^r$ or $R^s$ moiety in the groups $(CR^pR^q)_q$ and $CR^rR^s)_r$ is other than hydrogen.

1.122J A compound according to Embodiment 1.122H wherein the group:

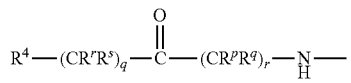

is selected from groups AA to AD below

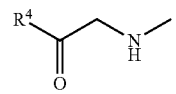

AA

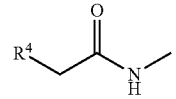

AB

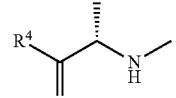

AC

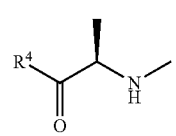

AD 1.122K A compound according to Embodiment 1.122J wherein the group:

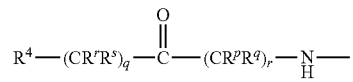

is group AA.

1.122L A compound according to Embodiment 1.122J wherein the group:

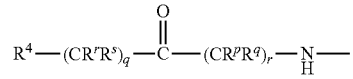

is group AB.

1.122M A compound according to Embodiment 1.122J wherein the group:

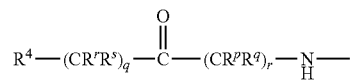

is group AC.

1.122N A compound according to Embodiment 1.122H wherein the group:

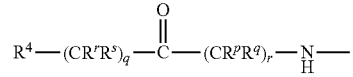

is group AD.

1.122P A compound according to Embodiment 1.122A which is selected from the title compounds of Examples 16, 17, 19, 22, 26, 27, 28, 30, 32, 33 and 37 below.

1.122Q A compound according to Embodiment 1.122P which is selected from the title compounds of Examples 16, 17, 19, 22, 26, 27, 28, 30, 32 and 33 below.

1.122R A compound of the formula (4):

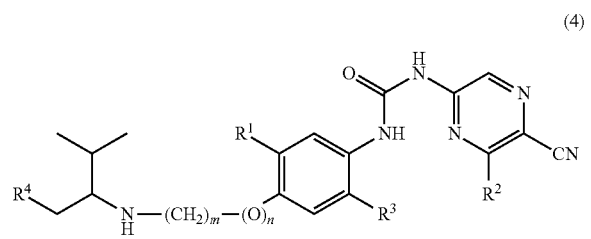

(4)

or a salt, N-oxide or tautomer thereof, wherein:

m is 2, 3 or 4;

n is 0 or 1;

$R^1$ is selected from hydrogen, methyl, chlorine and bromine;

$R^2$ is selected from hydrogen, methyl, methoxy and a group $—(O)_p-Q^2-R^5$;

p is 0 or 1;

$R^3$ is selected from hydrogen, a group $Hyd^1$, a group $—O-Hyd^1$ and a group $—(O)_p-Q^2-R^5$;

provided that when one of $R^2$ and $R^3$ is $—(O)_p-Q^2-R^5$, the other is selected from hydrogen, methoxy and, methyl;

$Hyd^1$ is a non-aromatic $C_{1-6}$ hydrocarbon group;

$R^4$ is selected from amino, $NH-Hyd^2$, $N(Hyd^2)_2$; and a non-aromatic carbocyclic or heterocyclic ring of 4 to 7 ring members containing 0, 1, 2 or 3 heteroatom ring members selected from O, N and S and oxidised forms of N and S; the carbocyclic or heterocyclic ring being optionally substituted with one or two substituents $R^9$;

$Hyd^2$ is an unsubstituted non-aromatic $C_{1-6}$ hydrocarbon group; or a substituted non-aromatic $C_{2-6}$ hydrocarbon group bearing one or two substituents selected from hydroxy and amino;

$Q^2$ is an alkylene chain of 1 to 4 carbon atoms in length wherein one or more of the 1 to 4 carbon atoms of the alkylene chain may optionally be substituted with one or two $C_{1-4}$ alkyl groups and wherein one carbon atom of the 1 to 4 carbon atoms of the alkylene chain may optionally be replaced by a cyclopropane-1,1-diyl or cyclobutane-1,1-diyl group;

$R^5$ is selected from $NR^6R^7$, or $N(O)R^6R^7$ and a cyclic group $R^8$;

$R^6$ and $R^7$ are each independently selected from hydrogen and $C_{1-4}$ alkyl; or $NR^6R^7$ or $N(O)R^6R^7$ form a saturated heterocyclic ring of 4 to 7 ring members optionally containing a second heteroatom ring member selected from O, N and S and oxidised forms of N and S and being optionally substituted with one, two or three substituents selected from oxo, fluorine and methyl;

$R^8$ is a 4- to 8-membered non-aromatic heterocyclic group containing 1 or 2 heteroatom ring members selected from O, N, S and oxidised forms of N and S, wherein the heterocyclic group is optionally substituted with one, two or three substituents selected from oxo, fluorine and methyl; and wherein $R^6$ is attached to $Q^2$ through a carbon atom of the heterocyclic group;

$R^9$ is selected from oxo, halogen, cyano and a group $R^a-R^b$;

$R^a$ is a bond, O, CO, $X^1C(X^2)$, $C(X^2)X^1$, $X^1C(X^2)X^1$, S, SO, $SO_2$, $NR^c$, $SO_2NR^b$ or $NR^cSO_2$;

$R^b$ is:

hydrogen;

a carbocyclic and heterocyclic group having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; and an acyclic $C_{1-6}$ hydrocarbon group optionally substituted with one or more substituents selected from hydroxy; oxo; halogen; cyano; nitro; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; wherein one or two but not all of the carbon atoms of the acyclic $C_{1-6}$ hydrocarbon group may optionally be replaced by O, S, SO, $SO_2$, $NR^c$, $X^1C(X^2)$, $C(X^2)X^1$ or $X^1C(X^2)X^1$;

$R^{10}$ is selected from $R^9$ except that $R^{10}$ does not consist of or contain a cyclic group;

$X^1$ is O, S or $NR^c$; and $X^2$ is $=O$, $=S$ or $=NR^c$; and $R^c$ is hydrogen or $C_{1-4}$ alkyl.

1.122S A compound according to Embodiment 1.22R wherein $R^1$, $R^2$, $R^3$, $R^4$, m and n are as defined in any one of Embodiments 1.2 to 1.121.

1.122T A compound according to Embodiment 1.122R or 1.122S having the formula (4A):

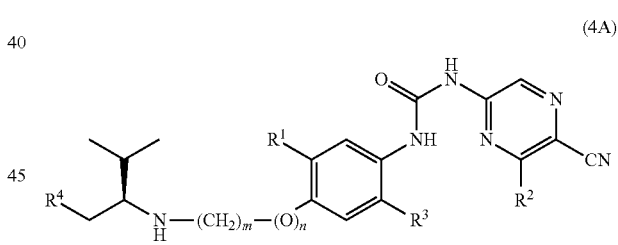

(4A)

or a salt, N-oxide or tautomer thereof.

1.122U A compound according to Embodiment 1.122R or 1.122S having the formula (4B):

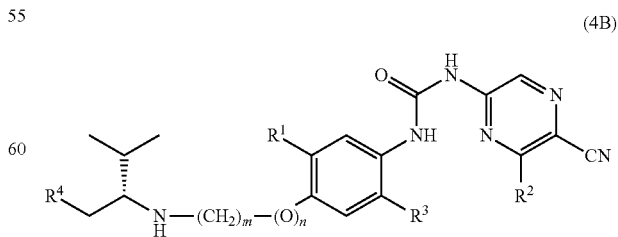

(4B)

or a salt, N-oxide or tautomer thereof.

1.122V A compound according to Embodiment 1.122R which is selected from the title compounds of Examples 31 and 34 below.

1.122W A compound of the formula (5):

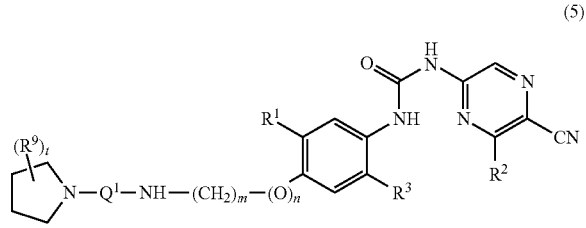

(5)

or a salt, N-oxide or tautomer thereof, wherein:
m is 2, 3 or 4;
n is 0 or 1;
t is 0, 1 or 2;
$Q^1$ is selected from a bond; C(=O); S(O); $SO_2$; and an alkylene chain of 1 to 4 carbon atoms in length between the moiety $R^4$ and the nitrogen atom N, wherein (a) one or more of the 1 to 4 carbon atoms of the alkylene chain may optionally be substituted with one or two $C_1$ alkyl groups; and/or (b) one carbon atom of the 1 to 4 carbon atoms of the alkylene chain may optionally be replaced by a cyclopropane-1,1-diyl group; and/or (c) one carbon atom of the 1 to 4 carbon atoms of the alkylene chain may optionally be replaced by C(=O), S(O), or $SO_2$, provided that contains no more than one C(=O), S(O), or $SO_2$ moiety;
$R^1$ is selected from hydrogen, methyl, chlorine and bromine;
$R^2$ is selected from hydrogen, methyl, methoxy and a group —$(O)_p$-$Q^2$-$R^5$;
p is 0 or 1;
$R^3$ is selected from hydrogen, a group $Hyd^1$, a group —O-$Hyd^1$ and a group —$(O)_p$-$Q^2$-$R^5$;
provided that when one of $R^2$ and $R^3$ is —$(O)_p$-$Q^2$-$R^5$, the other is selected from hydrogen, methoxy and methyl;
$Hyd^1$ is a non-aromatic $C_1$ hydrocarbon group;
$Q^2$ is an alkylene chain of 1 to 4 carbon atoms in length wherein one or more of the 1 to 4 carbon atoms of the alkylene chain may optionally be substituted with one or two $C_{1-4}$ alkyl groups and wherein one carbon atom of the 1 to 4 carbon atoms of the alkylene chain may optionally be replaced by a cyclopropane-1,1-diyl or cyclobutane-1,1-diyl group;
$R^5$ is selected from $NR^6R^7$, or $N(O)R^6R^7$ and a cyclic group $R^8$;
$R^6$ and $R^7$ are each independently selected from hydrogen and $C_{1-4}$ alkyl; or $NR^6R^7$ or $N(O)R^6R^7$ form a saturated heterocyclic ring of 4 to 7 ring members optionally containing a second heteroatom ring member selected from O, N and S and oxidised forms of N and S and being optionally substituted with one, two or three substituents selected from oxo, fluorine and methyl;
$R^8$ is a 4- to 8-membered non-aromatic heterocyclic group containing 1 or 2 heteroatom ring members selected from O, N, S and oxidised forms of N and S, wherein the heterocyclic group is optionally substituted with one, two or three substituents selected from oxo, fluorine and methyl; and wherein $R^8$ is attached to $Q^2$ through a carbon atom of the heterocyclic group;
$R^9$ is selected from oxo, halogen, cyano and a group $R^a$-$R^b$;

$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;
$R^b$ is:
hydrogen;
a carbocyclic and heterocyclic group having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; and
an acyclic $C_{1-6}$ hydrocarbon group optionally substituted with one or more substituents selected from hydroxy; oxo; halogen; cyano; nitro; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of N and S, the carbocyclic or heterocyclic group being optionally substituted with one or more substituents $R^{10}$; wherein one or two but not all of the carbon atoms of the acyclic $C_{1-6}$ hydrocarbon group may optionally be replaced by O, S, SO, $SO_2$, $NR^c$, $X^1C(X^2)$, $C(X^2)X^1$ or $X^1C(X^2)X^1$;
$R^{10}$ is selected from $R^9$ except that $R^{10}$ does not consist of or contain a cyclic group;
$X^1$ is O, S or $NR^c$; and
$X^2$ is =O, =S or =$NR^c$; and
$R^c$ is hydrogen or $C_{1-4}$ alkyl.

1.122X A compound according to Embodiment 1.22W wherein $Q^1$, $R^1$, $R^2$, $R^3$, $R^9$, m and n are as defined in any one of Embodiments 1.2 to 1.121.

1.122Y A compound according to Embodiment 1.122W or 1.122X wherein t is 0.

1.122Z A compound according to Embodiment 1.122W or 1.122X wherein t is 1 and $R^9$ is and oxo group.

1.122ZA A compound according to Embodiment 1.122Z wherein the oxo group is in the 2-position of the pyrrolidine ring.

1.122ZB A compound according to Embodiment 1.122W which is selected from the title compounds of Examples 37, 38 and 40 below.

1.123: A compound according to any one of Embodiments 1.1 to 1.122ZB having a molecular weight of up to 1000.

1.124: A compound according to Embodiment 1.123 having a molecular weight of less than 750.

1.125: A compound according to Embodiment 1.124 having a molecular weight of less than 700.

1.126: A compound according to Embodiment 1.125 having a molecular weight of less than 650.

1.127: A compound according to Embodiment 1.126 having a molecular weight of less than 600 or less than 550.

1.128: A compound according to Embodiment 1.127 having a molecular weight of less than 525, for example, 500 or less.

1.129 A compound according to Embodiment 1.1 which is the title compound of any one of Examples 1 to 12 below.

1.129A A compound according to Embodiment 1.1 which is the title compound of any one of Examples 1 to 40 below.

1.129B A compound according to Embodiment 1.1 which is the title compound of any one of Examples 1 to 34 below.

1.129B A compound according to Embodiment 1.1 which is the title compound of any one of Examples 13 to 34 below.

1.130 A compound according to any one of Embodiments 1.1 to 1.129B which is in the form of a salt.

1.131: A compound according to Embodiment 1.130 wherein the salt is an acid addition salt.

1.132: A compound according to Embodiment 1.130 or Embodiment 1.131 wherein the salt is a pharmaceutically acceptable salt.

DEFINITIONS

In this application, the following definitions apply, unless indicated otherwise.

The term "non-aromatic carbocylic or heterocyclic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of non-aromatic heterocyclic groups include morpholine, thiomorpholine and its S-oxide and S,S-dioxide, piperidine, N-alkyl piperidines, piperidone, pyrrolidine, pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran, imidazoline, imidazolidinone, oxazoline, thiazoline, 2-pyrazoline, pyrazolidine, piperazone, piperazine, and N-alkyl piperazines.

Examples of non-aromatic carbocyclic groups include cycloalkane groups such as cyclohexyl and cyclopentyl, cycloalkenyl groups such as cyclopentenyl, cyclohexenyl, and cycloheptenyl.

Generally by way of example, the hydrocarbon groups can have up to six carbon atoms, unless the context requires otherwise. Within the sub-set of hydrocarbon groups having 1 to 6 carbon atoms, particular examples are $C_{1-4}$ hydrocarbon groups (e.g. $C_{1-3}$ hydrocarbon groups or $C_{1-2}$ hydrocarbon groups), specific examples being any individual value or combination of values selected from $C_1$, $C_2$, $C_3$, $C_4$, $C_5$ and $C_6$.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of alkenyl groups include, but are not limited to, ethenyl(vinyl), 1-propenyl, 2-propenyl(allyl), isopropenyl, butenyl, buta-1,4-dienyl, pentenyl, and hexenyl.

Examples of alkynyl groups include, but are not limited to, ethynyl and 2-propynyl(propargyl) groups.

Examples of cycloalkyl groups are those derived from cyclopropane, cyclobutane, cyclopentane, cyclohexane and cycloheptane.

Examples of cycloalkenyl groups include, but are not limited to, cyclopropenyl, cyclobutenyl, cyclopentenyl, cyclopentadienyl and cyclohexenyl.

Examples of halogen substituents include fluorine, chlorine, bromine and iodine. Fluorine and chlorine are particularly preferred. When attached to a non-aromatic moiety, fluorine is preferred.

The term "non-basic" as unused herein in relation to the moiety $R^4$ means either that $R^4$ contains no primary, secondary or tertiary amines having basic character or that any such amines are bonded to a group such as a carbonyl group (e.g. as in an amide) or sulphonyl group (e.g. as in a sulphonamide) which removes the basic character of the amine.

Salts

The compounds of the invention may be presented in the form of salts.

The salts (as defined in Embodiments 1.130 to 1.132) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.131) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Geometric Isomers and Tautomers

The compounds of the invention may exist in a number of different geometric isomeric, and tautomeric forms and references to the compounds of formula (1) as defined in Embodiments 1.1 to 1.132 include all such forms. For the avoidance of doubt, where a compound can exist in one of several geometric isomeric or tautomeric forms and only one is specifically described or shown, all others are nevertheless embraced by formula (1) or subgroups, subsets, preferences and examples thereof.

Optical Isomers

Where compounds of the formula contain one or more chiral centres, and can exist in the form of two or more optical isomers, references to the compounds include all optical isomeric forms thereof (e.g. enantiomers, epimers and diasteroisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (1) is present as a single optical isomer (e.g. enantiomer or diastereoisomer). In one general embodiment, 99% or more (e.g. substantially all) of the total amount of the compound of the formula (1) may be present as a single optical isomer (e.g. enantiomer or diastereoisomer).

Isotopes

The compounds of the invention as defined in any one of Embodiments 1.1 to 1.132 may contain one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds of the formula (1) as defined in any one of Embodiments 1.1 to 1.132 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn of al., Solid-State Chemistry of Drugs, Second Edition, published by SSCI, Inc of West Lafayette, Ind., USA, 1999, ISBN 0-967-06710-3.

Prodrugs

The compounds of the formula (1) as defined in any one of Embodiments 1.1 to 1.132 may be presented in the form of a pro-drug.

By "prodrugs" is meant for example any compound that is converted in vivo into a biologically active compound of the formula (1), as defined in any one of Embodiments 1.1 to 1.132.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Complexes and Clathrates

Also encompassed by formula (1) or subgroups, subsets, preferences and examples thereof are complexes (e.g. inclusion complexes or clathrates with compounds such as cyclodextrins, or complexes with metals) of the compounds.

Biological Activity

The compounds of the formulae (1) and sub-groups thereof are potent inhibitors of Chk-1 and consequently are expected to be beneficial alone or in combination with various chemotherapeutic agents or radiation for treating a wide spectrum of proliferative disorders.

Preferred compounds of the formula (1) are those compounds that have IC$_{50}$ values of less than 1 µM against Chk-1 kinase (e.g. when determined according to the assays described herein). More preferred compounds are those that have IC$_{50}$ values of less than 0.1 µM against Chk-1 kinase. Particularly preferred compounds are those that have IC$_{50}$ values of less than 0.01 µM against Chk-1 kinase. Still more preferred compounds are those that have IC$_{50}$ values of less than 0.001 µM against Chk-1 kinase.

Accordingly, in further embodiments, the invention provides:

Embodiment 2.1

A compound of the formula (1) as defined in any one of Embodiments 1.1 to 1.132 for use in medicine or therapy.

Embodiment 2.2

A compound of the formula (1) as defined in any one of Embodiments 1.1 to 1.132 for use as a Chk-1 kinase inhibitor.

Embodiment 2.3

A compound of the formula (1) for use as defined in Embodiment 2.2 wherein the compound has an $IC_{50}$ values of less than 1 µM against Chk-1 kinase (e.g. when determined according the assays described herein).

Embodiment 2.4

A compound of the formula (1) for use as defined in Embodiment 2.3 wherein the compound has an $IC_{50}$ value of less than 0.1 µM against Chk-1 kinase.

Embodiment 2.5

A compound of the formula (1) for use as defined in Embodiment 2.3 wherein the compound has an $IC_{50}$ value of less than 0.01 µM against Chk-1 kinase.

Embodiment 2.6

A compound of the formula (1) for use as defined in Embodiment 2.3 wherein the compound has an $IC_{50}$ value of less than 0.001 µM against Chk-1 kinase.

Embodiment 2.7

A compound of the formula (1) as defined in any one of Embodiments 1.1 to 1.132 or 2.3 to 2.6 for use in enhancing a therapeutic effect of radiation therapy or chemotherapy in the treatment of a proliferative disease such as cancer.

Embodiment 2.8

A compound of the formula (1) as defined in any one of Embodiments 1.1 to 1.132 or 2.3 to 2.6 for use in the treatment of a proliferative disease such as cancer.

Embodiment 2.9

The use of a compound of the formula (1) as defined in any one of Embodiments 1.1 to 1.132 or 2.3 to 2.6 for the manufacture of a medicament for enhancing a therapeutic effect of radiation therapy or chemotherapy in the treatment of a proliferative disease such as cancer.

Embodiment 2.10

The use of a compound of the formula (1) as defined in any one of Embodiments 1.1 to 1.132 or 2.3 to 2.6 for the manufacture of a medicament for the treatment of a proliferative disease such as cancer.

Embodiment 2.11

A method for the prophylaxis or treatment of a proliferative disease such as cancer, which method comprises administering to a patient in combination with radiotherapy or chemotherapy a compound of the formula (1) as defined in any one of Embodiments 1.1 to 1.132 or 2.3 to 2.6.

Embodiment 2.12

A method for the prophylaxis or treatment of a proliferative disease such as cancer, which method comprises administering to a patient a compound of the formula (1) as defined in any one of Embodiments 1.1 to 1.132 or 2.3 to 2.6.

Embodiment 2.13

A compound for use, use or method as defined in any one of Embodiments 2.7 to 2.12 wherein the cancer is selected from carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Embodiment 2.14

A compound for use, use or method according to Embodiment 2.13 wherein the cancer is selected from breast cancer, colon cancer, lung cancer, ovarian cancer, pancreatic cancer, prostate cancer, glioma, and leukemia.

It is also envisaged that the Chk-1 inhibitors of the invention may be useful in treating tumours in which there is a defective DNA repair mechanism or a defective cell cycle, for example a cancer in which mutations (e.g. in p53) have led to the G1/S DNA damage checkpoint being lost (seethe introductory section of this application). Accordingly in further embodiments, the invention provides:

Embodiment 2.15

A compound for use, use or method as defined in any one of Embodiments 2.7 to 2.14 wherein the cancer is one which is characterized by a defective DNA repair mechanism or defective cell cycle.

Embodiment 2.16

A compound for use, use or method according to Embodiment 2.15 wherein the cancer is a p53 negative or mutated tumour.

Embodiment 2.17

A compound for use, use or method as defined in any one of Embodiments 2.7 to 2.14 wherein the cancer is an MYC oncogene-driven cancer.

Embodiment 2.18

A compound for use, use or method according to Embodiment 2.16 wherein the MYC oncogene-driven cancer is a B-cell lymphoma, leukemia, neuroblastoma, breast cancer or lung cancer.

Embodiment 2.19

A compound of the formula (1) as defined in any one of Embodiments 1.1 to 1.132 for use in the treatment of a patient suffering from a p53 negative or mutated tumour (e.g. a cancer selected from breast cancer, colon cancer, lung cancer, ovarian cancer, pancreatic cancer, prostate cancer, glioma, and leukemia) in combination with radiotherapy or chemotherapy.

Embodiment 2.20

A compound for use according to any one of Embodiments 2.7 to 2.19 wherein, in addition to administration of a compound of the formula (1) as defined in any one of Embodiments 1.1 to 1.132, the treatment comprises administration to a patient of a chemotherapeutic agent selected from cytarabine, etoposide, gemcitabine and SN-38.

Embodiment 2.21

The use of a compound of the formula (1) as defined in any one of Embodiments 1.1 to 1.132 or 2.3 to 2.6 for the manufacture of a medicament for the treatment of a patient suffering from a cancer which is characterised by a defective DNA repair mechanism or defective cell cycle.

Embodiment 2.22

The use according to Embodiment 2.21 wherein the cancer is a p53 negative or mutated tumour.

Embodiment 2.23

A method for the treatment of a patient (e.g. a human patient) suffering from a cancer which is characterised by a defective DNA repair mechanism or defective cell cycle, which method comprises administering to the patient a therapeutically effective amount of a compound of the formula (1) as defined in any one of Embodiments 1.1 to 1.132 or 2.3 to 2.6.

Embodiment 2.24

A method according to Embodiment 2.23 wherein the cancer is a p53 negative or mutated tumour.

The Chk-1 inhibitor compounds of the invention may be used alone or they may be used in combination with DNA-damaging anti-cancer drugs and/or radiation therapy to treat subjects with multi-drug resistant cancers. A cancer is considered to be resistant to a drug when it resumes a normal rate of tumour growth while undergoing treatment with the drug after the tumour had initially responded to the drug. A tumour is considered to "respond to a drug" when it exhibits a decrease in tumor mass or a decrease in the rate of tumour growth.

Methods for the Preparation of Compounds of the Formula (1)

Compounds of the formula (1) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.132, which process comprises:

(A) the reaction of a compound of formula (11):

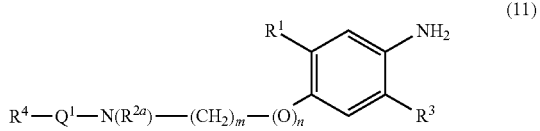

or a protected form thereof, wherein $R^1$, $R^3$ and $R^4$, m and n are as herein before defined and $R^2$ is a $C_{1-4}$ alkyl group or a protecting group PG; with a compound of the formula (12):

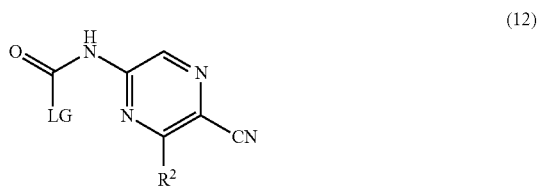

wherein LG is a leaving group such as phenoxy; and thereafter removing any protecting group present; or (B) the reaction of a compound of the formula (11) with a compound of the formula (13):

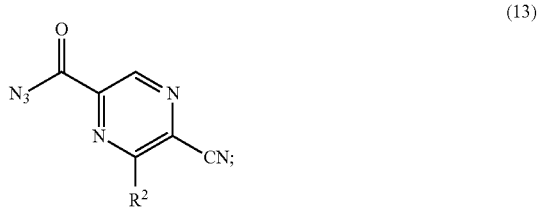

or (C) the reaction of a compound of the formula (11) with a compound of the formula (14):

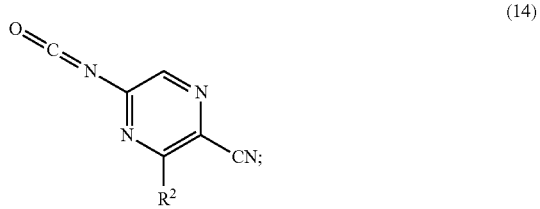

and thereafter optionally converting one compound of the formula (1), into another compound of the formula (1).

In formula (11), the protecting group PG (when present) is a group capable of protecting the amino function against unwanted side reactions and examples of such protecting groups are well known to the skilled person, see the reference book (*Protective Groups in Organic Synthesis* (Greene and Wuts) referred to below.

A particularly preferred protecting group PG is the tert-butoxycarbonyl (Boc) group. The Boc group may readily be removed when required by treatment with an acid such as hydrochloric acid or trifluoroacetic acid.

In process variant (A), the leaving group LG can be a halogen such as chlorine or, more preferably, a phenoxy group or substituted phenoxy group such as a para-nitrophenoxy group.

The reaction between a compound of the formula (11) and a compound of the formula (12) where LG is phenoxy is typically carried out with heating (e.g. to a temperature of 80-100° C.) in a polar non-protic solvent such as dimethylformamide.

Compounds of the formula (12) can be prepared by the reaction of a compound of the formula (15):

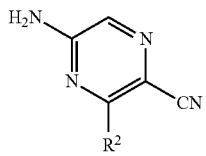
(15)

with phenyl chloroformate. The reaction is typically carried out with heating (for example to a temperature of 40-60° C.) in a non-protic solvent such as dichloromethane or tetrahydrofuran or mixtures thereof, in the presence of a non-interfering base such as pyridine.

Compounds of the formula (13) can be prepared from the corresponding carboxylic acid of the formula (13A):

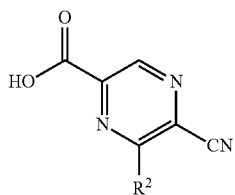
(13A)

by reaction with diphenylphosphorylazide in a polar non-protic solvent such as tetrahydrofuran (THF) in the presence of a non-interfering base such as triethylamine. The reaction is typically carried out at room temperature.

Alternatively, the azide can be made by forming an acid chloride of the carboxylic acid, and reacting the acid chloride with sodium azide.

Compounds of the formula (14) can be prepared by thermal decomposition of compounds of the formula (13) under Curtius conditions.

Compounds of the formula (11) can be prepared by the reduction of a nitro-compound of the formula (16):

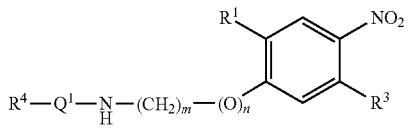
(16)

using conditions suitable for reducing a nitro group to an amino group. Reduction of the nitro group can be carried out, for example, using a metal such as zinc powder in the presence of an acid (e.g. a weak acid such as ammonium chloride), or by catalytic hydrogenation over a metal catalyst such as platinum oxide or Raney nickel, or by use of a reducing agent such as an alkali metal dithionite (e.g. sodium dithionite). The skilled person will be well aware of the types of reagents and conditions required for the reduction of the nitro group.

The nitro compounds of the formula (16) can be prepared by various synthetic routes depending on the nature of the elements $Q^1$, $R^1$, $R^3$, $R^4$, m and n.

For example, compounds wherein n is 0 can be prepared by a reductive amination reaction between a compound of the formula (17):

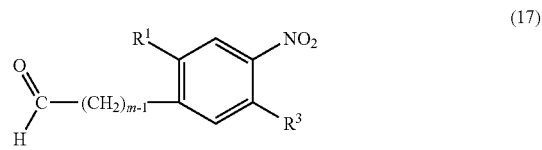
(17)

and a compound of the formula (18):

$R^4$-$Q^1$-$NH_2$     (18)

The reductive amination reaction may be carried out using a boron hydride reducing agent such as sodium borohydride or $NaB(OAc)_3H$ in accordance with known methods.

Compounds of the formula (17) can be prepared by the sequence of reactions shown in Scheme 1 below.

Scheme 1

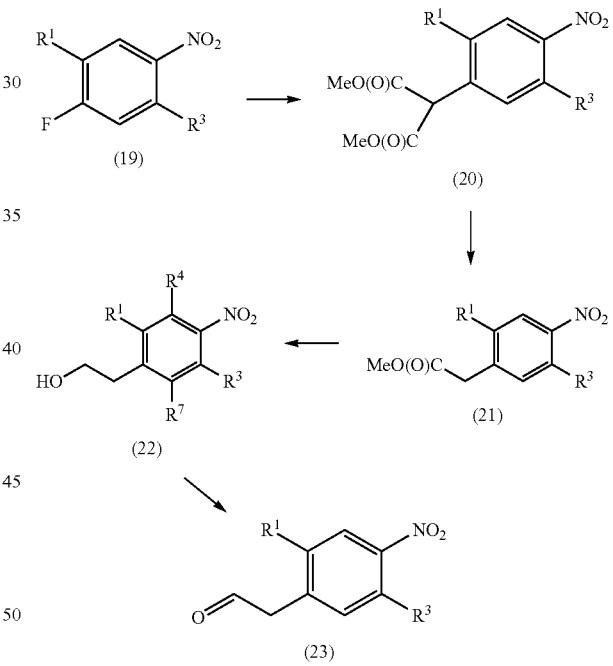

In Scheme 1, the nitro-fluorobenzene (19) is reacted with dimethylmalonate in a polar solvent such as N-methylpyrrolidone in the presence of a base such as sodium hydroxide, usually with heating (for example to a temperature of 70-90° C.), to give the substituted malonic ester (20). The substituted malonic ester (20) may then be subjected to a monohydrolysis/decarboxylation step to give the substituted nitrophenylacetic acid ester (21) by heating in an aqueous DMSO solution containing sodium chloride at a temperature in the range 100-115° C.

The substituted nitrophenylacetic acid ester (21) can be reduced to the alcohol (22) using a boron hydride reagent such as lithium borohydride in a dry polar aprotic solvent such as THF. The alcohol (22) may then be oxidised to the aldehyde (23) using Dess Martin periodinane in a chlorinated solvent such as dichloromethane.

In a variation of the above procedure, the alcohol (22) can be converted to the corresponding bromo compound (24):

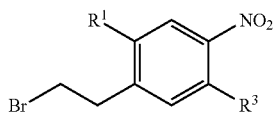
(24)

by reaction with PBr$_3$ in a solvent such as an ether, according to methods well known to the skilled person. Alternatively, the bromo compound (24) can be prepared from the alcohol (22) by reaction with bromine and triphenylphosphine.

The bromo compound (24) can be reacted with the amine (18) to give a compound of formula (16).

Compounds of the formula (16), wherein n is 1 can be prepared by the reaction of a compound of the formula (25):

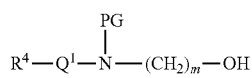
(25)

with a compound of the formula (19) (see Scheme 1 for structure of compound (19). The reaction is typically carried out by first reacting the compound of formula (25) with sodium hydride to form an alcoholate anion and then adding the compound of formula (20). The reactions may be conducted in a polar aprotic solvent such as dimethylformamide.

Compounds of formula (19) can be obtained commercially or by using standard synthetic methods well known to the skilled person or analogous thereto, see for example *Advanced Organic Chemistry* by Jerry March, 4$^{th}$ Edition, John Wiley & Sons, 1992, and and *Organic Syntheses*, Volumes 1-8, John Wiley, edited by Jeremiah P. Freeman (ISBN: 0-471-31192-8), 1995, and see also the methods described in the experimental section below.

Compounds of the formula (16) can also be prepared by the reductive amination reaction of an aldehyde compound of the formula (26), where Q$^{1'}$ is an alkylene chain of 1 to 3 carbon atoms in length, and an amino compound of the formula (27):

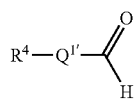
(26)

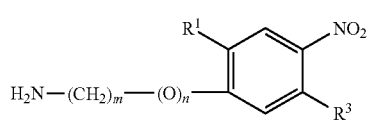
(27)

followed by the reaction of the product with a reagent (such as di-tert-butyl-carbonate) suitable for introducing the protecting group PG. The reductive amination step will typically employ a borohydride reducing agent such as NaB(OAc)$_3$H as described above.

Compounds of the formula (16) wherein n is 0 and m is 2 can be prepared by the reaction of a compound of the formula (28):

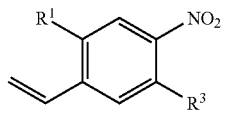
(28)

and a compound of the formula (18) in the presence of hydroquinone (quinol). The reaction may be carried out in an alcoholic solvent such as isopropyl alcohol or n-butanol, typically with heating to a temperature of about 80-90° C.

Compounds of the formula (28) can be prepared by the reaction of a compound of the formula (29):

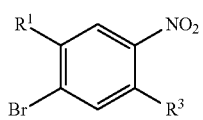
(29)

with potassium ethenyl(trifluoro)borate in the presence of a non-interfering base such as triethylamine and a palladium catalyst such as PdCl$_2$ (1,1'-bis(diphenylphosphino)-ferrocene).

Intermediates of the formula (12) wherein R$^2$ is a group —(O)$_p$-Q$^2$-R$^5$ wherein p is 1 can be prepared by the sequence of reactions set out in Scheme 2 or methods analogous thereto.

Scheme 2

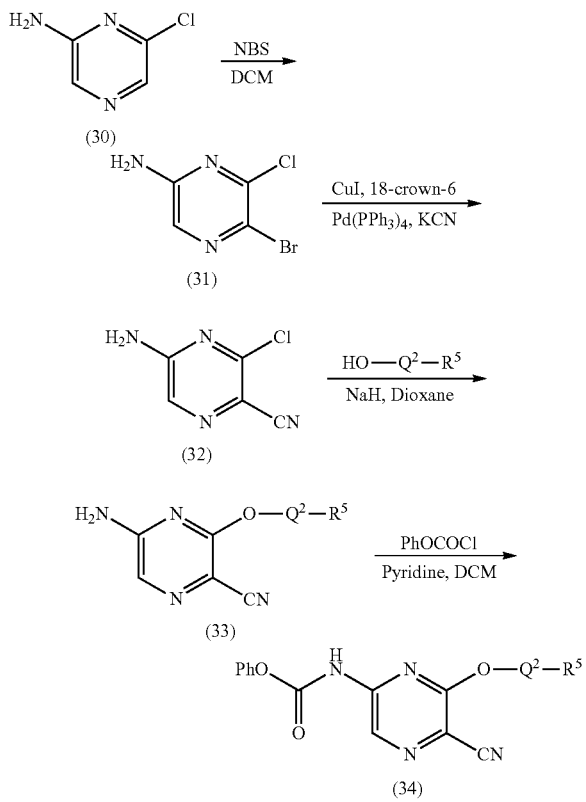

In Scheme 2, the amino-chloro-pyrazine is brominated using N-bromosuccinimide (NBS) in dichloromethane to give the bromo-pyrazine (31) which is then converted to the nitrile (32). The nitrile is reacted with HO-Q$^2$-R$^5$ in the presence of sodium hydride to give the amine (33) which is then converted to the carbamate (34) by reaction with phenyl chloroformate in the presence of a non-interfering base such as pyridine.

Compounds of the formula (16) wherein n is 1 and m is 2 can be prepared by the reaction of a compound of the formula (35):

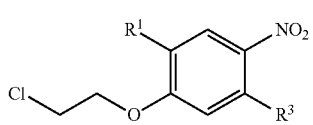

(35)

with an amine compound of the formula (18). The reaction is typically carried out in the presence of a non-interfering base such as triethylamine in a polar solvent such as acetonitrile, usually with moderate heating, for example to a temperature in the range from about 60° C. to 100° C., e.g. around 70° C. Compounds of the formula (35) can be prepared by nitration of a compound of formula (36):

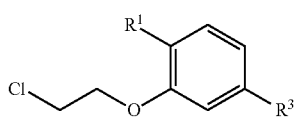

(36)

for example, using a nitrating mixture comprising tetrabutylammonium nitrate, trifluoroacetic anhydride and a crown ether such as 18-crown-6 in an aprotic solvent such as dichloromethane. The reaction is typically carried out at temperatures of less than 0° C., for example at a temperature of about −10° C. Compounds of formula can be prepared as described in the Examples below (see the reaction scheme for Example 25) or methods analogous thereto, or by known methods.

Compounds of the formula (16) wherein Q$^1$ is C(=O) can be prepared by reacting an amine compound of the formula (27) with a carboxylic acid R$^4$—CO$_2$H or an activated derivative thereof such as an acid chloride. The reaction of the amine of formula (27) with the carboxylic acid R$^4$—CO$_2$H can be carried out in the presence of a reagent of the type commonly used in the formation of peptide linkages. Examples of such reagents include 1,3-dicyclohexylcarbodiimide (DCC) (Sheehan et al, *J. Amer. Chem Soc.* 1955, 77, 1067), 1-ethyl-3-(3'-dimethylaminopropyl)-carbodiimide (referred to herein either as EDC or EDAC) (Sheehan et al, *J. Org. Chem.*, 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include HATU, or EDC (EDAC) and DCC in combination with HOAt or HOBt.

The coupling reaction is typically carried out in a non-aqueous, non-protic solvent such as acetonitrile, dioxane, dimethylsulphoxide, dichloromethane, dimethylformamide or N-methylpyrrolidinone, or in an aqueous solvent optionally together with one or more miscible co-solvents. The reaction can be carried out at room temperature, typically in the presence of a non-interfering base, for example a tertiary amine such as triethylamine or N,N-diisopropylethylamine.

Compounds of the formula (16) wherein the group R$^4$-Q$^1$-NH— is R$^4$-Q$^{1a}$-C(=O)—NH—, where Q$^{1a}$ is the residue of Q$^1$ minus one carbon atom, can be prepared by reacting an amine compound of the formula (27) with a chloro-alkanoyl chloride Cl-Q$^{1a}$-C(=O)—Cl, where to give an intermediate compound of the formula (37):

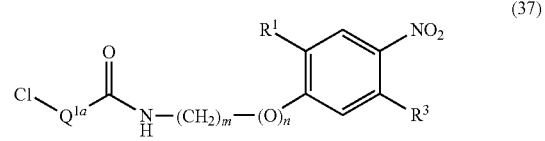

(37)

followed by reaction of the compound of formula (37) with a compound R$^4$—H where R$^4$ is an amino or cyclic amino group such as a piperazine, piperidine, morpholine or pyrrolidine group. The reaction of the amino compound (27) with the chloro-alkanoyl chloride Cl-Q$^{10}$-C(=O)—Cl (e.g. chloroacetyl chloride) is typically carried out at low temperature (e.g. around 0° C.) in an aprotic solvent such as dichloromethane in the presence of a non-interfering base such as triethylamine. The subsequent reaction of the compound of formula (37) with the compound R$^4$—H can be carried out in a polar aprotic solvent such as acetonitrile in the presence of a base such as potassium carbonate at a moderately elevated temperature, for example in the range from about 60° C. to 100° C., e.g around 70° C.

Compounds of the formula (16) wherein n is 0 and the group R$^4$-Q$^1$-NH— is R$^4$—C(=O)-Q$^{1a}$-NH—, where Q$^{1a}$ is the residue of Q$^1$ minus one carbon atom, can be prepared by reacting a styrene compound of the formula (28) with an amine of the formula R$^4$—C(=O)-Q$^{1a}$-NH$_2$ in the presence of hydroquinone under the conditions described in Example 1 below or conditions analogous thereto.

Many amines of the formula R$^4$—C(=O)-Q$^{1a}$-NH$_2$ are commercially available. Other can be made by the coupling of R$^4$H with a suitably N-protected amino acid HO—C(=O)-Q$^{1a}$-NH-PG (e.g. Boc-alanine) or an activated derivative thereof such as an acid chloride followed by the removal of the protecting group. The reaction of the amine R$^4$H with the N-protected amino acid HO—C(=O)-Q$^{1a}$-NHPG can be carried out in the presence of a reagent of the type commonly used in the formation of peptide linkages as described above.

Once formed, one compound of the formula (1), or a protected derivative thereof, can be converted into another compound of the formula (I) by methods well known to the skilled person. Examples of synthetic procedures for converting one functional group into another functional group are set out in standard texts such as *Advanced Organic Chemistry* and *Organic Syntheses* (see references above) or *Fiesers' Reagents for Organic Synthesis*, Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.1 to 1.132 together with a pharmaceutically acceptable excipient.

The pharmaceutically acceptable excipient can be, for example, a carrier (e.g. a solid, liquid or semi-solid carrier), a diluent or bulking agent, a granulating agent, coating agent, binding agent, disintegrant, lubricating agent, preservative, antioxidant, buffering agent, suspending agent, thickening agent, flavouring agent, sweetener, taste masking agent or any other excipient conventionally used in pharmaceutical compositions. Examples of excipients for various types of pharmaceutical compositions are set out in more detail below.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (1) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; poly-alcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastro-intestinal tract. As a further alternative, the active compound can be formulated in a delivery system that provides osmotic control of the release of the compound. Osmotic release and other delayed release or sustained release formulations may be prepared in accordance with methods well known to those skilled in the art.

The compound of formula (1), as defined in any one of Embodiments 1.1 to 1.132, or a prodrug thereof, may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of the formula (1) as defined in any one of Embodiments 1.1 to 1.132 as defined herein will be useful either alone or in combination therapy with chemotherapeutic agents (particularly DNA-damaging agents) or radiation therapy in the prophylaxis or treatment of a range of proliferative disease states or conditions. Examples of such disease states and conditions are set out above.

The compounds of formula (1), whether administered alone, or in combination with DNA damaging agents and other anti-cancer agents and therapies, are generally administered to a subject in need of such administration, for example a human or animal patient, preferably a human.

Examples of chemotherapeutic agents that may be co-administered with the compounds of formula (1) as defined in any one of Embodiments 1.1 to 1.132 include:
Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Hypoxia triggered DNA damaging agents (e.g. Tirapazamine)

Particular examples of chemotherapeutic agents that may be administered in combination with the compounds of formula (1) as defined in any one of Embodiments 1.1 to 1.132 include:
nitrogen mustards such as mechlorethamine, cyclophosphamide, ifosfamide, melphalan and chlorambucil;
nitrosoureas such as carmustine, lomustine and semustine;
ethyleneimine/methylmelamine compounds such as triethylenemelamine, triethylene thiophosphoramide and hexamethylmelamine;
alkyl sulphonates such as busulfan;
triazines such as dacarbazine
Antimetabolites such as folates, methotrexate, trimetrexate, 5-fluorouracil, fluorodeoxyuridine, gemcitabine, cytosine arabinoside, 5-azacytidine, 2,2'-difluorodeoxycytidine, 6-mercaptopurine, 6-thioguanine, azathioprine, 2'-deoxycoformycin, erythrohydroxynonyl-adenine, fludarabine phosphate and 2-chlorodeoxyadenosine;
type I topoisomerase inhibitors such as camptothecin, topotecan and irinotecan;
type II topoisomerase inhibitors such as the epipodophylotoxins (e.g. etoposide and teniposide);
antimitotic drugs such as paclitaxel, Taxotere, Vinca alkaloids (e.g. vinblastine, vincristine, vinorelbine) and estramustine (e.g. estramustine phosphate);
antibiotics such as actinomycin D, daunomycin (rubidomycin), doxorubicin (adriamycin), mitoxantrone, idarubicine, bleomycin, mithramycin, mitomycin C and dactinomycin enzymes such as L-asparaginase;
cytokines and biological response modifiers such as interferon ($\alpha$, $\beta$, $\gamma$), interleukin-2G-CSF and GM-CSF:
retinoids such as retinoic acid derivatives (e.g. bexarotene);
radiosensitisers such as metronidazole, misonidazole, desmethylmisonidazole, pimonidazole, etanidazole, nimorazole, nicotinamide, 5-bromodeoxyuridine, 5-iododeoxyuridine and bromodeoxycytidine;
platinum compounds such as cisplatin, carboplatin, spiroplatin, iproplatin, onnaplatin, tetraplatin and oxaliplatin;
anthracenediones such as mitoxantrone;
ureas such as hydroxyurea;
hydrazine derivatives such as N-methylhydrazine and procarbazine;
adrenocortical suppressants such as mitotane and aminoglutethimide;
adrenocorticosteroids and antagonists such as prednisone, dexamethasone and aminoglutethimide;
progestins such as hydroxyprogesterone (e.g. hydroxyprogesterone caproate), medroxyprogesterone (e.g. medroxyprogesterone acetate) and megestrol (e.g. megestrol acetate);
oestrogens such as diethylstilbestrol and ethynyl estradiol;
anti-oestrogens such as tamoxifen;
androgens such as testosterone (e.g. testosterone propionate) and fluoxymesterone;
anti-androgens such as flutamide and leuprolide;
nonsteroidal anti-androgens such as flutamide; and
signal transduction inhibitors such as PARP inhibitors [e.g. as disclosed in *Cancer Res.;* 66: (16)], Mek inhibitors [e.g as disclosed in *Blood.* 2008 Sep. 15; 112(6): 2439-2449], farnesyltransferase inhibitors [e.g. as disclosed in *Blood.* 2005 Feb. 15; 105(4):1706-16], rapamycin and Src inhibitors [e.g as disclosed in *Blood.* 2011 Feb. 10; 117(6): 1947-57].

Examples of the chemotherapeutic agents than may be used in combination with the Chk-1 inhibitor compounds of Embodiments 1.1 to 1.132 as defined herein include the chemotherapeutic agents described in Blasina et al., Mol. Cancer Ther., 2008, 7(8), 2394-2404, Ashwell et al., Clin. Cancer Res., 2008, 14(13), 4032-4037, Ashwell et al., Expert Opin. Investig. Drugs, 2008, 17(9), 1331-1340, Trends in Molecular Medicine February 2011, Vol. 17, No. 2 and Clin Cancer Res; 16(2) Jan. 15, 2010.

Particular examples of chemotherapeutic agents that may be used in combination with the Chk-1 inhibitor compounds of Embodiments 1.1 to 1.132 as defined herein include antimetabolites (such as gemcitabine and cytarabine), Topoisomerase-I inhibitors (such as SN38, topotecan, irinotecan), platinum compounds (such as carboplatin and cisplatin), Topoisomerase-II inhibitors (such as doxorubicin and etoposide), thymidylate synthase inhibitors (such as 5-fluoruracil), mitotic inhibitors (such as paclitaxel) and alkylating agents (such as mitomycin C).

A further set of chemotherapeutic agents that may be used in combination with the Chk-1 inhibitor compounds of Embodiments 1.1 to 1.132 as defined herein includes agents that induce stalled replication forks (see Ashwell et al., Clin. Cancer Res., above), and examples of such compounds include gemcitabine, 5-fluorouracil and hydroxyurea.

The compounds of the invention and combinations with chemotherapeutic agents or radiation therapies as described above may be administered over a prolonged term to maintain beneficial therapeutic effects or may be administered for a short period only. Alternatively they may be administered in a pulsatile or continuous manner.

The compounds of the invention will be administered in an effective amount, i.e. an amount which is effective to bring about the desired therapeutic effect either alone (in monotherapy) or in combination with one or more chemotherapeutic agents or radiation therapy. For example, the "effective amount" can be a quantity of compound which, when administered alone or together with a DNA-damaging drug or other anti-cancer drug to a subject suffering from cancer, slows tumour growth, ameliorates the symptoms of the disease and/or increases longevity. More particularly, when used in combination with radiation therapy, with a DNA-damaging drug or other anti-cancer drug, an effective amount of the Chk-1 inhibitor of the invention is the quantity in which a greater response is achieved when the Chk-1 inhibitor is co-administered with the DNA damaging anti-cancer drug and/or radiation therapy compared with when the DNA damaging anti-cancer drug and/or radiation therapy is administered alone. When used as a combination therapy, an "effective amount" of the DNA damaging drug and/or an "effective" radiation dose are administered to the subject, which is a quantity in which anti-cancer effects are normally achieved. The Chk-1 inhibitors of the invention and the DNA damaging anti-cancer drug can be co-administered to the subject as part of the same pharmaceutical composition or, alternatively, as separate pharmaceutical compositions.

When administered as separate pharmaceutical compositions, the Chk-1 inhibitor of the invention and the DNA-damaging anti-cancer drug (and/or radiation therapy) can be administered simultaneously or at different times, provided that the enhancing effect of the Chk-1 inhibitor is retained.

In one embodiment; a compound of any one of Embodiments 1.1 to 1.132 as defined herein is administered before (e.g by up to 8 hours or up to 12 hours or up to one day before) administration of the DNA-damaging anticancer drug.

In another embodiment, a compound of any one of Embodiments 1.1 to 1.132 as defined herein is administered after (e.g by up to 8 hours or up to 12 hours or up to 24 hours or up to 30 hours or up to 48 hours after) administration of the DNA-damaging anticancer drug. In another embodiment, a first dose of a compound of any one of Embodiments 1.1 to 1.132 as defined herein is administered one day after administration of the DNA-damaging anticancer drug and a second dose of the said compound is administered two days after administration of the DNA-damaging anticancer drug.

In a further embodiment, a first dose of a compound of any one of Embodiments 1.1 to 1.132 as defined herein is administered one day after administration of the DNA-damaging anticancer drug, a second dose of the said compound is administered two days after administration of the DNA-damaging anticancer drug, and third dose of the said compound is administered three days after administration of the DNA-damaging anticancer drug.

Particular dosage regimes comprising the administration of a compound of any one of Embodiments 1.1 to 1.132 as defined herein and a DNA-damaging anticancer drug may be as set out in WO2010/118390 (Array Biopharma), the contents of which are incorporated herein by reference.

The amount of Chk-1 inhibitor compound of the invention and (in the case of combination therapy) the DNA damaging anti-cancer drug and radiation dose administered to the subject will depend on the nature and potency of the DNA damaging anti-cancer drug, the type and severity of the disease or condition and on the characteristics of the subject, such as general health, age, sex, body weight and tolerance to drugs. The skilled person will be able to determine appropriate dosages depending on these and other factors. Effective dosages for commonly used anti-cancer drugs and radiation therapy are well known to the skilled person.

A typical daily dose of the compound of formula (1), whether administered on its own in monotherapy or administered in combination with a DNA damaging anticancer drug, can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

Ultimately, however, the quantity of compound administered and the type of composition used will be commensurate with the nature of the disease or physiological condition being treated and will be at the discretion of the physician.

Methods of Diagnosis

Prior to administration of a compound of the formula (1) as defined in any one of Embodiments 1.1 to 1.132, a patient may be screened to determine whether a cancer from which the patient is or may be suffering is one which would be susceptible to treatment with either a Chk-1 kinase inhibitor compound or a combination of a chemotherapeutic agent (such as a DNA-damaging agent) and a Chk-1 kinase inhibitor compound.

More particularly, a patient may be screened to determine whether a cancer from which the patient is or may be suffering is one which is characterised by a defective DNA repair mechanism or a defective cell cycle, for example a defective cell cycle due to a p53 mutation or is a p53 negative cancer.

Cancers which are characterised by p53 mutations or the absence of p53 can be identified, for example, by the methods described in Allred et al., J. Nat. Cancer Institute, Vol. 85, No. 3, 200-206 (1993) and the methods described in the articles listed in the introductory part of this application. For example, p53 protein may be detected by immuno-histochemical methods such as immuno-staining.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

Thus, the compounds of any one of Embodiments 1.1 to 1.132 may be used to treat members of a sub-population of patients who have been screened (for example by testing one or more biological samples taken from the said patients) and have been found to be suffering from a cancer characterised by p53 mutation or a p53 negative cancer.

EXAMPLES

The invention will now be illustrated, but not limited, by reference to the specific embodiments described in the following examples.

In the examples, the following abbreviations are used.
Boc₂O di-tert-butyl dicarbonate
DCM dichloromethane
DIPEA diisopropylethylamine
DMF dimethylformamide
DMSO dimethylsulphoxide
EtOAc ethyl acetate
HCl hydrogen chloride
HPLC high performance liquid chromatography
IPA isopropyl alcohol
LCMS liquid chromatography-mass spectrometry
MeCN acetonitrile
MeOH methanol
Na₂SO₄ sodium sulfate
NH₃ ammonia
NH₄Cl ammonium chloride
NMR nuclear magnetic resonance
TFA trifluoroacetic acid
THF tetrahydrofuran Proton magnetic resonance ($^1$H NMR) spectra were recorded on a Bruker 400 instrument operating at 400 MHz, in DMSO-$d_6$ or MeOH-$d_4$ (as indicated) at 27° C., unless otherwise stated and are reported as follows: chemical shift δ/ppm (multiplicity where s=singlet, d=doublet, t=triplet, q=quartet, m=multiplet, br=broad, number of protons). The residual protic solvent was used as the internal reference.

Liquid chromatography and mass spectroscopy analyses were carried out using the system and operating conditions set out below. Where atoms with different isotopes are present and a single mass quoted, the mass quoted for the compound is the monoisotopic mass (i.e. $^{35}$Cl; $^{79}$Br etc.)

Analytical HPLC/MS Conditions

The LCMS data given in the following examples were obtained using one of Methods B, C, D, E or F below or, where stated, Method A below LCMS Method A Samples were analysed by reverse phase HPLC-MS using a Waters 2795 Alliance HT HPLC, a Micromass ZQ mass spectrometer and a Waters 996 photodiode array UV detector. The LCMS used electrospray ionisation and one of six different chromatography systems, as follows:

| Mass Spectrometer: | | |
|---|---|---|
| Ionization mode: | Positive | Negative |
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| Interscan delay: | 0.20 seconds | 0.20 seconds |
| Mass range: | 80 to 1000 AMU | 80 to 1000 AMU |

LCMS was carried out using an ACE 3 C18 50×4.6 mm, 3 micron column at 211 nm. Column flow was 1 mL/min and the solvents used were 0.1% formic acid in water (A) and 0.1% formic acid in acetonitrile (B), with an injection volume of 10 μL.

| Time (min) | % A | % B |
|---|---|---|
| 0.01 | 90 | 10 |
| 3.00 | 10 | 90 |
| 5.00 | 0 | 100 |
| 6.00 | 0 | 100 |
| 6.01 | 90 | 10 |
| 7.00 | 90 | 10 |

LCMS Method B

LCMS was carried out using a XBridge C18 150×4.6 mm, 5 micron column at 211 nm and 264 nm. Column flow was 1 mL/min and the solvents used were 0.1% ammonium solution in water (A) and 0.1% ammonium solution in acetonitrile (B) with an injection volume of 10 μL.

| Time (min) | % A | % B |
|---|---|---|
| 0.01 | 90 | 10 |
| 5.00 | 10 | 90 |
| 7.00 | 0 | 100 |
| 11.00 | 0 | 100 |
| 11.01 | 90 | 10 |
| 12.00 | 90 | 10 |

LCMS Method C

LCMS was carried out using a X-Bridge C18 150×4.6 mm, 5 micron column at 211 nm. Column flow was 1 mL/min and the solvents used were 0.1% ammonium solution in water (A) and 0.1% ammonium solution in acetonitrile (B) with an injection volume of 20 μL.

| Time (min) | % A | % B |
|---|---|---|
| 0.01 | 90 | 10 |
| 3.00 | 10 | 90 |
| 5.00 | 0 | 100 |
| 6.00 | 0 | 100 |
| 6.01 | 90 | 10 |
| 7.00 | 90 | 10 |

LCMS Method D

LCMS was carried out using an AQUITY UPLC BEH C18 50×2.1 mm, 1.7 micron column at 211 nm. Column flow was 0.4 mL/min and the solvents used were 0.1% formic acid in water (A) and 0.1% formic acid in acetonitrile (B), with an injection volume of 1 μL.

| Time (min) | % A | % B |
|---|---|---|
| 0.01 | 90 | 10 |
| 2.50 | 10 | 90 |
| 3.50 | 0 | 100 |
| 4.50 | 0 | 100 |
| 4.60 | 90 | 10 |
| 5.00 | 90 | 10 |

LCMS Method E

LCMS was carried out using an ACE 3 50×4.6 mm, 3 micron column at 211 nm. Column flow was 1 mL/min and the solvents used were 0.1% ammonium solution in water (A) and 0.1% ammonium solution in acetonitrile (B) with an injection volume of 30 μL.

| Time (min) | % A | % B |
|---|---|---|
| 0.01 | 90 | 10 |
| 3.00 | 10 | 90 |
| 5.00 | 0 | 100 |

-continued

| Time (min) | % A | % B |
|---|---|---|
| 6.00 | 0 | 100 |
| 6.01 | 90 | 10 |
| 7.00 | 90 | 10 |

LCMS Method F

LCMS was carried out using a BEH C18 50×2.1 mm, 1.7 micron column at 242 nm. Column flow was 0.4 mL/min and solvents used were 0.1% ammonia in water (A) and 0.1% ammonia in acetonitrile (B) with an injection volume of 1 µL.

| Time (min) | % A | % B |
|---|---|---|
| 0.01 | 90 | 10 |
| 2.50 | 10 | 90 |
| 3.50 | 0 | 100 |
| 4.50 | 0 | 100 |
| 4.60 | 90 | 10 |
| 5.00 | 90 | 10 |

LCMS Method G

LC-MS was carried out on BEH C18 50×2.1 mm, 1.7 micron at 241 nm. Column flow was 0.4 ml/min and mobile phase were used (A) 0.1% formic acid+5 millimolar ammonium acetate in water and (B) 0.1% formic acid in acetonitrile with an injection volume of 2 µL.

Gradient was as described below.

LC (method) RT=2.593 min.

| Time (min) | % A | % B |
|---|---|---|
| 0.01 | 95 | 05 |
| 0.70 | 95 | 05 |
| 1.90 | 35 | 65 |
| 2.50 | 10 | 90 |
| 3.50 | 0 | 100 |
| 5.00 | 0 | 100 |
| 5.01 | 95 | 05 |
| 6.00 | 95 | 05 |

Analytical HPLC Conditions

The HPLC data given in the following examples were obtained using the Method A below HPLC Method A HPLC was carried out using a Sunfire C18-250*4.6*5u column at 253 nm. Column flow was 1 mL/min and the solvents used were 0.1% formic acid in water (A) and 0.1% formic acid in acetonitrile (B) with an injection volume of 20 µL.

| Time (min) | % A | % B |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 25.00 | 90 | 10 |

Examples 1 to 40

The compounds of Examples 1 to 40 shown in Table 1 below have either been prepared or can be prepared by the methods described herein or methods analogous thereto. Their NMR, HPLC and LCMS properties and methods for their preparation are set out in Table 2.

TABLE 1

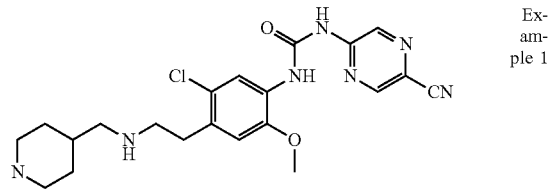

Example 1

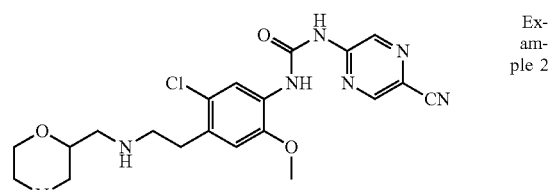

Example 2

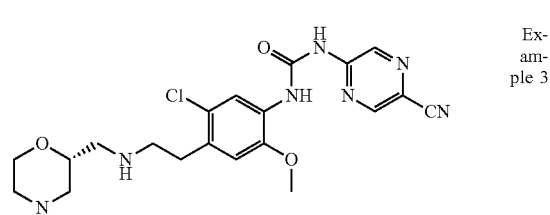

Example 3

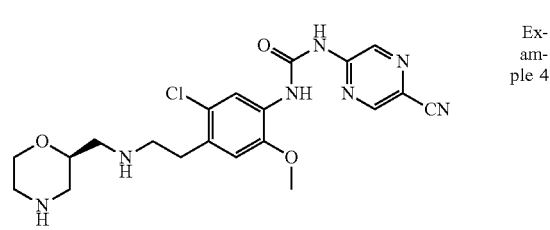

Example 4

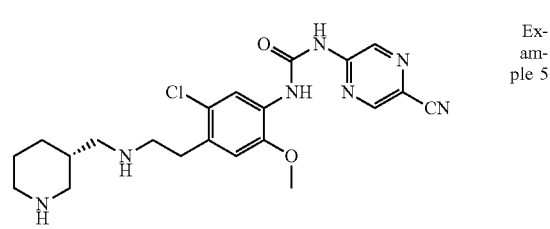

Example 5

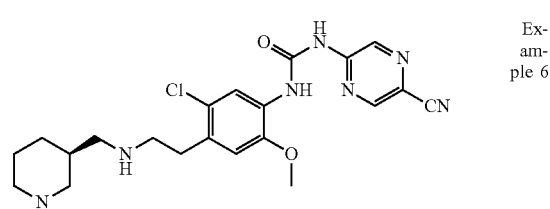

Example 6

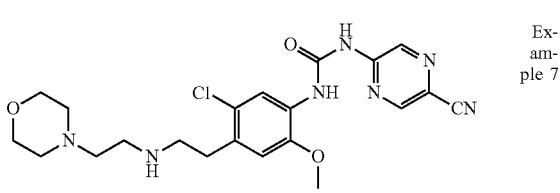

Example 7

TABLE 1-continued
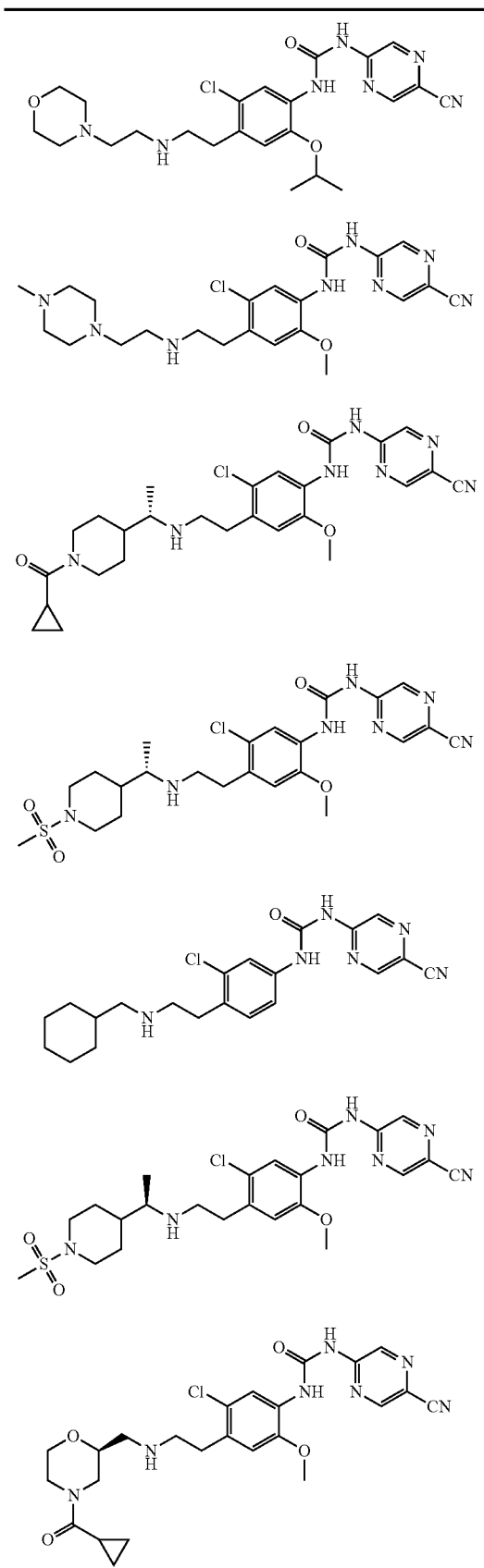
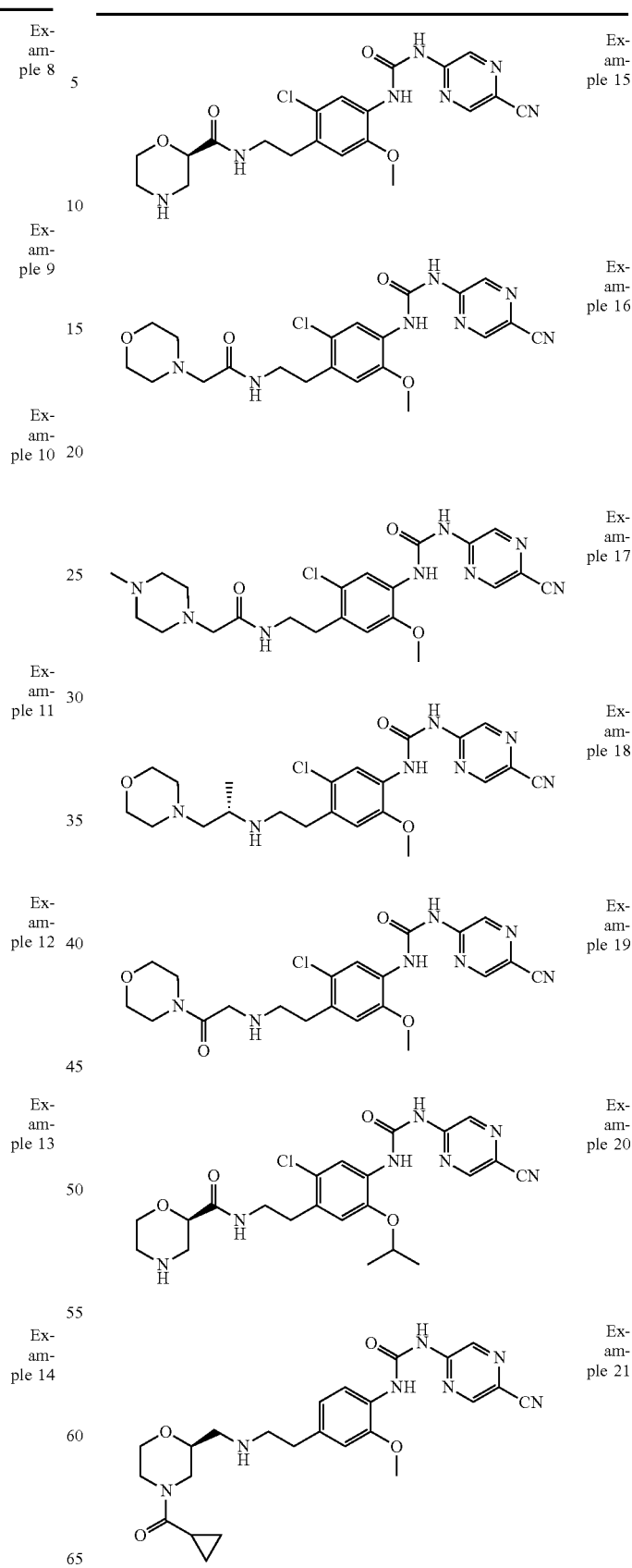

TABLE 1-continued
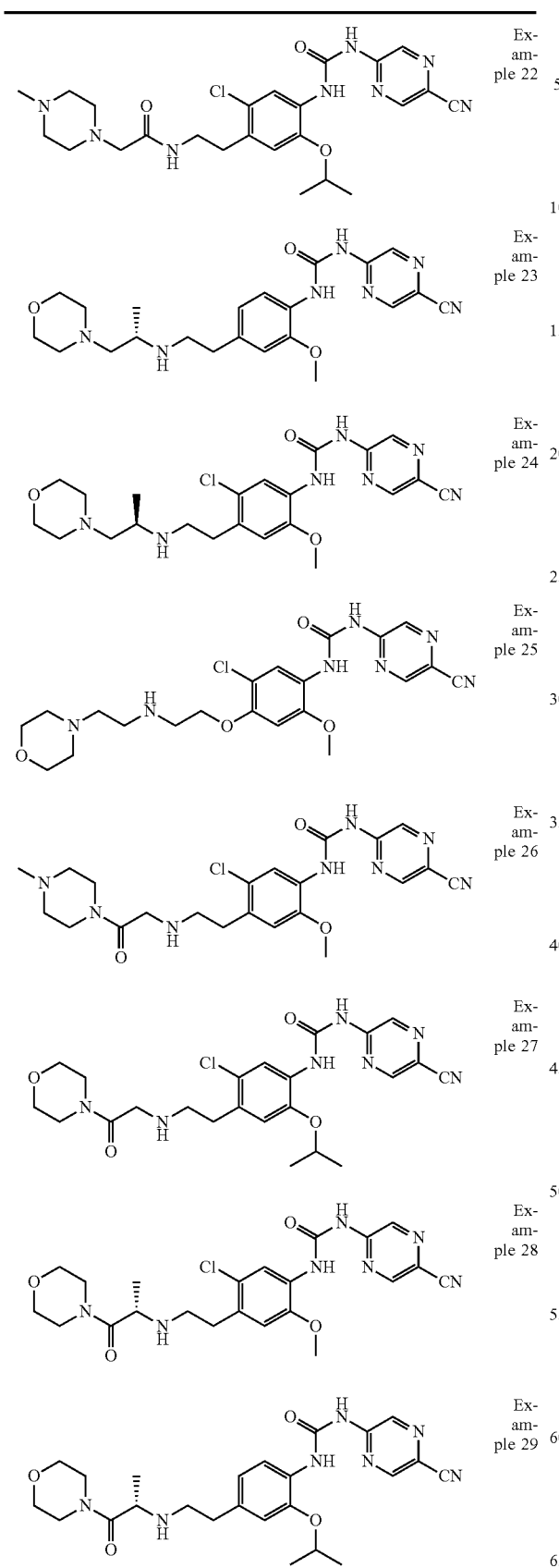
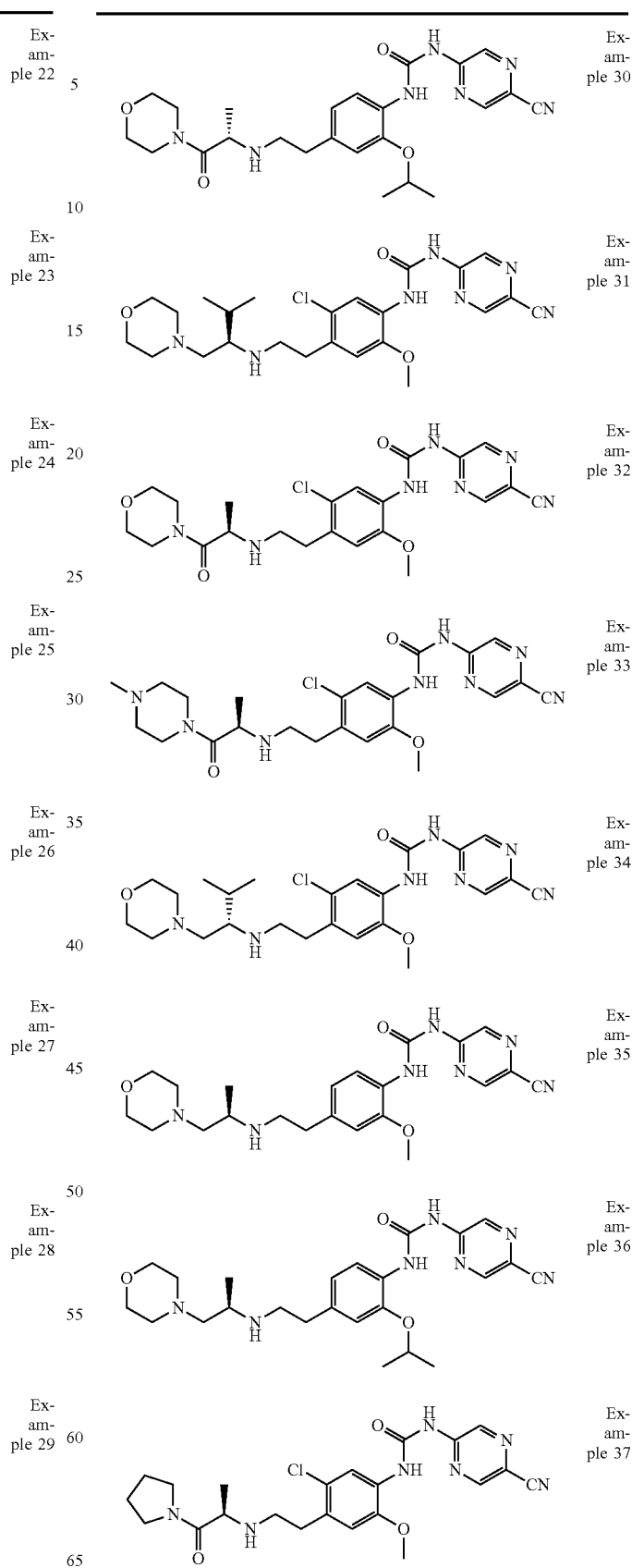

TABLE 1-continued
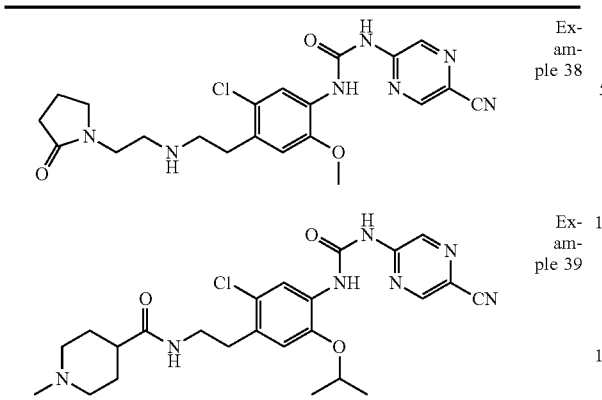
Example 38
Example 39
TABLE 1-continued
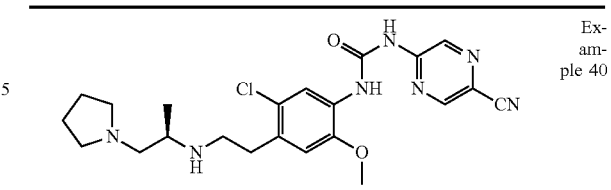
Example 40
The reaction schemes used for the preparation of the compounds are as follows:
Reference Scheme for Example 1 (Synthetic Method A)
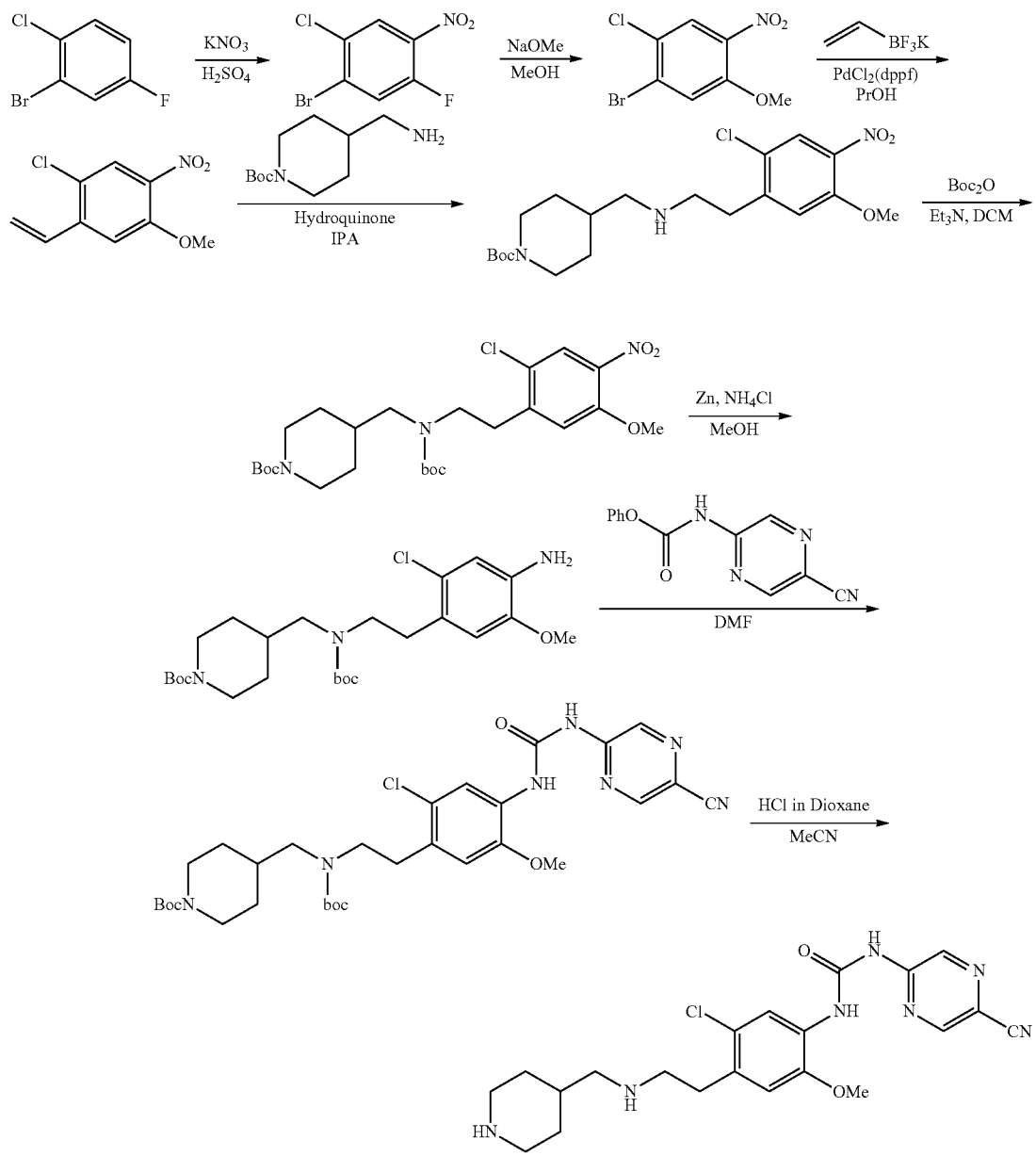

Reference Scheme for Example 10 (Synthetic Method B)
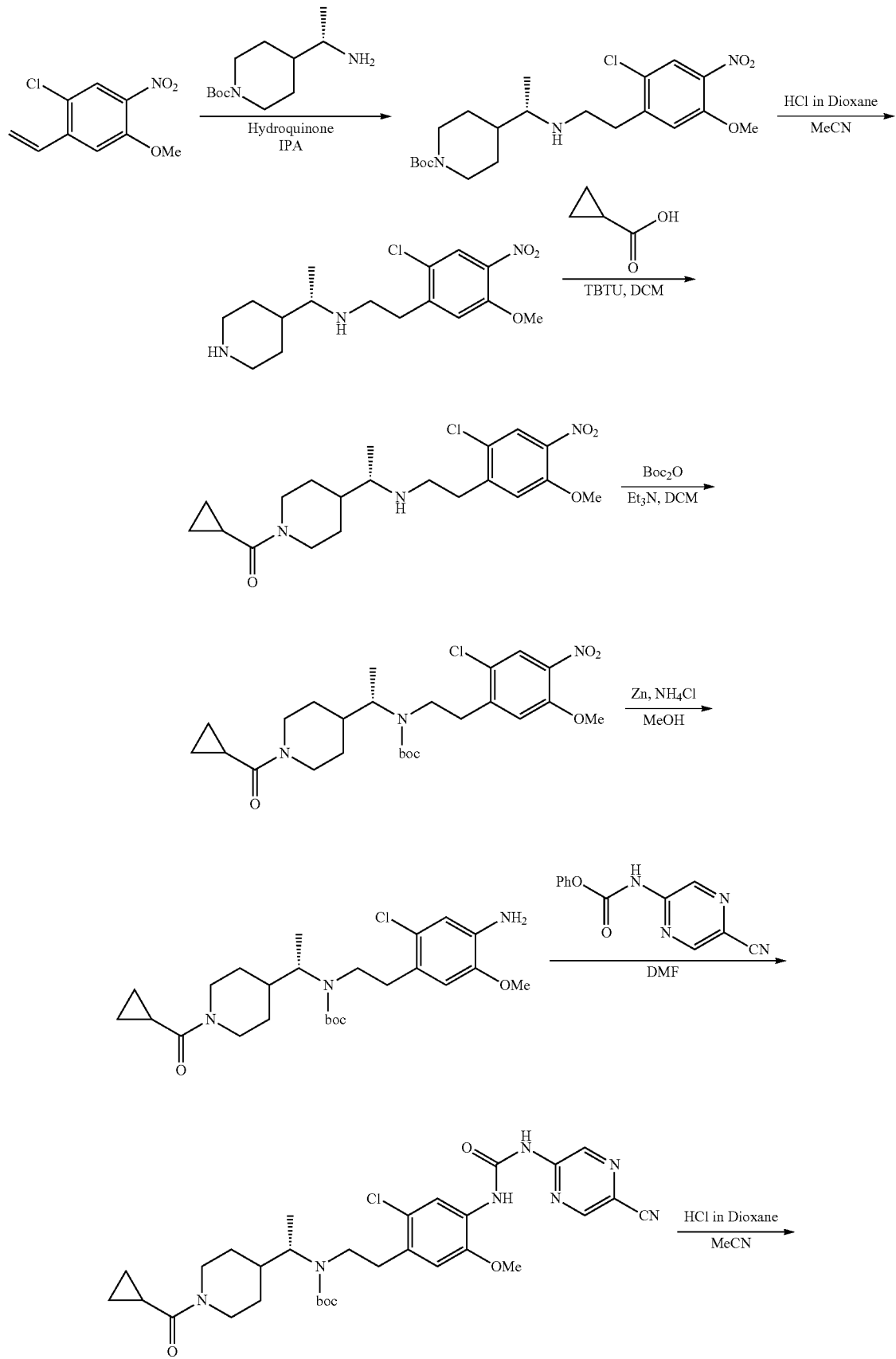

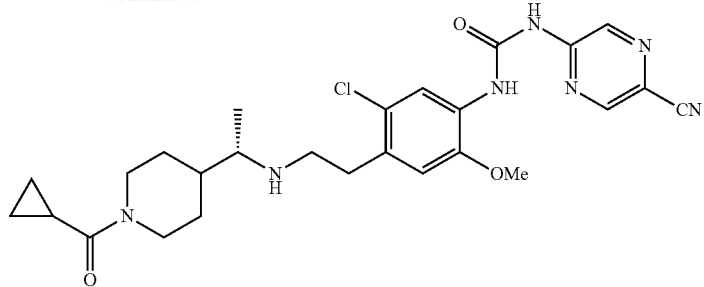
Reference Scheme for Example 12 (Synthetic Method C)
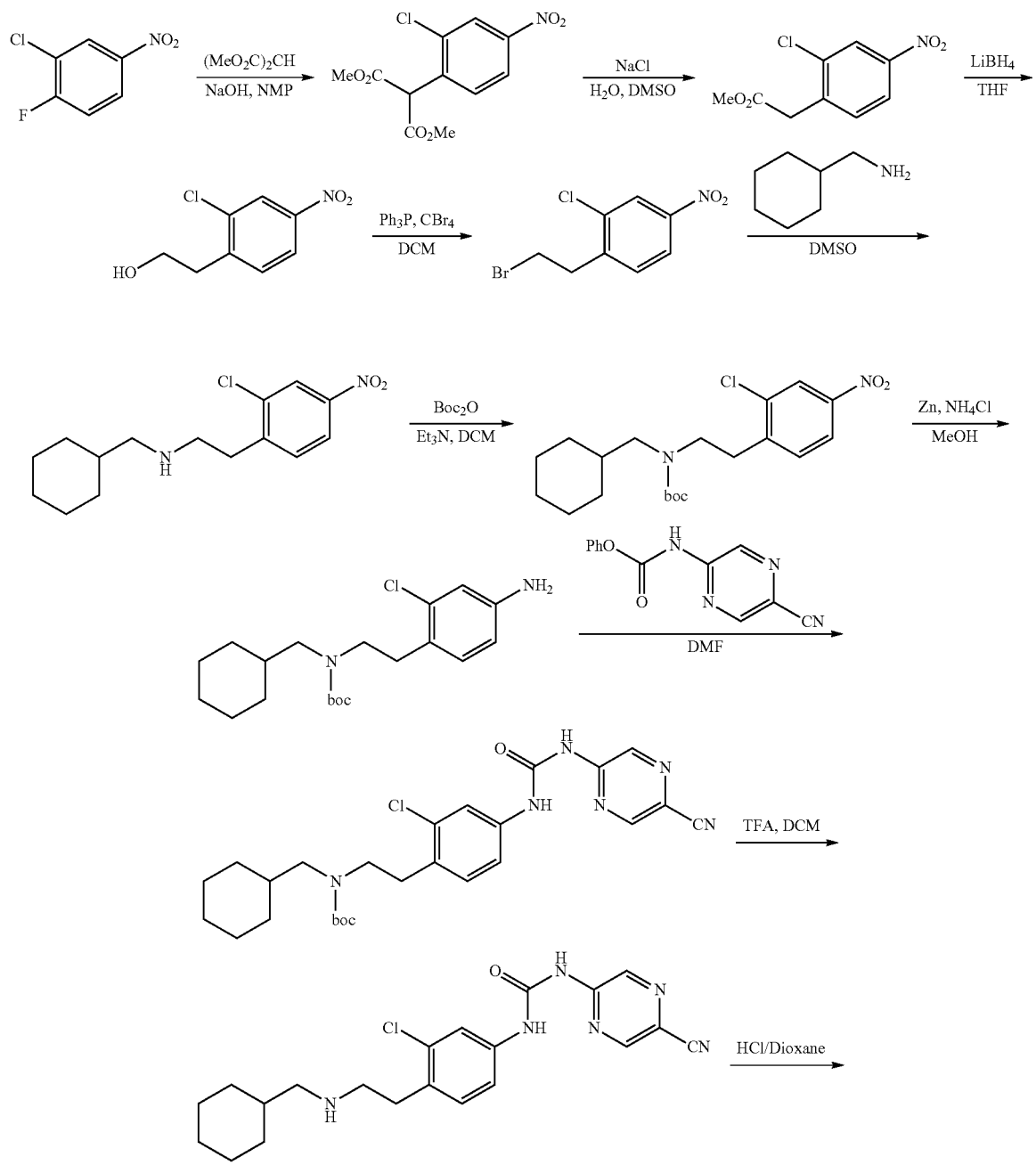

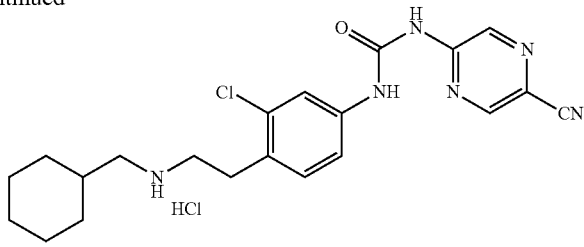
Reference Scheme for Example 15 (Synthetic Method D)
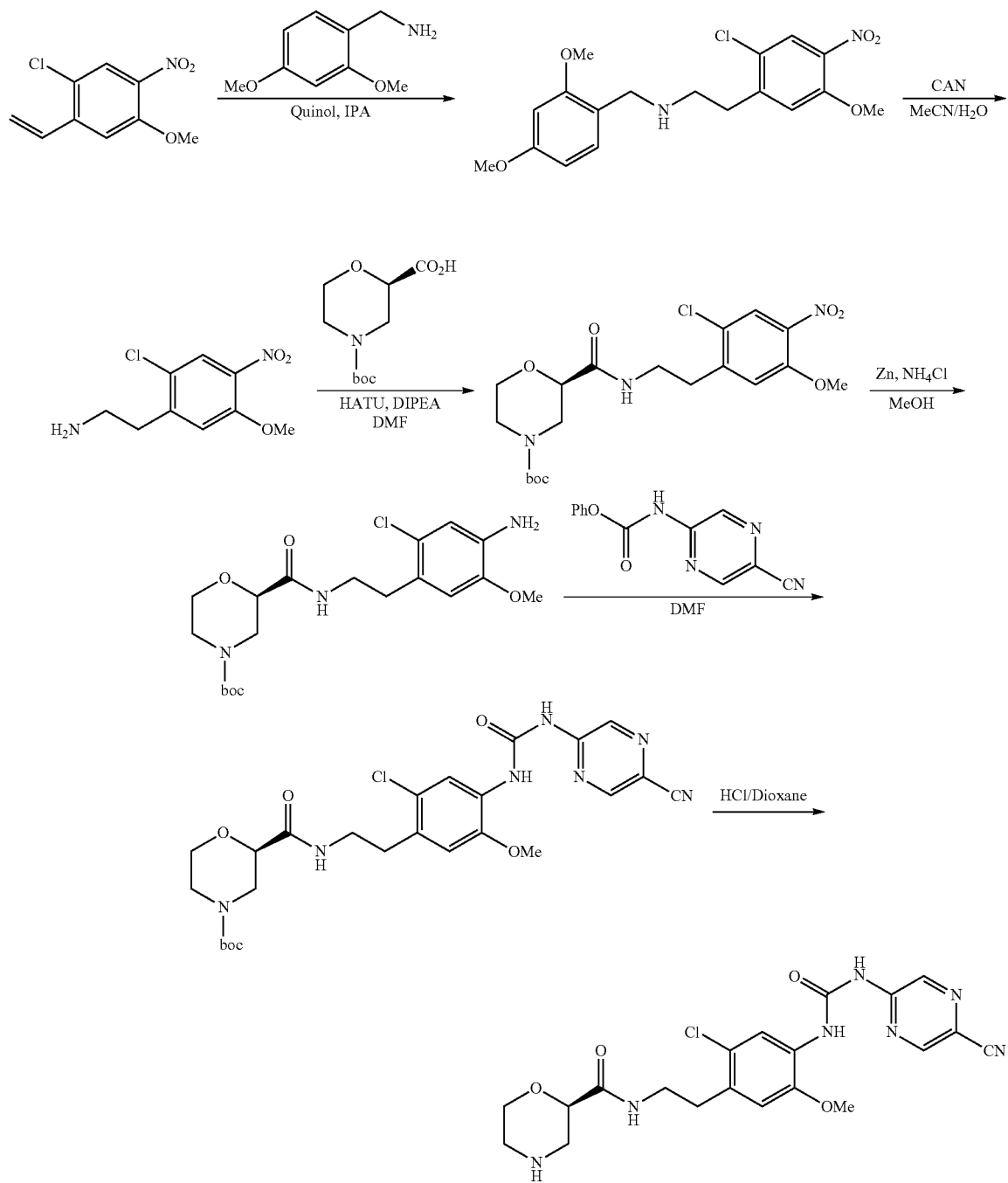

Reference Scheme for Example 16 (Synthetic Method E)
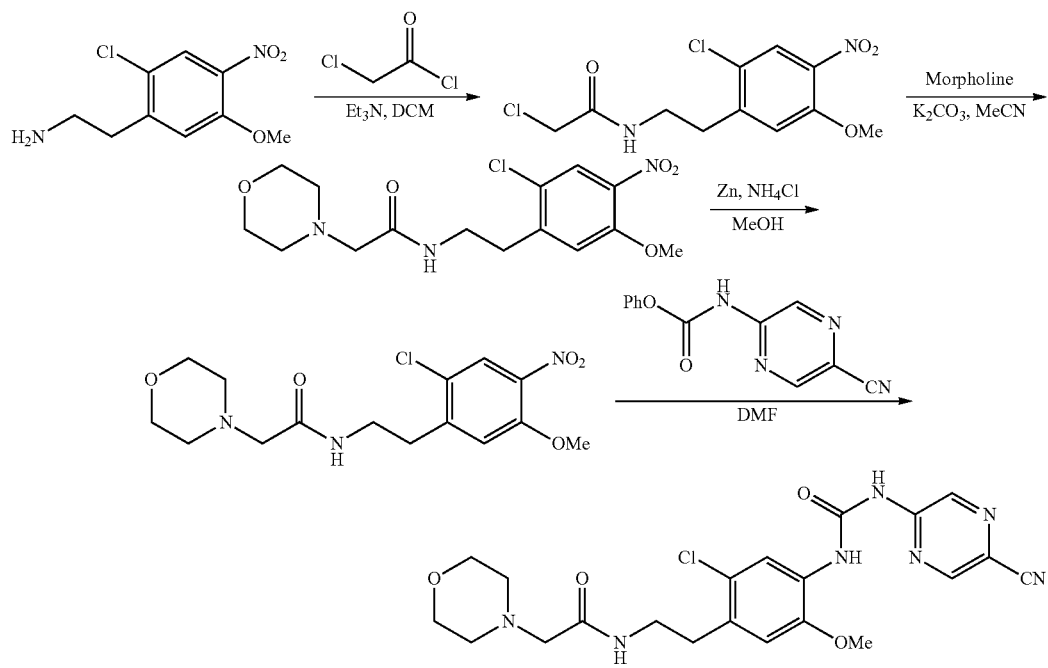
Reference Scheme for Example 25 (Synthetic Method F)
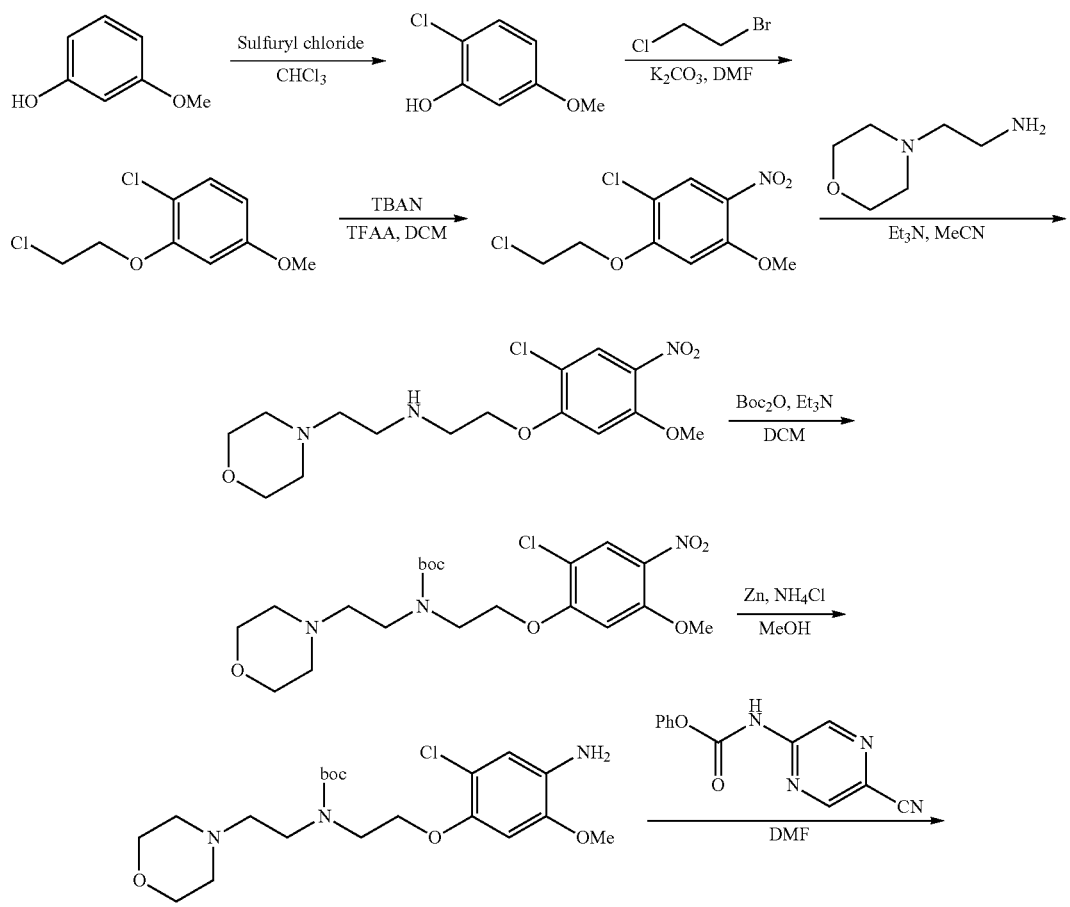

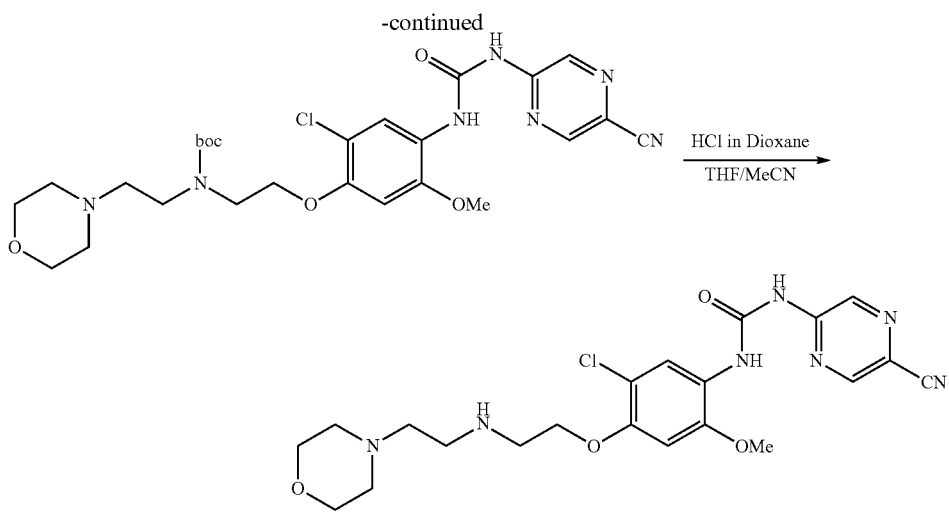

TABLE 2

| Ex. No. | Name | Synthetic method | $^1$H NMR | HPLC (RT) | LC (RT) | MS (M$^+$) | Method HPLC | MS |
|---|---|---|---|---|---|---|---|---|
| 1 | 1-(5-Chloro-2-methoxy-4-{2-[(piperidin-4-ylmethyl)-amino]-ethyl}-phenyl)-3-(5-cyano-pyrazin-2-yl)-urea hydrochloride | A | (DMSO-d$_6$) δ 10.86 (s, 1H), 10.04 (s, 1H), 9.19 (br s, 2H), 9.05 (s, 1H), 8.94 (d, 2H), 8.78 (br s, 1H), 8.28 (s, 1H), 7.13 (s, 1H), 3.94 (s, 3H), 3.35-3.25 (m, 2H), 3.12 (s, 4H), 2.98-2.75 (m, 5H), 1.98 (d, 2H) and 1.15 (q, 2H) | 4.772 | 3.424 | 462 | A | A |
| 2 | 1-(5-Chloro-2-methoxy-4-{2-[(morpholin-2-ylmethyl)-amino]-ethyl}-phenyl)-3-(5-cyano-pyrazin-2-yl)-urea hydrochloride | A | (DMSO-d$_6$) δ 10.87 (s, 1H), 10.04 (s, 1H), 9.82 (br s, 1H), 9.60 (br s, 1H), 9.50 (br s, 1H), 9.17 (br s, 1H), 9.05 (s, 1H), 8.94 (s, 1H), 8.25 (s, 1H), 7.10 (s, 1H), 4.28 (t, 1H), 4.05 (dd, 1H), 3.94 (s, 3H), 3.84 (t, 1H) and 3.50-2.82 (m, 10H) | — | 4.880 | 446 | — | B |
| 3 | 1-(5-Chloro-2-methoxy-4-{2-[((R)-1-morpholin-2-ylmethyl)-amino]-ethyl}-phenyl)-3-(5-cyano-pyrazin-2-yl)-urea hydrochloride | A | (DMSO-d$_6$) δ 10.83 (s, 1H), 10.03 (s, 1H), 9.64 (br s, 1H), 9.35 (br s, 2H), 9.10 (br s, 1H), 9.04 (s, 1H), 8.93 (s, 1H), 8.26 (s, 1H), 7.09 (s, 1H), 4.20 (t, 1H), 4.04 (dd, 1H), 3.95 (s, 3H), 3.82 (t, 1H), 3.40-2.98 (m, 9H) and 2.89 (t, 1H) | 4.77 | 2.79 | 446 | A | C |
| 4 | 1-(5-Chloro-2-methoxy-4-{2-[((S)-1-morpholin-2-ylmethyl)-amino]-ethyl}-phenyl)-3-(5-cyano-pyrazin-2-yl)-urea hydrochloride | A | (DMSO-d$_6$) δ 10.85 (s, 1H), 10.04 (s, 1H), 9.69 (br s, 1H), 9.40 (br s, 2H), 9.11 (br s, 1H), 9.04 (s, 1H), 8.94 (s, 1H), 8.26 (s, 1H), 7.09 (s, 1H), 4.21 (t, 1H), 4.04 (dd, 1H), 3.94 (s, 3H), 3.82 (t, 1H), 3.27-3.23 (m, 3H), 3.07-2.91 (m, 5H) and 2.88 (t, 1H) | 4.774 | 1.672 | 446 | A | D |
| 5 | 1-(5-Chloro-2-methoxy-4-{2-[((R)-1-morpholin-2-ylmethyl)-amino]-ethyl}-phenyl)-3-(5-cyano-pyrazin-2-yl)-urea hydrochloride | A | (DMSO-d$_6$) δ 10.84 (s, 1H), 10.04 (s, 1H), 9.18 (br s, 1H), 9.14 (br s, 1H), 9.06 (s, 1H), 8.92 (s, 1H), 8.26 (s, 1H), 7.13 (s, 1H), 3.95 (s, 3H), 3.20 (d, 1H), 3.10 (s, 4H), 3.02-2.85 (m, 2H), 2.82-2.68 (m, 2H), 2.33-2.15 (m, 1H), 1.92-1.78 (m, 2H), 1.72-1.55 (m, 1H) and 1.31-1.19 (m, 1H) | 4.892 | 1.571 | 444 | A | D |
| 6 | 1-(5-Chloro-2-methoxy-4-{2-[((S)-1-morpholin-2-ylmethyl)-amino]-ethyl}-phenyl)-3-(5-cyano-pyrazin-2-yl)-urea hydrochloride | A | (DMSO-d$_6$) δ 10.84 (s, 1H), 10.03 (s, 1H), 9.25 (br s, 1H), 9.17 (br s, 1H), 9.10 (br s, 1H), 9.07 (d, 1H), 8.99 (br s, 1H), 8.94 (s, 1H), 8.26 (s, 1H), 7.13 (s, 1H), 3.95 (s, 3H), 3.20 (br d, 1H), 3.11 (s, 2H), 3.02-2.85 (m, 2H), 2.84-2.62 (m, 3H), 2.40-2.21 (m, 1H), 1.92-1.72 (m, 2H), 1.71-1.59 (m, 1H) and 1.32-1.23 (m, 1H) | 4.777 | 1.705 | 444 | A | D |
| 7 | 1-{5-Chloro-2-methoxy-4-[2-(2-morpholin-4-yl-ethylamino)-ethyl]-phenyl}-3-(5-cyano-pyrazin-2-yl)-urea hydrochloride | A | (DMSO-d$_6$) δ 11.29 (br s, 1H), 10.86 (s, 1H), 10.04 (s, 1H), 9.49 (br s, 2H), 9.04 (s, 1H), 8.94 (s, 1H), 8.26 (s, 1H), 7.16 (s, 1H), 3.95-3.89 (m, 4H), 3.80 (br s, 2H), 3.51-3.36 (m, 4H), 3.30-3.00 (m, 4H) | 5.59 | 3.200 | 460 | A | E |
| 8 | 1-{5-Chloro-2-isopropoxy-4-[2-(2-morpholin-4-yl-ethylamino)-ethyl]-phenyl}-3-(5-cyano-pyrazin-2-yl)-urea hydrochloride | A | (DMSO-d$_6$) δ 11.30 (br s, 1H), 11.07 (s, 1H), 10.06 (br s, 1H), 9.48 (br s, 2H), 8.94 (s, 1H), 8.86 (s, 1H), 8.30 (s, 1H), 7.18 (s, 1H), 4.75 (septet, 1H), 4.10-3.92 (m, 2H), 3.85-3.72 (m, 2H), 3.62-3.40 (m, 5H), 3.28-3.02 (m, 6H) and 1.37 (d, 6H) | 5.492 | 1.907 | 488 | A | F |

TABLE 2-continued

| Ex. No. | Name | Synthetic method | $^1$H NMR | HPLC (RT) | LC (RT) | MS (M$^+$) | Method HPLC | MS |
|---|---|---|---|---|---|---|---|---|
| 9 | 1-(5-Chloro-2-methoxy-4-{2-[2-(4-methyl-piperazin-1-yl)-ethylamino]-ethyl}-phenyl)-3-(5-cyano-pyrazin-2-yl)-urea hydrochloride | A | (DMSO-d$_6$) δ 10.86 (s, 1H), 10.04 (s, 1H), 9.14 (br s, 2H), 9.05 (s, 1H), 8.94 (s, 1H), 8.26 (s, 1H), 7.14 (s, 1H), 3.92 (s, 3H), 3.35-3.07 (m, 11H), 3.05-2.90 (br, 3H) and 2.78 (s, 3H) | 4.877 | 1.625 | 473 | A | F |
| 10 | 1-(5-Chloro-4-{2-[(S)-1-(1-cyclopropane-carbonyl-piperidin-4-yl)-ethylamino]-ethyl}-2-methoxy-phenyl)-3-(5-cyano-pyrazin-2-yl)-urea hydrochloride | B | (DMSO-d$_6$) δ 10.81 (s, 1H), 10.03 (s, 1H), 9.04 (s, 1H), 8.95-8.94 (d, 1H), 8.76 (s, 1H), 8.46 (s, 1H), 8.27 (s, 1H), 7.11 (s, 1H), 3.96 (s, 3H), 3.34 (m, 4H), 3.07-3.05 (m, 3H) 2.28-2.26 (m, 2H), 1.99 (m, 3H), 1.75-1.69 (m, 3H), 1.23 (m, 4H) and 0.69 (d, 4H) | 6.069 | 2.697 | 525 | A | F |
| 11 | 1-(5-Chloro-4-{2-[(S)-1-(1-methanesulfonyl-piperidin-4-yl)-ethylamino]-ethyl}-2-methoxy-phenyl)-3-(5-cyano-pyrazin-2-yl)-urea hydrochloride | B | (DMSO-d$_6$) δ 10.05 (s, 1H), 9.07 (s, 1H), 8.94 (s, 1H), 8.24 (s, 1H), 7.15 (s, 1H), 3.94 (s, 3H), 3.62 (m, 2H), 3.21 (m, 1H), 3.17-3.10 (m, 4H), 2.87 (s, 3H) 2.70-2.62 (m, 2H), 1.92-1.89 (m, 3H) 1.74-1.71 (m, 1H), 1.39-1.37 (m, 2H) and 1.22-1.20 (d, 4H). | 6.177 | 2.768 | 535 | A | F |
| 12 | 1-{3-Chloro-4-[2-(cyclo-hexylmethyl-amino)-ethyl]-phenyl}-3-(5-cyano-pyrazin-2-yl)-urea hydrochloride | C | (DMSO-d$_6$) δ 10.34 (s, 1H), 9.95 (s, 1H), 9.20 (s, 1H), 8.89 (s, 1H), 8.50 (s, 1H), 7.78 (s, 1H), 7.40-7.34 (m, 2H), 3.08-3.04 (d, 4H), 2.83 (s, 2H), 1.73 (t, 4H), 1.63 (d, 1H), 1.23 (s, 3H) 1.21-1.13 (m, 1H) and 0.97 (q, 2H) | 9.384 | — | 413 | A | — |
| 13 | 1-(5-Chloro-4-{2-[(R)-1-(1-methanesulfonyl-piperidin-4-yl)-ethylamino]-ethyl}-2-methoxy-phenyl)-3-(5-cyano-pyrazin-2-yl)-urea hydrochloride | B | (DMSO-d$_6$) δ 10.86 (s, 1H), 10.04 (s, 1H), 9.34 (s, 1H), 9.05-8.83 (d, 3H), 8.26 (s, 1H), 7.13 (s, 1H), 3.96 (s, 3H), 3.64 (m, 2H), 3.25 (m, 1H), 3.12 (m, 4H), 2.88 (m, 3H) and 2.68 (m, 3H) 1.88 (m, 2H), 1.73 (m, 1H) 1.37 (m, 3H) and 1.22 (d, 3H). | — | 2.644 | 534 | — | F |
| 14 | 1-(5-Chloro-4-{2-[((S)-4-cyclopropanecarbonyl-morpholin-2-ylmethyl)-amino]-ethyl}-2-methoxy-phenyl)-3-(5-cyano-pyrazin-2-yl)-urea hydrochloride | B | (DMSO-d$_6$) δ 10.86 (s, 1H), 10.04 (s, 1H), 9.04 (s, 1H), 8.94 (bs, 2H), 8.26 (s, 1H), 7.09 (s, 1H), 4.33 (d, 1H), 4.17 (d, 1H), 3.95 (s, 3H), 3.23-3.07 (m, 8H), 3.85-3.73 (m, 2H), 3.53 (m, 1H), 2.00 (t, 1H) and 0.75 (d, 4H) | — | 2.430 | 512 | — | F |
| 15 | (R)-Morpholine-2-carboxylic acid (2-{2-chloro-4-[3-(5-cyano-pyrazin-2-yl)-ureido]-5-methoxy-phenyl}-ethyl)-amide hydrochloride | D | (DMSO-d$_6$) δ 10.80 (s, 1H), 10.00 (s, 1H), 9.15 (s, 2H), 9.03 (s, 1H), 8.22 (s, 2H), 6.99 (s, 1H), 4.23-4.19 (dd, 1H), 4.05-4.01 (dd, 1H), 3.93 (s, 3H), 3.81-3.76 (m, 1H), 3.41-3.35 (m, 3H), 3.22-3.18 (m, 1H), 3.04-3.03 (m, 1H), 2.95-2.89 (m, 1H) and 2.84 (s, 2H) | — | 2.600 | 459 | — | F |
| 16 | N-(2-{2-Chloro-4-[3-(5-cyano-pyrazin-2-yl)-ureido]-5-methoxy-phenyl}-ethyl)-2-morpholin-4-yl-acetamide hydrochloride | E | (DMSO-d$_6$) δ 10.87 (s, 1H), 10.43 (s, 1H), 10.00 (s, 1H), 9.05 (s, 1H), 8.94 (s, 1H), 8.27 (s, 1H), 8.20 (s, 1H), 7.07 (s, 1H), 3.94 (m, 4H), 3.79 (s, 3H), 3.45-3.37 (m, 4H), 3.05-3.04 (s, 4H) and 2.87 (s, 2H) | — | 2.296 | 473 | — | F |
| 17 | N-(2-{2-Chloro-4-[3-(5-cyano-pyrazin-2-yl)-ureido]-5-methoxy-phenyl}-ethyl)-2-(4-methyl-piperazin-1-yl)-acetamide hydrochloride | E | (DMSO-d$_6$) δ 10.83 (s, 1H), 10.00 (s, 1H), 9.05 (s, 1H), 8.94 (s, 1H), 8.42 (s, 1H), 8.22 (s, 1H), 7.05 (s, 1H), 3.93 (s, 3H), 3.40-3.37 (m, 4H), 3.33-3.19 (m, 4H), 3.19-3.17 (m, 2H), 2.79 (s, 2H). and 2.67 (s, 3H) | — | 2.605 | 486 | — | F |
| 18 | 1-{5-Chloro-2-methoxy-4-[2-((S)-1-methyl-2-morpholin-4-yl-ethylamino)-ethyl]-phenyl}-3-(5-cyano-pyrazin-2-yl)-urea hydrochloride | A | (DMSO-d$_6$) δ 11.32 (s, 1H), 10.89 (s, 1H), 10.05 (s, 1H), 9.66 (bs, 1H), 9.05 (s, 1H), 8.94 (s, 1H), 4.11-3.77 (m, 8H), 3.74-3.52 (m, 3H), 3.30-3.13 (m, 7H) and 1.38 (s, 3H) | — | 2.634 | 473 | — | F |
| 19 | 1-{5-Chloro-2-methoxy-4-[2-(2-morpholin-4-yl-2-oxo-ethylamino)-ethyl]-phenyl}-3-(5-cyano-pyrazin-2-yl)-urea hydrochloride | A | (DMSO-d$_6$) δ 10.89 (s, 1H), 10.05 (bs, 1H), 9.17 (bs, 2H), 9.05 (s, 1H), 8.94 (s, 1H), 8.25 (s, 1H), 7.09 (s, 1H), 4.14 (s, 2H), 3.94 (s, 3H), 3.61 (t, 4H), 3.42 (m, 4H), 3.38 (t, 2H) and 3.13 (d, 3H) | — | 2.593 | 474 | — | G |
| 20 | (R)-Morpholine-2-carboxylic acid (2-{2- | D | (DMSO-d$_6$) δ 11.01 (s, 1H), 10.03 (s, 1H), 9.18 (s, 2H), 8.94 (s, 1H), 8.86 (s, 1H), 8.25 (s, 1H), | — | 2.738 | 487 | — | G |

TABLE 2-continued

| Ex. No. | Name | Synthetic method | ¹H NMR | HPLC (RT) | LC (RT) | MS (M⁺) | Method HPLC | Method MS |
|---|---|---|---|---|---|---|---|---|
|  | chloro-4-[3-(5-cyano-pyrazin-2-yl)-ureido]-5-isopropoxy-phenyl}-ethyl)-amide hydrochloride |  | 8.16-8.14 (m, 1H), 7.00 (s, 1H), 4.73-4.67 (m, 1H), 4.20 (dd, 1H), 4.02 (dd, 1H), 3.78 (t, 1H), 3.41 (m, 2H), 3.20 (d, 1H), 3.02-3.01 (m, 1H), 2.93 (m, 1H) and 2.81 (t, 2H) |  |  |  |  |  |
| 21 | 1-(5-Cyano-pyrazin-2-yl)-3-(4-{2-[((S)-4-cyclopropanecarbonyl-morpholin-2-ylmethyl)-amino]-ethyl}-2-methoxy-phenyl)-urea hydrochloride | C | (DMSO-d₆) δ 10.63 (s, 1H), 9.81 (s, 1H), 9.03 (d, 1H), 8.92 (s, 1H), 8.04 (d, 1H), 6.94 (s, 1H), 6.80 (d, 1H), 3.90-3.82 (m, 5H), 3.45-3.40 (m, 3H), 2.81 (t, 2H), 2.72-2.62 (m, 5H), 1.97 (t, 2H) and 0.87 (m, 4H) | — | 2.472 | 479 | — | G |
| 22 | N-(2-{2-Chloro-4-[3-(5-cyano-pyrazin-2-yl)-ureido]-5-isopropoxy-phenyl}-ethyl)-2-(4-methyl-piperazin-1-yl)-acetamide hydrochloride | E | (DMSO-d₆) δ 11.64 (s, 1H), 11.11 (s, 1H), 10.03 (s, 1H), 8.97 (s, 1H), 8.86 (s, 1H), 8.58 (s, 1H), 8.23 (s, 1H), 7.10 (s, 1H), 4.76-4.70 (m, 1H), 3.71 (m, 2H), 3.53 (s, 3H), 3.41-3.36 (m, 4H), 3.19-3.17 (m, 4H), 2.85-2.79 (m, 2H), 2.79 (s, 3H) and 1.37 (s, 6H) | — | 2.705 | 514 | — | G |
| 23 | 1-(5-Cyano-pyrazin-2-yl)-3-{2-methoxy-4-[2-((S)-1-methyl-2-morpholin-4-yl-ethylamino)-ethyl]-phenyl}-urea hydrochloride | C | (DMSO-d₆) δ 10.74 (bs, 1H), 9.78 (s, 1H), 9.05 (s, 1H), 8.93 (s, 1H), 8.11 (s, 1H), 7.01 (s, 1H), 6.88 (s, 1H), 3.93 (m, 3H), 3.62 (t, 5H), 3.22 (d, 2H), 3.05-2.94 (m, 4H), 2.18-2.02 (t, 4H) and 1.21 (d, 3H) | — | 2.690 | 474 | — | G |
| 24 | 1-{5-Chloro-2-methoxy-4-[2-((R)-1-methyl-2-morpholin-4-yl-ethylamino)-ethyl]-phenyl}-3-(5-cyano-pyrazin-2-yl)-urea hydrochloride | A | (DMSO-d₆) δ 11.17 (s, 1H), 10.86 (s, 1H), 10.05 (s, 1H), 9.53 (bs, 2H), 9.05 (s, 1H), 8.94 (s, 1H), 8.27 (s, 1H), 7.21-7.17 (d, 2H), 3.96 (s, 3H), 3.62-3.61 (m, 5H), 3.03-3.01 (m, 2H), 2.89-2.80 (m, 8H), and 1.28 (d, 3H) | — | 1.452 | 472 | — | G |
| 25 | 1-{5-Chloro-2-methoxy-4-[2-(2-morpholin-4-yl-ethylamino)-ethoxy]-phenyl}-3-(5-cyano-pyrazin-2-yl)-urea hydrochloride | F | (DMSO-d₆) δ 11.31 (s, 1H), 10.80 (s, 1H), 9.91 (s, 1H), 9.69 (bs, 2H), 9.04 (s, 1H), 8.93 (s, 1H), 8.21 (s, 1H), 7.10 (s, 1H), 4.44 (s, 3H), 3.97-3.94 (m, 5H), 3.83-3.80 (m, 2H), 3.41-3.37 (m, 5H), and 3.17-3.07 (m, 2H) | — | 5.205 | 500 | — | C |
| 26 | 1-(5-Chloro-2-methoxy-4-{2-[2-(4-methyl-piperazin-1-yl)-2-oxo-ethylamino]-ethyl}-phenyl)-3-(5-cyano-pyrazin-2-yl)-urea hydrochloride | A | (DMSO-d₆) δ 11.25 (s, 1H), 10.86 (s, 1H), 10.05 (s, 1H), 9.25-9.23 (bs, 1H), 9.05-9.04 (s, 1H), 8.95 (s, 1H), 8.26 (s, 1H), 7.10 (s, 1H), 4.14 (d, 2H), 3.95 (s, 3H), 3.49-3.41 (m, 4H), 2.99-2.85 (m, 6H), 2.78 (t, 2H) and 2.68 (s, 3H) | — | 0.663 | 485 | — | D |
| 27 | 1-{5-Chloro-2-isopropoxy-4-[2-(2-morpholin-4-yl-2-oxo-ethylamino)-ethyl]-phenyl}-3-(5-cyano-pyrazin-2-yl)-urea hydrochloride | A | (DMSO-d₆) δ 11.06 (s, 1H), 10.07 (s, 1H), 9.04 (bs, 2H), 8.87 (s, 1H), 8.87 (s, 1H), 8.30 (s, 1H), 7.12 (s, 1H), 4.74 (m, 1H), 4.13 (s, 2H), 3.62-3.57 (m, 4H), 3.52 (d, 2H), 3.38 (t, 2H), 3.15 (t, 2H), 3.08 (t, 2H) and 1.38 (d, 6H) | — | 2.595 | 500 | — | G |
| 28 | 1-{5-Chloro-2-methoxy-4-[2-((S)-1-methyl-2-morpholin-4-yl-2-oxo-ethylamino)-ethyl]-phenyl}-3-(5-cyano-pyrazin-2-yl)-urea hydrochloride | A | (DMSO-d₆) δ 10.84 (s, 1H), 10.04 (s, 1H), 9.35 (s, 1H), 9.04 (bs, 1H), 8.94 (bs, 1H), 8.26 (s, 1H), 7.09 (s, 1H), 4.52 (q, 1H ), 3.95 (s, 3H), 3.66-3.56 (m, 6H), 3.51-3.49 (m, 3H), 3.09-3.05 (t, 4H) and 1.40 (d, 3H) | — | 2.501 | 486 | — | G |
| 29 | 1-(5-Cyano-pyrazin-2-yl)-3-{2-isopropoxy-4-[2-((S)-1-methyl-2-morpholin-4-yl-ethylamino)-ethyl]-phenyl}-urea hydrochloride | A | (DMSO-d₆) δ 11.23 (s, 1H), 10.96 (s, 1H), 9.92 (s, 1H), 9.45 (d, 2H), 8.90 (d, 2H), 8.14 (d, 2H), 7.05 (s, 1H), 6.85 (d, 1H), 4.72 (s, 1H), 3.88-3.63 (m, 4H), 3.18-3.15 (m, 3H), 2.74-2.18 (m, 6H) and 1.25 (d, 9H) | — | 1.519 | 467 | — | D |
| 30 | 1-(5-Cyano-pyrazin-2-yl)-3-{2-isopropoxy-4-[2-((S)-1-methyl-2-morpholin-4-yl-2-oxo-ethylamino)-ethyl]-phenyl}-urea hydrochloride | C | (DMSO-d₆) δ 10.95 (s, 1H), 9.92 (s, 1H), 9.31 (s, 1H), 8.94-8.57 (d, 3H), 8.15-8.13 (s, 1H), 6.99 (s, 1H), 6.82-6.80 (d, 1H), 4.73 (q, 1H), 4.45 (s, 3H), 3.57-3.56 (m, 3H), 3.02-3.00 (m, 1H), 2.93 (d, 2H) and 1.39-1.36 (d, 9H). | — | 1.436 | 480 | — | F |
| 31 | 1-{5-Chloro-2-methoxy-4-[2-((R)-2-methyl-1- | A | (DMSO-d₆) δ 11.24 (s, 1H), 10.87 (s, 1H), 10.06 (s, 1H), 9.54 (bs, 1H), 9.26 (bs, 1H), 8.95 (s, | — | 1.708 | 500 | — | F |

TABLE 2-continued

| Ex. No. | Name | Synthetic method | ¹H NMR | HPLC (RT) | LC (RT) | MS (M⁺) | Method HPLC | Method MS |
|---|---|---|---|---|---|---|---|---|
| | morpholin-4-ylmethyl-propylamino)-ethyl]-phenyl}-3-(5-cyano-pyrazin-2-yl)-urea hydrochloride | | 2H), 8.27 (s, 1H), 7.33 (d, 2H), 4.14-4.05 (m, 2H), 3.96 (s, 3H), 3.83-3.63 (m, 4H), 3.43-3.40 (m, 5H), 2.32-2.20 (m, 1H), 1.23 (s, 3H) and 1.37 (d, 6H) | | | | | |
| 32 | 1-{5-Chloro-2-methoxy-4-[2-((R)-1-methyl-2-morpholin-4-yl-2-oxo-ethylamino)-ethyl]-phenyl}-3-(5-cyano-pyrazin-2-yl)-urea hydrochloride | A | (DMSO-d₆) δ 10.84 (s, 1H), 10.05 (s, 1H), 9.37 (s, 1H), 9.05-8.95 (bs, 2H), 8.26 (s, 1H), 7.09 (s, 1H), 4.44 (q, 1H), 3.95 (s, 3H), 3.63-3.54 (m, 8H), 3.13-3.08 (m, 4H) and 1.38 (d, 3H) | — | 1.435 | 486 | — | F |
| 33 | 1-(5-Chloro-2-methoxy-4-{2-[(R)-1-methyl-2-(4-methyl-piperazin-1-yl)-2-oxo-ethylamino]-ethyl}-phenyl)-3-(5-cyano-pyrazin-2-yl)-urea | A | (DMSO-d₆) δ 11.42 (s, 1H), 10.88 (s, 1H), 10.05 (s, 1H), 9.70-9.68 (bs, 1H), 9.23 (s, 1H), 9.05 (s, 1H), 8.95 (s, 1H), 8.25 (s, 1H), 7.11 (s, 2H), 4.94-4.09 (m, 2H), 3.95 (s, 4H), 4.00-3.98 (m, 4H), 3.20-3.16 (m, 6H), 2.76 (s, 3H) and 1.43-1.40 (d, 3H) | — | 0.708 | 499 | — | F |
| 34 | 1-{5-Chloro-2-methoxy-4-[2-((S)-2-methyl-1-morpholin-4-ylmethyl-propylamino)-ethyl]-phenyl}-3-(5-cyano-pyrazin-2-yl)-urea hydrochloride | | (DMSO-d₆) δ 11.25 (s, 1H), 10.89 (s, 1H), 10.05 (s, 1H), 9.66 (bs, 2H), 9.05 (s, 1H), 8.94 (s, 1H), 8.26 (s, 1H), 4.04 (d, 2H), 3.88 (s, 3H), 3.88-3.83 (m, 4H), 3.47-3.37 (m, 4H), 3.26 (br t, 4H), 2.33 (m, 1H) and 1.03 (2xd, 6H) | — | 3.069 | 502 | — | G |
| 35 | 1-(5-Cyano-pyrazin-2-yl)-3-{2-methoxy-4-[2-((R)-1-methyl-2-morpholin-4-yl-ethylamino)-ethyl]-phenyl}-urea hydrochloride | A | | | | | | |
| 36 | 1-(5-Cyano-pyrazin-2-yl)-3-{2-isopropoxy-4-[2-((R)-1-methyl-2-morpholin-4-yl-ethylamino)-ethyl]-phenyl}-urea hydrochloride | A | | | | | | |
| 37 | 1-{5-Chloro-2-methoxy-4-[2-((R)-1-methyl-2-oxo-2-pyrrolidin-1-yl-ethylamino)-ethyl]-phenyl}-3-(5-cyano-pyrazin-2-yl)-urea hydrochloride | A | | | | | | |
| 38 | 1-(5-Chloro-2-methoxy-4-{2-[2-(2-oxo-pyrrolidin-1-yl)-ethylamino]-ethyl}-phenyl)-3-(5-cyano-pyrazin-2-yl)-urea hydrochloride | A | | | | | | |
| 39 | 1-Methyl-piperidine-4-carboxylic acid (2-{2-chloro-4-[3-(5-cyano-pyrazin-2-yl)-ureido]-5-isopropoxy-phenyl}-ethyl)-amide hydrochloride | D | | | | | | |
| 40 | 1-{5-Chloro-2-methoxy-4-[2-((R)-1-methyl-2-pyrrolidin-1-yl-ethylamino)-ethyl]-phenyl}-3-(5-cyano-pyrazin-2-yl)-urea hydrochloride | A | | | | | | |

Synthetic Routes A, B, C, D, E and F are described below.

Synthetic Route A (Illustrated with reference to Example 1: 1-(5-Chloro-2-methoxy-4-{2-[(piperidin-4-ylmethyl)-amino]-ethyl}-phenyl)-3-(5-cyano-pyrazin-2-yl)-urea)

Example 1

1A. 1-Bromo-2-chloro-5-fluoro-4-nitrobenzene

Potassium nitrate (2.91 g, 28.8 mmol) was gradually added to a stirred solution of 1-bromo-2-chloro-5-fluorobenzene (5 g, 24 mmol) in concentrated sulphuric acid (50 mL) at −5° C. The reaction was stirred for 10 hours then slowly poured on to crushed ice with stirring. The formed precipitate was collected by filtration and dried under reduced pressure to give the title compound (4.7 g, 77%) as a solid.

1B. 1-Bromo-2-chloro-5-methoxy-4-nitro-benzene

Sodium methoxide (0.043 g, 0.8 mmol) was added slowly to a stirred solution of 1-bromo-2-chloro-5-fluoro-4-nitrobenzene (0.2 g, 0.8 mmol) in MeOH (2 mL) at 0° C. The reaction was stirred at 0° C. for 1.5 hours then water (30 mL) was added and the mixture was extracted with EtOAc (2×20 mL). The combined organic extracts were dried ($Na_2SO_4$) and concentrated under reduced pressure to give the title compound (0.15 g, 75%).

1C. 1-Chloro-4-methoxy-5-nitro-2-vinyl benzene

A mixture of 1-bromo-2-chloro-5-methoxy-4-nitro-benzene (13.0 g, 49.24 mmol), 1,1'-bis(diphenylphosphino)ferrocene-palladium(II)dichloride dichloromethane complex (0.804 g, 0.98 mmol), potassium ethenyl(trifluoro)borate (7.88 g, 59.09 mmol) and triethylamine (6.87 mL, 49.24 mmol) in n-propanol (130 mL) was heated to reflux for 4 hours. The mixture was allowed to cool to room temperature and poured into water (500 mL). The mixture was extracted with DCM (2×300 mL) then the combined organic extracts were dried ($Na_2SO_4$) and the solvent removed under reduced pressure. The residue was purified by column chromatography on neutral silica gel using 1-2% EtOAc/hexane to give the title compound (7.8 g, 75%) as a white solid.

1D. tert-Butyl 4-((2-chloro-5-methoxy-4-nitrophenethylamino)methyl)piperidine-1-carboxylate Tert-butyl 4-(aminomethyl)piperidine-1-carboxylate (0.802 g, 3.74 mmol), 1-chloro-4-methoxy-5-nitro-2-vinylbenzene (0.4 g, 1.87 mmol), quinol (0.082 g, 0.749 mmol) in IPA (16 mL) was heated at 90° C. for 18 hours. The reaction mass was allowed to cool to room temperature, diluted with water (80 mL) and extracted with ethyl acetate (3×40 mL). The combined organic extracts were washed with brine (50 ml), dried ($Na_2SO_4$) and evaporated under reduced pressure. The residue was purified by column chromatography on silica gel (60-120 mesh) using 1.0% MeOH/DCM as the eluent to afford tert-butyl 4-((2-chloro-5-methoxy-4-nitrophenethylamino)methyl) piperidine-1-carboxylate (0.65 g, 81%).

1E. tert-Butyl 4-((tert-butoxy carbonyl(2-chloro-5-methoxy-4-nitrophenethyl)amino)methyl)piperidine-1-carboxylate To a stirred solution of tert-butyl 4-((2-chloro-5-methoxy-4-nitrophenethylamino)methyl) piperidine-1-carboxylate (0.650 g, 1.52 mmol) in DCM (30 mL), triethylamine (0.635 mL, 4.56 mmol) and Boc$_2$O (0.497 g, 2.28 mmol) were added at room temperature and the reaction was stirred for 2 hours. DCM (30 mL) and water (50 mL) were added and the reaction mass stirred for 15 minutes. The separated organic layer was washed with water (2×30 mL), dried ($Na_2SO_4$) and evaporated under reduced pressure to afford tert-butyl 4-((tert-butoxycarbonyl(2-chloro-5-methoxy-4-nitrophenethyl)amino)methyl)piperidine-1-carboxylate (0.8 g, 100%) which was used without further purification.

1F. tert-Butyl 4-(((4-amino-2-chloro-5-methoxyphenethyl)(tert-butoxycarbonyl)amino)methyl)piperidine-1-carboxylate To a solution of tert-butyl 4-((tert-butoxycarbonyl(2-chloro-5-methoxy-4-nitrophenethyl)amino)methyl)piperidine-1-carboxylate (0.8 g, 1.51 mmol) in Methanol (30 mL) was added a saturated solution of —NH$_4$Cl (20 mL) at room temperature. Zinc powder (0.692 g, 10.62 mmol) was added at room temperature and the temperature was raised to 70-80° C. and maintained for 1.5 hours. The reaction mixture was cooled to room temperature and the solution was filtered through a celite pad. Water (100 mL) was added to the filtrate and the mixture extracted with EtOAc (2×60 mL). The combined organic extracts were washed with brine (30 mL), dried ($Na_2SO_4$) and evaporated under reduced pressure to give tert-butyl 4-(((4-amino-2-chloro-5-methoxy phenethyl)(tert-butoxycarbonyl)amino)methyl)piperidine-1-carboxylate (0.7 g, 93%) which was used without further purification.

1G. (5-Cyano-pyrazin-2-yl)-carbamic acid phenyl ester

2-Amino-5-cyano pyrazine (0.25 g, 2.08 mmol) was dissolved in a mixture of 3:1 THF and DCM (40 mL) and pyridine (0.49 g, 6.2 mmol) was added. The mixture was stirred for 15 minutes then phenylchloroformate (0.97 g, 6.2 mmol) was added and the reaction mixture was heated at 50° C. for 2 hours. The reaction mixture was allowed to cool to room temperature then DCM (40 mL) and water (25 mL) were added. The separated organic layer was washed with water (2×25 mL), brine (25 mL), dried ($Na_2SO_4$) and the solvents removed under reduced pressure to give the title compound (0.8 g) which was used without further purification.

1H. tert-Butyl 4-((tert-butoxycarbonyl(2-chloro-4-(3-(5-cyanopyrazin-2-yl)ureido)-5-methoxyphenethyl)amino)methyl) piperidine-1-carboxylate To a solution of tert-butyl 4-(((4-amino-2-chloro-5-methoxyphenethyl)(tert-butoxy carbonyl)amino)methyl)piperidine-1-carboxylate (0.7 g, 1.40 mmol) in DMF (40 mL), (5-cyano-pyrazin-2-yl)-carbamic acid phenyl ester (0.269 g, 1.12 mmol) was added. The mixture was heated at 100° C. for one hour then allowed to cool to room temperature. The reaction mass was poured into water (80 mL) and extracted with EtOAc (2×50 mL). The combined organic extracts were washed with water (3×40 mL), brine (40 mL), dried ($Na_2SO_4$) and evaporated under reduced pressure. The residue was purified by column chromatography on neutral silica gel (60-120 mesh) using 30% EtOAc/hexane as the eluent to afford tert-butyl 4-((tert-butoxycarbonyl(2-chloro- 4-(3-(5-cyanopyrazin-2-yl)ureido)-5-methoxyphenethyl) amino)methyl) piperidine-1-carboxylate (0.280 g, 31%) as a white solid.

1I. 1-(5-chloro-2-methoxy-4-(2-(piperidin-4-yl) methylamino)ethyl)phenyl)-3-(5-cyano pyrazin-2-yl) urea hydrochloride A solution of 4N HCl in dioxane (2.0 mL) was added to a stirred solution of tert-butyl 4-((tert-butoxycarbonyl(2-chloro-4-(3-(5-cyanopyrazin-2-yl)ureido)-5-methoxy phenylethyl)amino)methyl)piperidine-1-carboxylate (0.070 g, 0.108 mmol) in acetonitrile (0.5 mL) at 5° C. The reaction mixture was stirred for 30 minutes at 5° C. then the solvents were evaporated under reduced pressure to afford a yellow solid which was triturated with THF and diethyl ether. The solid was further triturated with hot acetone and the collected solid was dried to yield 1-(5-chloro-2-methoxy-4-(2-(piperidin-4-ylmethylamino)ethyl)phenyl)-3-(5-cyanopyrazin-2-yl)urea hydrochloride (0.030 g, 63%) as a white solid.

Example 8

8A. 1-Bromo-2-chloro-5-isopropoxy-4-nitro-benzene

To a mixture of potassium tert-butoxide (0.22 g, 2.0 mmol) in DMF (5 mL), IPA (0.115 mL, 1.5 mmol) was added at 0° C. and the mixture stirred for 15 minutes. A solution of 1-bromo-2-chloro-5-fluoro-4-nitrobenzene (0.25 g, 1.0 mmol) in DMF (7 mL) was added to the reaction at 0° C. and the mixture stirred for 3 hours at room temperature. Water (100 mL) was added and the mixture extracted with EtOAc (3×50 mL). The combined organic extracts were washed with water (10 mL), brine (10 mL), dried ($Na_2SO_4$) and evaporated under reduced pressure. The residue was purified by column chromatography on neutral silica gel (60-120 mesh) using 0-25% EtOAc/hexanes as the eluent to give 1-bromo-2-chloro-5-isopropoxy-4-nitro-benzene (0.18 g, 62%) as a yellow solid.

The synthesis was completed using the synthetic steps and chemistry described in Example 1C-1I.

For Examples 26, 27, 28, 30, 32, 33 and 37 the synthesis of the primary amine can be achieved using the method described for the synthesis of Example 26.

Example 26

26A. (2-Morpholin-4-yl-2-oxo-ethyl)-carbamic acid tert-butyl ester

A solution of triphenylphosphine (5.44 g, 8.55 mmol) in EtOAc (5 mL) was added dropwise to a stirred solution of tert-butoxycarbonylamino-acetic acid (1 g, 5.70 mmol) in DCM (10 mL) at 0° C. and then mixture was stirred for 30 mins. Morpholine (0.54 g, 6.29 mmol) was added followed by DIPEA (2.20 g, 17.1 mmol) and the mixture stirred at room temperature for 12 hours. Water (70 mL) was added then the separated aqueous phase was extracted with ethyl acetate (4×30 mL). The combined organic extracts were washed with water (100 mL), brine (40 mL), dried ($Na_2SO_4$) and the solvents evaporated under reduced pressure. The residue was purified by column chromatography on neutral silica (60-120 mesh) using 0-1.2% MeOH/DCM as the eluent to give the title compound (1.23 g, 88%) as a white solid.

26B. 2-Amino-1-morpholin-4-yl-ethanone

A solution of 5N HCl in dioxane (1 mL) was added to a stirred solution of (2-morpholin-4-yl-2-oxo-ethyl)-carbamic acid tert-butyl ester (1.23 g, 5.04 mmol) in methanol (10 mL) at 10° C. and the resulting solution stirred at room temperature for 24 hours. The solvents were removed under reduced pressure and the residue neutralized using a saturated solution of $NaHCO_3$. The water was evaporated under reduced pressure and the resulting solid was extracted using methanol (3×20 mL). The solvents were removed under reduced pressure to give the title compound (0.49 g, 68%) as white solid.

The synthesis was completed using the synthetic steps and chemistry described in Example 1D-1I.

Synthetic Route B (Illustrated with reference to Example 10: (S)-1-(5-chloro-4-(2-(1-(1-(cyclopropane carbonyl)piperidin-4-yl) ethylamino)ethyl)-2-methoxyphenyl)-3-(5-cyanopyrazin-2-yl)urea)

10A. (S)-tert-butyl 4-(1-(2-chloro-5-methoxy-4-nitrophenethylamino)ethyl)piperidine-1-carboxylate To a solution of 4-((S)-1-amino-ethyl)-piperidine-1-carboxylic acid tert-butyl ester (0.5 g, 2.19 mmol) in IPA (8 mL), 1-chloro-4-methoxy-5-nitro-2-vinylbenzene (0.39 g, 1.87 mmol) and quinol (0.09 g, 0.87 mmol) were added and the mixture heated to reflux for 56 hours. The solvents were removed under reduced pressure then the residue was purified by column chromatography on neutral silica gel (60-120 mesh) using 4% methanol/DCM as the eluent to give the desired product (0.46 g, 48%).

10B. (S)—N-(2-chloro-5-methoxy-4-nitrophenethyl)-1-(piperidin-4-yl)ethanamine hydrochloride salt A solution of 5N HCl in dioxane (1 mL) was added to a solution of (S)-tert-butyl chloro-5-methoxy-4-nitrophenethylamino)ethyl)piperidine-1-carboxylate (0.5 g, 1.13 mmol) in DCM (10 mL) at 0° C. and the resulting solution stirred for 2 hours. The solvents were evaporated under reduced pressure to give the desired compound (0.42 g, 100%) as a white solid that was used without further purification.

10C. (S)-(4-(1-(2-chloro-5-methoxy-4-nitrophenethylamino)ethyl)piperidin-1yl)(cyclopropyl)methanone To a solution of cyclopropane carboxylic acid (0.063 g, 0.74 mmol) and DIPEA (2 mL) in DCM (30 mL) at 0° C. was added drop-wise a solution of TBTU (0.22 g, 0.71 mmol) in DMF (1 mL). The reaction mixture was allowed to warm to room temperature and a solution of (S)—N-(2-chloro-5-methoxy-4-nitrophenethyl)-1-(piperidin-4-yl) ethanamine hydrochloride salt (0.25 g, 0.66 mmol) in DIPEA (3 mL) and DCM (2 mL) was added.

The mixture was stirred at room temperature for 16 hours then brine (25 mL) was added. The mixture was extracted with DCM (2×30 mL) then the combined organic extracts were dried ($Na_2SO_4$) and evaporated under reduced pressure to give the title compound (0.27 g, 93%).

10D. (S)-tert-butyl 2-chloro-5-methoxy-4-nitrophenethyl(1-(1-(cyclopropane carbonyl)piperidin-4-yl) ethyl)carbamate To a solution of (S)-(4-(1-(2-chloro-5-methoxy-4-nitrophenethylamino)ethyl)piperidin-1yl)(cyclopropyl)methanone (0.27 g, 0.66 mmol) in DCM (30 mL), triethylamine (0.13 mL, 1.32 mmol) and Boc$_2$O (0.21 g, 0.99 mmol) were added at room temperature and the mixture was stirred for 1 hour. DCM (30 mL) and water (50 mL) were added and the mixture stirred for 15 minutes. The separated organic layer was washed with water (2×30 mL), dried (Na$_2$SO$_4$) and the solvents evaporated under reduced pressure to give the title compound (0.29 g, 87%) as a white solid.

10E. (S)-tert-butyl 4-amino-2-chloro-5-methoxy-phenethyl(1-(1-(cyclopropane carbonyl)piperidin-4-yl)ethyl)carbamate To a solution of (S)-tert-butyl 2-chloro-5-methoxy-4-nitrophenethyl(1-(1-(cyclopropane carbonyl)piperidin-4-yl) ethyl)carbamate (0.29 g, 0.56 mmol) in methanol (35 mL), saturated solution of NH$_4$Cl (25 mL) and zinc powder (0.18 g, 2.84 mmol) were added at room temperature and the mixture heated to 50° C. for 2 hours. The reaction mixture was allowed to cool to room temperature and filtered through a plug of cotton. To the filtrate, water (100 mL) was added and the mixture extracted with EtOAc (2×30 mL). The combined organic extracts were washed with water (50 mL), brine (25 mL), dried (Na$_2$SO$_4$) and evaporated under reduced-pressure. The residue was purified by column chromatography on neutral silica gel (60-120 mesh) using 18% EtOAc/hexane as the eluent to give the title compound (0.19 g, 68%).

10F. (S)-tert-butyl 2-chloro-4-(3-(5-cyanopyrazin-2-yl)ureido)-5-methoxyphenethyl(1-(1-(cyclopropanecarbonyl) piperidin-4-yl)ethyl)carbamate To a solution of (S)-tert-butyl 4-amino-2-chloro-5-methoxyphenethyl(1-(1-(cyclo propanecarbonyl)piperidin-4-yl)ethyl)carbamate (0.12 g, 0.25 mmol) in DMF (20 mL), (5-cyano-pyrazin-2-yl)-carbamic acid phenyl ester (0.06 g, 0.25 mmol) was added at room temperature and the reaction was stirred for 3 hours at 100° C. The mixture was allowed to cool to room temperature then poured on to the ice cold water (30 ml) and extracted with ethyl acetate (2×25 mL). The combined organic extracts were and washed with water (100 mL), brine (25 mL), dried (Na$_2$SO$_4$) and evaporated under reduced pressure. The residue was purified by column chromatography on neutral silica gel (60-120 mesh) using 25% EtOAc/hexane as the eluent to give the title compound (0.04 g, 26%) as a white solid.

10G. (S)-1-(5-chloro-4-(2-(1-(1-(cyclopropanecarbonyl)piperidin-4-yl)ethylamino)ethyl)-2-methoxyphenyl)-3-(5-cyanopyrazin-2-yl)urea hydrochloride A solution of 5N HCl in dioxane (1 mL) was added to a solution of (S)-tert-butyl 2-chloro-4-(3-(5-cyanopyrazin-2-yl)ureido)-5-methoxyphenethyl(1-(1-(cyclopropane carbonyl)piperidin-4-yl)ethyl)carbamate (0.035 g, 0.056 mmol) in acetonitrile (5 mL) at 10° C. and the resulting solution stirred for one hour at room temperature. The mixture was diluted with diethyl ether (15 mL) and after stirring the supernatant was decanted and the solid was again triturated with diethyl ether (4-5 mL) and then dried at reduced pressure. The residue was triturated with methanol (2 mL), diethyl ether (3 mL) and dried to give the title compound (28 mg, 95%) as a white solid.

Synthetic Route C (Illustrated with reference to Example 12: 1-{3-Chloro-4-[2-(cyclo-hexylmethyl-amino)-ethyl]-phenyl}-3-(5-cyano-pyrazin-2-yl)urea)

12A. 2-(2-Chloro-4-nitro-phenyl)-malonic acid dimethyl ester

3-Chloro-4-fluoro-nitrobenzene (5.0 g, 28.5 mmol) and dimethyl malonate (3.3 mL, 36.2 mmol) were dissolved in N-methyl pyrrolidinone (131.5 mL). Sodium hydroxide (2.4 g, 60 mmol) was added and the solution was heated at 80° C. for 2.0 hours. The reaction mixture was cooled down to 5° C. and 1N HCl solution was added to give a pH of 2. Water (526 mL) was added and the resulting mixture was stirred for 15 minutes during which time a pale yellow solid precipitated out. The precipitates were collected by filtration and then washed with water (2×10 mL). The resulting solid mass was dissolved in DCM (50 mL), dried (Na$_2$SO$_4$) and the solvent was removed under reduced pressure to afford the title compound (5.5 g, 67%).

12B. (2-Chloro-4-nitro-phenyl)-acetic acid methyl ester 2-(2-Chloro-4-nitro-phenyl)-malonic acid dimethyl ester (6.0 g, 20.9 mmol) and sodium chloride (2.2 g, 37.6 mmol) were added to a mixture of DMSO (100 mL) and water (0.38 mL, 20.9 mmol) and the reaction mixture was heated for 8 hours at 110° C. The reaction mixture was cooled down to RT and then poured into water (500 mL). Ethyl acetate (200 mL) was added to the mixture was then stirred for 15 minutes. The separated aqueous layer was extracted with ethyl acetate (100 mL). The combined organic extracts were washed with brine solution (100 mL), dried (Na$_2$SO$_4$) and the solvents were removed under reduced pressure. The crude product was purified by column chromatography on neutral silica gel (60-120 mesh) using 3-6% EtOAc/hexane as the eluent to give the title compound (2.9 g, 60%).

12C. 2-(2-Chloro-4-nitro-phenyl)-ethanol (2-Chloro-4-nitro-phenyl)-acetic acid methyl ester (17 g, 74 mmol) was dissolved in dry THF (85 mL) and cooled to 0° C. A solution of LiBH$_4$ in THF (2M, 75 mL, 148 mmol) was added drop-wise at 0° C. and the reaction mixture was maintained for 5 hours at room temperature. NH$_4$Cl solution (2 mL) was added to the reaction mixture which was then stirred for 15 minutes. Ethyl acetate (170 mL) and water (85 mL) were added and stirred for 10 minutes. The separated aqueous layer was extracted with EtOAc (85 mL), then the combined organic layers were dried (Na$_2$SO$_4$) and evaporated under reduced pressure. The residue was purified by column chromatography on neutral silica gel (60-120 mesh) using 5-10% EtOAC/hexane as the eluent to give the title compound (10 g, 55%) as a yellow oil.

12D. 1-(2-Bromoethyl)-2-chloro-4-nitrobenzene

To a solution of 2-(2-chloro-4-nitrophenyl)ethanol (0.20 g, 1 mmol) in DCM (10 mL), triphenylphosphine (0.42 g, 1.6 mmol) and carbon tetrabromide (0.40 g, 1.2 mmol) were added at room temperature and the mixture stirred for 6 hours. Water (20 mL) was added and the mixture was extracted with ethyl acetate (2×20 mL). The combined organic extracts were washed with water (15 mL), brine (15 mL), dried (Na$_2$SO$_4$) and evaporated under reduced pressure. The residue was purified by column chromatography on neutral silica gel (60-120 mesh) using 1-10% EtOAc/hexane as the eluent to give the desired product (0.25 g, 93%).

12E. 2-(2-Chloro-4-nitrophenyl)-N-(cyclohexylmethyl)ethanamine

To a solution of 1-(2-bromoethyl)-2-chloro-4-nitrobenzene (0.5 g, 1.89 mmol) in DMSO (20 mL), cyclohexylmethanamine (0.427 g, 3.78 mmol) was added at room temperature. The reaction mixture was stirred for 3 hours then water (80 mL) was added and the mixture was extracted with EtOAc (2×50 mL). The combined organic extracts were washed with water (50 mL), brine (50 mL), dried ($Na_2SO_4$) and evaporated under reduced pressure. The crude product was purified by column chromatography on neutral silica gel (60-120 mesh) using 10-15% EtOAc/hexane as the eluent to give the title compound (0.45 g, 80%) as a yellow solid.

12F. tert-Butyl 2-chloro-4-nitrophenylethyl(cyclohexylmethyl)carbamate

To a solution of 2-(2-chloro-4-nitrophenyl)-N-(cyclohexylmethyl)ethanamine (0.45 g, 1.52 mmol) in DCM (20 mL), triethylamine (0.38 g, 3.38 mmol) was added, followed by addition of $Boc_2O$ (0.39 g, 1.82 mmol) at room temperature and reaction was stirred for one hour. EtOAc (50 mL) and saturated sodium bicarbonate solution (25 mL) were added and the mixture stirred for 15 minutes. The separated organic layer was washed with water (25 mL), dried ($Na_2SO_4$) and evaporated under reduced pressure to give the title compound (0.52 g, 86%) as a yellow solid.

12G. tert-Butyl 4-amino-2-chlorophenethyl(cyclohexylmethyl)carbamate

To a solution of tert-butyl 2-chloro-4-nitrophenethyl(cyclohexylmethyl)carbamate (0.52 g, 1.31 mmol) in methanol (30 mL), saturated solution of $NH_4Cl$ (30 mL) was added at room temperature. Zinc powder (0.42 g, 6.55 mmol) was added and the mixture heated for 2 hours at 45° C. The mixture was allowed to cool to room temperature and the solution was filtered through a celite bed. EtOAc (60 mL) and water (60 mL) were added in to the filtrate and the mixture stirred for 15 minutes. The separated organic layer was washed with water (100 mL), brine (100 mL), dried ($Na_2SO_4$) and the solvent was removed under reduced pressure to afford the title compound (0.42 g, 88%) as a yellow solid.

12H. tert-Butyl 2-chloro-4-(3-(5-cyanopyrazin-2-yl)ureido)phenethyl(cyclohexylmethyl) carbamate To a solution of tert-butyl 4-amino-2-chlorophenethyl (cyclohexylmethyl)carbamate (0.42 g, 1.14 mmol) in DMF (12 mL), phenyl 5-cyanopyrazin-2-ylcarbamate (0.27 g, 1.14 mmol) were added and the mixture heated for 2 hours at 100° C. The mixture was allowed to cool to room temperature, diluted with water (50 mL) and extracted with EtOAc (2×20 mL). The combined organic extracts were washed with water (50 mL), brine (50 mL), dried ($Na_2SO_4$) and evaporated under reduced pressure. The residue was purified by column chromatography on neutral silica gel (60-120 mesh) using 10-25% EtOAc/hexane as the eluent to give the title compound (0.32 g, 56%) as a white solid.

12I. 1-(3-Chloro-4-(2-(cyclohexylmethylamino)ethyl)phenyl)-3-(5-cyanopyrazin-2-yl)urea trifluoroacetate A solution of tert-butyl 2-chloro-4-(3-(5-cyanopyrazin-2-yl)ureido)phenethyl(cyclohexylmethyl)carbamate (0.32 g, 0.62 mmol) in DCM (22 mL) was cooled to 0° C. and TFA (0.60 mL) was added and the mixture stirred at 0° C. for 4 hours. The solvents were evaporated under reduced pressure then the residue taken up in DCM (22 mL) and cooled to 0° C. Ammonia solution (1 mL) was added and the mixture stirred at 0° C. for one hour, then the solvents were removed under reduced pressure. The residue was washed with DCM (2×10 mL), pentane (10 mL) and dried under reduced pressure.

The product was purified by preparative HPLC using the method below to give the desired compound (0.06 g, 23%) as a white solid.

Preparative HPLC was carried out using X Bridge $C_{18}$ 150×21.20 mm, 5 micron at 267 nm. Column flow was 21 mL/min and solvents used were 0.1% TFA in HPLC grade water (A) and 0.1% TFA in HPLC grade acetonitrile (B).

Method is as described below.

LC (method) RT=9.365

| Time (min) | A | B |
| --- | --- | --- |
| 0.01 | 70 | 30 |
| 10.00 | 30 | 70 |
| 12.00 | 0 | 100 |
| 12.01 | 70 | 30 |
| 13.00 | 70 | 30 |

12 J. 1-(3-Chloro-4-(2-(cyclohexylmethylamino)ethyl)phenyl)-3-(5-cyanopyrazin-2-yl)urea hydrochloride A solution of tert-butyl 2-chloro-4-(3-(5-cyanopyrazin-2-yl)ureido)phenethyl(2-methoxybenzyl)carbamate (0.06 g, 0.14 mmol) in DCM (10 mL) was cooled to 0° C. and HCl in dioxane (0.3 mL) was added and the mixture stirred for one hour. The solvents were removed under reduced pressure and the residue washed with DCM (2×5 mL), followed by pentane (10 mL) and the solid was dried under reduced pressure to give the title compound (25 mg, 38%) as a white solid.

Synthetic Route D (Illustrated with reference to Example 15: (R)-Morpholine-2-carboxylic acid (2-{2-chloro-4-[3-(5-cyano-pyrazin-2-yl)-ureido]-5-methoxy-phenyl}-ethyl)-amide hydrochloride)

15A. [2-(2-Chloro-5-methoxy-4-nitro-phenyl)-ethyl]-(2,4-dimethoxy-benzyl)-amine To a solution of 2,4-dimethoxybenzylamine (3.0 g, 17.9 mmol) in IPA (10 mL), 1-chloro-4-methoxy-5-nitro-2-vinylbenzene (3.4 g, 16.3 mmol) and quinol (0.71 g, 6.52 mmol) were added. The mixture was heated to 70° C. for 20 hours, allowed to cool to room temperature and the solvents evaporated under reduced pressure. The crude product was purified by column chromatography on neutral silica gel (60-120 mesh) using 0-1% MeOH/DCM as the eluent to give the title compound (2.5 g, 41.2%).

15B. 2-(2-Chloro-5-methoxy-4-nitro-phenyl)-ethylamine

Ceric ammonium nitrate (21.6 g, 39.4 mmoL) was added portionwise to a stirred solution of [2-(2-chloro-5-methoxy-4-nitro-phenyl)-ethyl]-(2,4-dimethoxy-benzyl)-amine (5.0 g, 13.1 mmol) in acetonitrile (25 mL) and water (5 mL) at 0° C. The reaction mixture was allowed to stir at 0° C. for 30 mins followed by RT for 2 hrs. After completion of the reaction, water (100 mL) was added and the mixture extracted with EtOAc (3×100 mL). The combined organic extracts were washed with water (2×30 mL), dried ($Na_2SO_4$) and evaporated under reduced pressure. The crude product was purified by column chromatography on neutral silica gel (60-120 mesh) using 0-5% MeOH/DCM as the eluent to give the title compound (1.2 g, 40%).

15C. (R)-2-[2-(2-Chloro-5-methoxy-4-nitro-phenyl)-ethylcarbamoyl]-morpholine-4-carboxylic acid tert-butyl ester 2-(1H-7-Azabenzotriazol-1-yl)-1,1,3,3-tetramethyl uronium hexafluorophosphate methanaminium (0.74 g, 1.94 mmol) was added to a stirred solution of (R)-morpholine-2,4-dicarboxylic acid 4-tert-butyl ester (0.3 g, 1.29 mmol) in DMF (7 mL) at 0° C. The reaction mixture was stirred at 0° C. for 30 mins then 2-(2-chloro-5-methoxy-4-nitro-phenyl)-ethylamine (0.36 g, 1.55 mmol) and DIPEA (0.25 g, 1.94 mmol) were added and the mixture allowed to stir for 2 hours at 0° C. The mixture was poured in to water (150 mL) and extracted with DCM (2×120 mL). The combined organic extracts were washed with water (2×50 mL), brine (25 mL), dried ($Na_2SO_4$) and evaporated under reduced pressure. The residue was purified by column chromatography on neutral silica gel (60-120 mesh) using 0-0.8% MeOH/DCM as the eluent to give the title compound (0.4 g, 70%).

15D. (R)-2-[2-(4-Amino-2-chloro-5-methoxy-phenyl)-ethylcarbamoyl]-morpholine-4-carboxylic acid tert-butyl ester To a solution of (R)-2-[2-(2-chloro-5-methoxy-4-nitro-phenyl)-ethylcarbamoyl]-morpholine-4-carboxylic acid tert-butyl ester (0.4 g, 0.90 mmol) in methanol (15 mL), saturated solution of $NH_4Cl$ (10 mL) was added at room temperature. Zinc powder (0.29 g, 4.5 mmol) was added and the mixture heated for 4 hours at 50° C. The mixture was allowed to cool to room temperature and the solution was filtered through a celite bed. EtOAc (60 mL) and water (60 mL) were added to the filtrate and the mixture stirred for 15 minutes. The separated organic layer was washed with water (100 mL), brine (100 mL), dried ($Na_2SO_4$) and evaporated under reduced pressure to afford the title compound (0.28 g, 76%) as a yellow solid.

15E. (R)-2-(2-{2-Chloro-4-[3-(5-cyano-pyrazin-2-yl)-ureido]-5-methoxy-phenyl}-ethylcarbamoyl)-morpholine-4-carboxylic acid tert-butyl ester Phenyl 5-cyanopyrazin-2-ylcarbamate (0.1 g, 0.43 mmol) was added to a stirred solution of (R)-2-[2-(4-amino-2-chloro-5-methoxy-phenyl)-ethylcarbamoyl]-morpholine-4-carboxylic acid tert-butyl ester (0.18 g, 0.43 mmol) in DMF (2 mL). The mixture was stirred at 90° C. for 2 hrs then the mixture allowed to cool to room temperature. The solvents were evaporated under reduced pressure to leave a residue that was purified by trituration using methanol (3×5 mL) to afford the title compound (0.13 g, 54%) as a white solid.

15F. (R)-Morpholine-2-carboxylic acid (2-{2-chloro-4-[3-(5-cyano-pyrazin-2-yl)-ureido]-5-methoxy-phenyl}-ethyl)-amide hydrochloride 3N HCl in dioxane (0.7 mL) was added to a stirred solution of (R)-2-(2-{2-chloro-4-[3-(5-cyano-pyrazin-2-yl)-ureido]-5-methoxy-phenyl}-ethylcarbamoyl)-morpholine-4-carboxylic acid tert-butyl ester (0.10 g, 0.18 mmol) in acetonitrile (3 mL) and dry THF (2 mL) at 10° C. The reaction was stirred for 30 minutes at room temperature then heated to 60° C. for 1 hr. The mixture was allowed to cool to room temperature and the solvents evaporated under reduced pressure. The resulting solid was triturated with methanol (2×3 mL) followed by diethyl ether (2×10 mL) and dried under reduced pressure to give the title compound (0.074 g, 94%) as a white solid.

Synthetic Route E (Illustrated with reference to Example 16: N-(2-{2-Chloro-4-[3-(5-cyano-pyrazin-2-yl)-ureido]-5-methoxy-phenyl}-ethyl)-2-morpholin-4-yl-acetamide hydrochloride)

16A. 2-Chloro-N-[2-(2-chloro-5-methoxy-4-nitro-phenyl)-ethyl]-acetamide

Chloroacetyl chloride (0.14 g, 1.30 mmol) was added dropwise to a stirred solution of 2-(2-chloro-5-methoxy-4-nitro-phenyl)-ethylamine (0.3 g, 1.30 mmol) and triethylamine (0.14 g, 1.43 mmol) in DCM (15 mL) at 0° C. under a $N_2$ atmosphere. The mixture was stirred at 0° C. for 30 mins then allowed to warm to room temperature and stirring continued for a further 2 hrs. Water (70 mL) was added and the mixture extracted with DCM (3×50 mL), The combined organic extracts were washed with water (2×30 mL), dried ($Na_2SO_4$) and evaporated under reduced pressure to give the title compound, (0.31 g, 76%) which was used without further purification.

16B. N-[2-(2-Chloro-5-methoxy-4-nitro-phenyl)-ethyl]-2-morpholin-4-yl-acetamide Morpholine (0.09 g, 1.06 mmol) was added to a stirred solution of 2-chloro-N-[2-(2-chloro-5-methoxy-4-nitro-phenyl)-ethyl]-acetamide (0.31 g, 0.96 mmol) and potassium carbonate (0.20 g, 1.45 mmol) in MeCN (5 mL). The stirred mixture was heated to 70° C. for 8 hrs then allowed to cool to room temperature. Water (60 mL) was added and the mixture extracted with EtOAc (3×30 mL). The combined organic extracts were washed with water (2×30 mL), dried ($Na_2SO_4$) and evaporated under reduced pressure to give the title compound (0.21 g, 62%) which was used without further purification.

16C. N-[2-(4-Amino-2-chloro-5-methoxy-phenyl)-ethyl]-2-morpholin-4-yl-acetamide Zinc powder (0.19 g, 2.96 mmol) was added to a stirred solution of N-[2-(2-Chloro-5-methoxy-4-nitro-phenyl)-ethyl]-2-morpholin-4-yl-acetamide (0.21 g, 0.59 mmol) in saturated solution of $NH_4Cl$ (15 mL) and MeOH (20 mL). The stirred mixture was heated to 50° C. for 6.0 hrs then the reaction mass was cooled to room temperature filtered through cotton wool. The MeOH was removed under reduced pressure then the residue was partitioned between water (70 mL) and EtOAc (30 mL). The separated aqueous phase was extracted with EtOAc (3×30 mL), then the combined organic extracts were washed with water (50 mL), brine (25 mL), dried (Na$_2$SO$_4$) and evaporated under reduced pressure to give the title compound (0.16 g, 83%) as a yellow solid. This material was used without further purification.

16D. N-(2-{2-Chloro-4-[3-(5-cyano-pyrazin-2-yl)-ureido]-5-methoxy-phenyl}-ethyl)-2-morpholin-4-yl-acetamide hydrochloride Phenyl 5-cyanopyrazin-2-ylcarbamate (0.11 g, 0.48 mmol) was added to a stirred solution of N-[2-(4-amino-2-chloro-5-methoxy-phenyl)-ethyl]-2-morpholin-4-yl-acetamide (0.16 g, 0.48 mmol) in DMF (2 mL). The mixture was stirred at 90° C. for 1.5 hrs then the mixture allowed to cool to room temperature. The solvents were evaporated under reduced pressure to leave a residue that was purified by trituration using methanol (3×5 mL) to afford a white solid. The solid was taken up in anhydrous THF (2 mL) and a 3N HCl in dioxane solution (0.5 mL) was added at 10° C. and the mixture stirred for 30 mins. The solvents were removed under reduced pressure to leave a solid that was triturated with diethyl ether (2×10 mL) and dried under reduced pressure to give the title compound (94 mg, 92%) as a white solid.
Synthetic Route F
(Illustrated with reference to Example 25: 1-(5-Chloro-2-methoxy-4-[2-(2-morpholin-4-yl-ethylamino)-ethoxy]-phenyl)-3-(5-cyano-pyrazin-2-yl)-urea hydrochloride)

25A. 2-chloro-5-methoxyphenol

Sulfuryl chloride (6.52 g, 48.3 mmol) was added dropwise to a stirred solution of 3-methoxyphenol (5.0 g, 40.2 mmol) in CHCl$_3$ (50 mL) at 0° C. and the resulting mixture stirred for 30 minutes. The temperature was raised to 65° C. and stirring continued for 3 hours before allowing the mixture to cool to room temperature. The reaction mass was poured in to ice cold water (100 mL), then the separated aqueous phase was extracted with CHCl$_3$ (2×50 mL). The combined organic extracts were washed with saturated aqueous NaHCO$_3$ solution (30 mL), brine (30 mL), dried (Na$_2$SO$_4$) and the solvents removed under reduced pressure. The residue was purified by column chromatography on neutral silica gel (60-120 mesh) using 0-3% EtOAc/hexane as the eluent to give the title compound (2.6 g, 41%).

25B. 1-Chloro-2-(2-chloro-ethoxy)-4-methoxy-benzene

1-Bromo-2-chloroethane (4.61 g, 32.16 mmol) was added to a stirred suspension of 2-chloro-5-methoxyphenol (3.4 g, 21.44 mmol) and K$_2$CO$_3$ (4.43 g, 32.16 mmol) in DMF (30 mL) at room temperature. The mixture was heated to 60° C. and stirring continued for 12 hours. The reaction mass was allowed to cool to room temperature and poured into water (100 mL). The mixture was extracted with EtOAc (2×50 mL), then the combined organic extracts were washed with brine (20 mL), dried (Na$_2$SO$_4$) and the solvents removed under reduced pressure to afford the title compound (2.2 g, 47%).

25C. 1-Chloro-2-(2-chloroethoxy)-4-methoxy-5-nitrobenzene

Trifluroacetic anhydride (9.40 g, 44.7 mmol) was added to a stirred solution of tetrabutylammonium nitrate (3.02 g, 9.95 mmol) and 18-crown-6 (0.39 g, 1.49 mmol) in DCM (10 mL) at −10° C. and the mixture stirred for 30 minutes. A solution of 1-chloro-2-(2-chloro-ethoxy)-4-methoxy-benzene (2.2 g, 9.95 mmol) in DCM (10 mL) was added dropwise maintaining the temperature at −10° C. and stirring continued for 2 hours at −10° C. Saturated ammonium chloride solution (50 mL) was added and the mixture stirred at room temperature for 30 minutes. The mixture was extracted with EtOAc (2×30 mL) then the combined organis extracts were washed with water (30 mL), brine (20 mL), dried (Na$_2$SO$_4$) and evaporated under reduced pressure. The residue was purified by column chromatography on neutral silica gel (60-120 mesh) using 0-5% EtOAc/hexane as the eluent to give the title compound (2.3 g, 87%) as a yellow solid.

25D. [2-(2-Chloro-5-methoxy-4-nitro-phenoxy)-ethyl]-(2-morpholin-4-yl-ethyl)-amine 2-Morpholin-4-yl-ethylamine (0.29 g, 2.06 mmol) was added to a stirred solution of 1-chloro-2-(2-chloroethoxy)-4-methoxy-5-nitrobenzene (0.5 g, 1.87 mmol) and triethylamine (0.28 g, 2.81 mmol) in MeCN (10 mL). The stirred solution was heated to 70° C. for 24 hours and then the mixture was allowed to cool to room temperature and water (50 mL) was added. The mixture was extracted with EtOAc (2×50 mL), then the combined organic extracts were washed with water (50 mL), brine (25 mL) and dried (Na$_2$SO$_4$). The solvents were removed under reduced pressure to give the title compound (0.2 g, 30%) which was used without further purification.

25E. [2-(2-Chloro-5-methoxy-4-nitro-phenoxy)-ethyl]-(2-morpholin-4-yl-ethyl)-carbamic acid tert-butyl ester

[2-(2-Chloro-5-methoxy-4-nitro-phenoxy)-ethyl]-(2-morpholin-4-yl-ethyl)-amine (0.2 g, 0.55 mmol) was added to a stirred solution of triethylamine (0.11 g, 1.11 mmol) and BOC anhydride (0.17 g, 0.82 mmol) in DCM (15 mL) at room temperature. The mixture was stirred for 6 hours then the solvents were removed under reduced pressure. The residue was purified by column chromatography on neutral silica gel (60-120 mesh) using 0-2% MeOH/DCM as the eluent to give the title compound (0.21 g, 84%) as a yellow solid.

25F. [2-(4-Amino-2-chloro-5-methoxy-phenoxy)-ethyl]-(2-morpholin-4-yl-ethyl)-carbamic acid tert-butyl ester Zinc powder (0.14 g, 2.28 mmol) was added to a stirred solution of [2-(2-chloro-5-methoxy-4-nitro-phenoxy)-ethyl]-(2-morpholin-4-yl-ethyl)-carbamic acid tert-butyl ester (0.21 g, 0.45 mmol) in a mixture of saturated NH$_4$Cl solution (10 mL) and methanol (15 mL) at room temperature. The stirred suspension was heated at 50° C. for 3 hours then allowed to cool to room temperature and filtered through a plug of cotton wool. The methanol was removed under reduced pressure then water (100 mL) was added and the mixture extracted with EtOAc (2×50 mL). The combined organic extracts were washed with water (50 mL), brine (25 mL), dried (Na$_2$SO$_4$) and evaporated under reduced pressure to give the title compound (0.11 g, 56%) as an off-white solid which was used without further purification.

25G. (2-{2-Chloro-4-[3-(5-cyano-pyrazin-2-yl)-ureido]-5-methoxy-phenoxy}-ethyl)-(2-morpholin-4-yl-ethyl)-carbamic acid tert-butyl ester Phenyl 5-cyanopyrazin-2-ylcarbamate (0.08 g, 0.33 mmol) was added to a stirred solution of [2-(4-amino-2-chloro-5-methoxy-phenoxy)-ethyl]-(2-morpholin-4-yl-ethyl)-carbamic acid tert-butyl ester (0.11 g, 0.25 mmol) in DMF (1 mL). The mixture was stirred at 100° C. for 45 minutes then the mixture allowed to cool to room temperature. The solvents were evaporated under reduced pressure to leave a residue that was purified by trituration with methanol (3×5 mL) and dried to give the title compound (60 mg, 41%) as a white solid.

25H. 14-[2-(2-morpholin-4-yl-ethylamino)-ethoxy]-phenyl)-3-(5-cyano-pyrazin-2-yl)-urea hydrochloride A 3N solution of HCl in dioxane (0.5 mL) was added to a stirred solution of (2-{2-chloro-4-[3-(5-cyano-pyrazin-2-yl)-ureido]-5-methoxy-phenoxy}-ethyl)-(2-morpholin-4-yl-ethyl)-carbamic acid tert-butyl ester (0.06 g, 0.10 mmol) in THF (2 mL) and acetonitrile (5 mL) at 0° C. The mixture was allowed to warm to room temperature and stirring continued for 30 min then heated to 60° C. for 5 hours. The solution was allowed to cool to room temperature then the solvents were removed under reduced pressure. The resulting solid was triturated with methanol (2×3 mL) and diethyl ether (2×10 mL), dried under reduced pressure to give the title compound (0.034 g, 69%) as a white solid.

Biological Activity

Example A

Chk-1 Kinase Inhibiting Activity

The compounds of the invention were tested for activity against Chk-1 kinase using the materials and protocols set out below.
Reaction Buffer:
Base Reaction buffer: 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO
Required cofactors are added individually to each kinase reaction
Reaction Procedure:
(i) Prepare indicated substrate in freshly prepared Base Reaction Buffer
(ii) Deliver any required cofactors to the substrate solution above
(iii) Deliver indicated kinase into the substrate solution and gently mix
(iv) Deliver compounds in DMSO into the kinase reaction mixture
(v) Deliver $^{33}$P-ATP (specific activity 0.01 μCi/μl final) into the reaction mixture to initiate the reaction.
(vi) Incubate kinase reaction for 120 minutes at room temperature
(vii) Reactions are spotted onto P81 ion exchange paper (Whatman #3698-915)
(viii) Wash filters extensively in 0.1% phosphoric acid.
(ix) Dry filters and measure counts in scintillation counter
Kinase Information:
CHK-1—Genbank Accession # AF016582
Recombinant full length construct, N-terminal GST tagged, purified from insect cells.
No special measures were taken to activate this kinase.
Final concentration in assay=0.5 nM
Substrate: CHKtide
Peptide sequence: [KKKVSRSGLYRSPSMPENLNRPR]
Final concentration in assay=20 μM
No additional cofactors are added to the reaction mixture
From the results obtained by following the above protocol, the IC$_{50}$ values against Chk-1 kinase of a number of the compounds of the Examples were determined and these are shown in Table 3.

TABLE 3

| Example | IC$_{50}$ (μM) |
|---|---|
| 1 | 0.0001 |
| 2 | 0.00009 |
| 3 | 0.00014 |
| 4 | 0.00005 |
| 5 | 0.00006 |
| 6 | 0.0001 |
| 7 | 0.0008 |
| 8 | 0.00075 |
| 9 | 0.00069 |
| 10 | 0.00065 |
| 11 | 0.00028 |
| 12 | 0.030 |
| 13 | 0.00027 |
| 14 | 0.00040 |
| 15 | 0.020 |
| 16 | 0.076 |
| 17 | 0.013 |
| 18 | 0.00052 |
| 19 | 0.0019 |
| 20 | 0.0071 |
| 21 | 0.010 |
| 22 | 0.0082 |
| 23 | 0.019 |
| 24 | 0.0011 |
| 25 | 0.00061 |
| 26 | 0.00058 |
| 27 | 0.00021 |
| 28 | 0.00048 |
| 30 | 0.0029 |

Example B

Studies were carried out to test the effect of compounds on the inhibition of cell growth in MOLM-13 and MV4-11 cells.
The following protocol was used:
(a) Cells were seeded in 96-well plates at cell densities of 2500/well (MOLM-13) and 10,000/well (MV4-11). Cells were then incubated overnight prior to addition of compound or vehicle control.
(b) Test compounds were prepared from 10 mM DMSO stocks to give a final concentration range of 10 μM, 3 μM, 1 μM, 0.3 μM, 0.1 NM, 0.03 μM, 0.01 μM, 0.03 μM, 0.01 μM and vehicle control. The DMSO content was constant at 0.1%.
(c) Test compounds were incubated with the cells for 72 h at 37° C. 5% CO$_2$ in a humidified atmosphere.
(d) Alamar blue 10% (v/v) was then added and incubated for a further 4 h, and fluorescent product detected using the BMG FLUOstar plate reader.

(e) Media only background values were subtracted and the data analysed using a 4-parameter logistic equation in GraphPad Prism.

From the results obtained by following the above protocol, the $IC_{50}$ values against MOLM-13 and MV4-11 cells of compounds of the Examples were determined and these are shown in Table 4 below.

TABLE 4

| Example | MOLM-13 $IC_{50}$ (μM) | MV4-11 $IC_{50}$ (μM) |
|---|---|---|
| 1 | 0.240 | 0.386 |
| 2 | 0.026 | 0.209 |
| 3 | 0.081 | 0.173 |
| 4 | 0.049 | 0.111 |
| 5 | 0.107 | 0.178 |
| 6 | 0.073 | 0.127 |
| 7 | 0.113 | 0.295 |
| 8 | 0.028 | 0.038 |
| 9 | 0.029 | 0.056 |
| 10 | 0.035 | 0.080 |
| 11 | 0.059 | 0.231 |
| 12 | 1.60 | 0.740 |
| 14 | — | 0.202 |
| 18 | — | 0.175 |
| 19 | — | 0.481 |
| 21 | — | 3.76 |
| 22 | — | 0.519 |
| 23 | — | 4.79 |
| 26 | — | 0.800 |
| 27 | — | 0.135 |
| 28 | — | 0.390 |

Example C

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and filling the resulting mixture into standard opaque hard gelatin capsules.

(iii) Injectable Formulation I

A parenteral composition for administration by injection can be prepared by dissolving a compound of the formula (1) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (1) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (1) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (1) with pharmaceutical grade corn oil to give a concentration of 5 mg/ml. The composition is sterilised and filled into a suitable container.

viii) Lyophilised Formulation

Aliquots of formulated compound of formula (1) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 milliliter.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

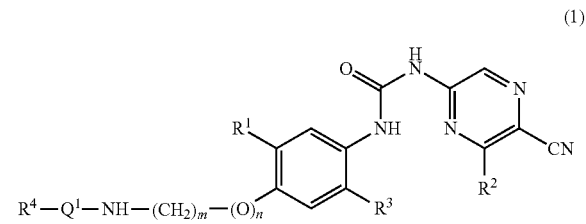

or a salt, N-oxide or tautomer thereof, wherein:

m is 2, 3 or 4;

n is 0 or 1;

$Q^1$ is selected from a bond; C(=O); S(O); $SO_2$; and an alkylene chain of 1 to 4 carbon atoms in length between the moiety $R^4$ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl or cyclobutane-1,1-diyl group; and/or (c) one carbon atom of the 1 to 4 carbon atoms of the alkylene chain may optionally be replaced by C(=O), S(O), or $SO_2$, provided that $Q^1$ contains no more than one C(=O), S(O), or $SO_2$ moiety;

$R^1$ is selected from hydrogen, methyl, chlorine and bromine;

$R^2$ is selected from hydrogen, methyl, methoxy and a group $-(O)_p$-$Q^2$-$R^5$;

p is 0 or 1;

R³ is selected from hydrogen, a group Hyd¹, a group —O-Hyd¹ and a group —(O)$_p$-Q²-R⁵;

provided that when one of R² and R³ is —(O)$_p$-Q²-R⁵, the other is selected from hydrogen, methoxy and methyl;

Hyd¹ is a non-aromatic $C_{1-6}$ hydrocarbon group;

R⁴ is selected from amino, NH-Hyd², N(Hyd²)₂; and a non-aromatic carbocyclic or heterocyclic ring of 4 to 7 ring members containing 0, 1, 2 or 3 heteroatom ring members selected from O, N and S and oxidised forms thereof; the carbocyclic or heterocyclic ring being optionally substituted with one or two substituents R⁹;

Hyd² is an unsubstituted non-aromatic $C_{1-6}$ hydrocarbon group; or a substituted non-aromatic $C_{2-6}$ hydrocarbon group bearing one or two substituents selected from hydroxy and amino;

Q² is an alkylene chain of 1 to 4 carbon atoms in length wherein one or more of the 1 to 4 carbon atoms of the alkylene chain may optionally be substituted with one or two $C_{1-4}$ alkyl groups and wherein one carbon atom of the 1 to 4 carbon atoms of the alkylene chain may optionally be replaced by a cyclopropane-1,1-diyl or cyclobutane-1,1-diyl group;

R⁵ is selected from NR⁶R⁷, or N(O)R⁶R⁷ and a cyclic group R⁸;

R⁶ and R⁷ are each independently selected from hydrogen and $C_{1-4}$ alkyl; or NR⁶R⁷ or N(O)R⁶R⁷ form a saturated heterocyclic ring of 4 to 7 ring members optionally containing a second heteroatom ring member selected from O, N and S and oxidised forms of N and S and being optionally substituted with one, two or three substituents selected from oxo, fluorine and methyl;

R⁸ is a 4- to 8-membered non-aromatic heterocyclic group containing 1 or 2 heteroatom ring members selected from O, N, S and oxidised forms of N and S, wherein the heterocyclic group is optionally substituted with one, two or three substituents selected from oxo, fluorine and methyl; and wherein R⁸ is attached to Q² through a carbon atom of the heterocyclic group;

R⁹ is selected from oxo, halogen, cyano and a group R$^a$-R$^b$;

R$^a$ is a bond, O, CO, X¹C(X²), C(X²)X¹, X¹C(X²)X¹, S, SO, SO₂, NR$^c$, SO₂NR$^c$ or NR$^c$SO₂;

R$^b$ is:
  hydrogen;
  a carbocyclic and heterocyclic group having from 3 to 7 ring members, of which 0, 1, 2 or 3 are heteroatom ring members selected from O, N and S and oxidised forms of N and S, the carbocyclic or heterocyclic group being optionally substituted with one or more substituents R¹⁰; and
  an acyclic $C_{1-6}$ hydrocarbon group optionally substituted with one or more substituents selected from hydroxy; oxo; halogen; cyano; nitro; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of N and S, the carbocyclic or heterocyclic group being optionally substituted with one or more substituents R¹⁰; wherein one or two but not all of the carbon atoms of the acyclic $C_{1-6}$ hydrocarbon group may optionally be replaced by O, S, SO, SO₂, NR$^c$, X¹C(X²), C(X²)X¹ or X¹C(X²)X¹;

R¹⁰ is selected from R⁹ except that R¹⁰ does not consist of or contain a cyclic group;

X¹ is O, S or NR$^c$; and

X² is =O, =S or =NR$^c$; and

R$^c$ is hydrogen or $C_{1-4}$ alkyl.

2. A compound according to claim 1 wherein Q¹ is selected from a bond; C(=O); S(O); SO₂; and an alkylene chain of 1 to 4 carbon atoms in length between the moiety R⁴ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl group; and/or (c) one carbon atom of the 1 to 4 carbon atoms of the alkylene chain may optionally be replaced by C(=O), S(O), or SO₂, provided that Q¹ contains no more than one C(=O), S(O), or SO₂ moiety.

3. A compound according to claim 1 wherein R¹ is chlorine.

4. A compound according to claim 1 wherein n is 0.

5. A compound according to claim 1 wherein m is 2.

6. A compound according to claim 1 wherein Q¹ is an alkylene chain of 1 to 4 carbon atoms in length between the moiety R⁴ and the nitrogen atom N, wherein (a) one or more of the 1 to 4 carbon atoms of the alkylene chain may optionally be substituted with one or two $C_{1-4}$ alkyl groups; and/or (b) one carbon atom of the 1 to 4 carbon atoms of the alkylene chain may optionally be replaced by a cyclopropane-1,1-diyl group.

7. A compound according to claim 6 wherein the alkylene chain is represented by —CH₂—CH₂—, —CH₂— or —CHMe-.

8. A compound according to claim 1 wherein R² is hydrogen.

9. A compound according to claim 1 wherein R³ is selected from hydrogen and $C_{1-3}$ alkoxy.

10. A compound according to claim 1 wherein R⁴ is an optionally substituted 4- to 7-membered carbocyclic or heterocyclic ring.

11. A compound according to claim 10 wherein R⁴ is selected from optionally substituted cyclohexyl, piperidinyl, piperazinyl and morpholinyl groups.

12. A compound according to claim 11 wherein R⁴ is selected from groups A to L below, wherein the asterisk indicates the point of attachment to Q¹:

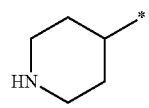

A

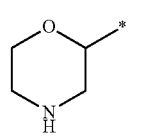

B

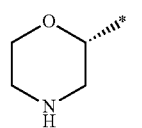

C

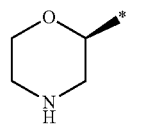

D

-continued

E 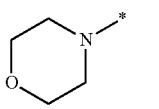

F 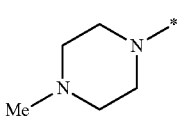

G 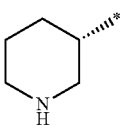

H 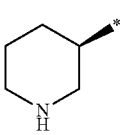

-continued

J 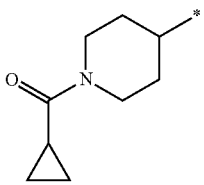

K 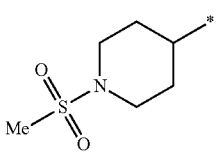

L 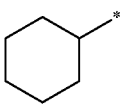

M 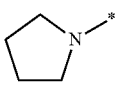

13. A compound according to claim 1 having the formula (2):

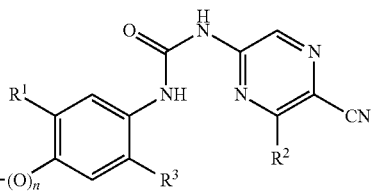

or a salt or tautomer thereof, wherein $R^2$, $R^3$, $R^4$ and $Q^1$ are as defined in any one of claims 1 to 12.

14. A compound according to claim 1 having the formula (3):

or a salt, N-oxide or tautomer thereof, wherein:
q is 0, 1 or 2 and r is 0, 1 or 2 provided that the sum of q and r is 1, 2 or 3;
$R^p$, $R^q$, $R^r$ and $R^s$ are each independently selected from hydrogen and $C_{1-3}$ alkyl; and/or
$CR^pR^q$ and $CR^rR^s$ may each form a cyclopropane-1,1-diyl or 1,1-cyclobutanediyl group;
and m, n, $R^1$, $R^2$, $R^3$ and $R^4$ are as defined in any one of claims 1 to 12.

15. A pharmaceutical composition comprising a compound as defined in claim 1 and a pharmaceutically acceptable excipient.

16. A compound as defined in claim 1, optionally in combination with another chemotherapeutic agent or radiotherapy, for use in the treatment of a proliferative disease.

17. A compound as defined in claim 1, with the structure

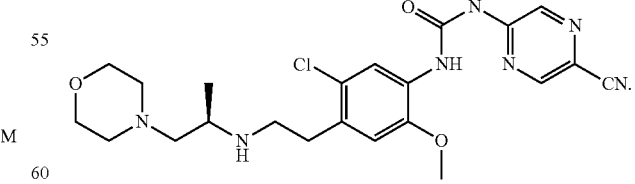

* * * * *